(12) United States Patent
Wigerinck et al.

(10) Patent No.: US 10,376,520 B2
(45) Date of Patent: Aug. 13, 2019

(54) METHODS FOR THE TREATMENT OF CARDIOVASCULAR DISORDERS

(71) Applicant: Galapagos NV, Mechelen (BE)

(72) Inventors: Piet Tom Bert Paul Wigerinck, Mechelen (BE); Gerben Albert Eleutherius Van 'T Klooster, Mechelen (BE)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 15/566,002

(22) PCT Filed: Mar. 31, 2016

(86) PCT No.: PCT/EP2016/057103
§ 371 (c)(1),
(2) Date: Oct. 12, 2017

(87) PCT Pub. No.: WO2016/165952
PCT Pub. Date: Oct. 20, 2016

(65) Prior Publication Data
US 2018/0185377 A1 Jul. 5, 2018

(30) Foreign Application Priority Data

Apr. 13, 2015 (GB) .................................. 1506228.4
Apr. 27, 2015 (GB) .................................. 1507109.5
Jul. 29, 2015 (GB) .................................. 1513344
Aug. 7, 2015 (GB) .................................. 1513991.8
Dec. 7, 2015 (GB) .................................. 1521542.9

(51) Int. Cl.
| A61K 31/541 | (2006.01) |
| A61P 9/10 | (2006.01) |
| A61P 3/06 | (2006.01) |
| A61K 45/06 | (2006.01) |
| A61K 31/54 | (2006.01) |

(52) U.S. Cl.
CPC ............ *A61K 31/541* (2013.01); *A61K 31/54* (2013.01); *A61K 45/06* (2013.01); *A61P 3/06* (2018.01); *A61P 9/10* (2018.01)

(58) Field of Classification Search
CPC ......... A61K 31/541; A61K 45/06; A61P 9/10; A61P 3/06
See application file for complete search history.

(56) References Cited

FOREIGN PATENT DOCUMENTS

| WO | WO 2010/149769 | 12/2010 | | |
| WO | WO-2010149771 A1 * | 12/2010 | ........... | C07D 471/04 |
| WO | WO 2013/189771 | 12/2013 | | |
| WO | WO 2015/117981 | 8/2015 | | |

OTHER PUBLICATIONS

Luc Van Rompaey, et al., Preclinical Characterization of GLPG0634, a Selective Inhibitor of JAK1, for the Treatment of Inflammatory Diseases, J Immunol 2013; 191:3568-3577 (Year: 2013).*

Carmen Gomez-Guerrero, Benat Mallavia, & Jesus Egido, Targeting Inflammation in Cardiovascular Diseases. Still a Neglected field? Cardiovascular Therapeutics 30 (2012) e189-e197 (Year: 2012).*

International Search Report dated Jun. 8, 2016, in Int'l Application No. PCT/EP2016/057103.

L. Van Rompaey et al., "Preclinical Characterization of GLPG634, a Selective Inhibitor of JAK1, for the Treatment of Inflammatory Diseases," The Journal of Immunology, vol. 191, No. 7, Sep. 4, 2017.

Gras, "Filgotinib," Drugs of the Future, vol. 39, No. 8, Aug. 2014.

Charles-Schoeman, et al., "Potential mechanisms leading to the abnormal lipid profile in patients with rheumatoid arthritis versus healthy volunteers and reversal by Tofacitinib," Arthritis & Rheumatology, vol. 67, No. 3, Mar. 2015.

Menet et al., "Triazolopyridines as Selective JAK1 Inhibitors: From Hit Identification to GLPG0634," Journal of Medicinal Chemistry, vol. 57, No. 22, Nov. 26, 2014.

Galien et al., "4-Week Treatment of Rheumatoid Arthritis Patients with the JAK1-Selective Inhibitor Fgotinib (GLPG0634) Changes Lipid Profile with a Preferential Increase in HDL," Retrieved form the Internet:URL:http://acrabstrats.org/abstract/4-week-treatment-of-rheumatoidarthritis-patient-s-with-the-jak1-selective-inhibitor-filgotinib-glpg0634-changes-lipid-profile-withapreferential-increase-in-hdl/ [retrieved on May 13, 2016].

(Continued)

*Primary Examiner* — Sarah Pihonak
*Assistant Examiner* — Jason Deck
(74) *Attorney, Agent, or Firm* — Arent Fox LLP

(57) ABSTRACT

The present invention discloses compounds according to Formula (I): or a pharmaceutically acceptable salt thereof, or a solvate or the salt of a solvate thereof, pharmaceutical compositions comprising the same, and methods of treatment using the same, for use in the prophylaxis and/or treatment of cardiovascular disorders and/or dyslipidemia, by administering the compound according to Formula (I).

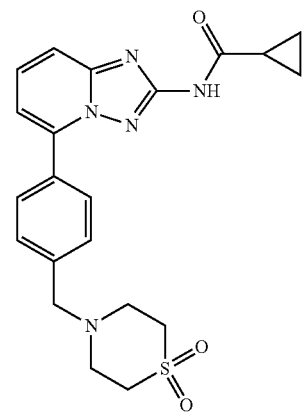

(I)

33 Claims, 31 Drawing Sheets

(56) References Cited

OTHER PUBLICATIONS

Schwartz et al., "Type I/II cytokines, JAKs, and new strategies for treating autoimmune diseases," Nature Reviews Rheumatology, vol. 12, No. 1, Dec. 3, 2015.
Aletaha et al., 2010 Rheumatoid Arthritis Classification Criteria, Arthritis & Rheumatism, vol. 62, No. 9, pp. 2569-2581 (Sep. 2010).
Allain et al., Enzymatic Determination of Total Serum Cholesterol, Clin. Chem., vol. 20, No. 4, pp. 470-475 (1974).
Barter, HDL-C: Role as a risk modifier, Atheroscler. Supp., vol. 12, No. 3, pp. 267-270 (2011).
Chait et al., Thematic review series: The Immune System and Atherogenesis. Lipoprotein-associated inflammatory proteins: markers or mediators of cardiovascular disease?, J. Lipid Res., vol. 46, No. 3, pp. 389-403 (2005).
Chapman, Therapeutic elevation of HDL-cholesterol to prevent atherosclerosis and coronary heart disease, Pharmacol. Ther., vol. 111, No. 3, pp. 893-908 (2006).
Daniella M. Schwartz et al: "Type I/II cytokines, JAKs, and new strategies for treating autoimmune diseases", Nature Reviews Rheumatology, vol. 12, No. 1, Dec. 3, 2016, pp. 25-36.
Eda et al., Development of a new microparticle-enhanced turbidimetric assay for C-reactive protein with superior features in analytical sensitivity and dynamic range, J. Clin. Lab. Anal., vol. 12, No. 3, pp. 137-144 (1998).
Fransen et al., Rheumatoid Arthritis Measures: Disease Activity Score (DAS), Disease Activity Score-28 (DAS28), Rapid Assessment of Disease Activity in Rheumatology (RADAR), and Rheumatoid Arthritis Disease Activity Index (RADAI), Arthritis & Rheumatism(Arthritis Care & Research), vol. 49, No. 5S, pp. S214-S224 (Oct. 3, 2003).
Friedwald et al., Estimation of the Concentration of Low-Density Lipoprotein Cholesterol in Plasma, Without Use of the Preparative Ultracentrifuge, Clinical Chemistry, vol. 18, No. 6, pp. 499-502 (1972).
Kumar et al., Cardiovascular disease "the silent killer in rheumatoid arthritis," Clinical Medicine, vol. 8, No. 4, pp. 384-387 (Aug. 2018).
Mackness et al., Low Paraoxonase Activity Predicts Coronary Events in the Caerphilly Prospective Study, Circulation, vol. 107, No. 2, pp. 2775-2779 (2003).
Millán et al., Lipoprotein ratios: Physiological significance and clinical usefulness in cardiovascular prevention, Vascular Health and Risk Management, vol. 5, pp. 757-765 (Nov. 20, 2009).
Nam et al., Search for an Optimal Atherogenic Lipid Risk Profile: From the Framingham Study, The American Journal of Cardiology, vol. 97, No. 3, pp. 372-375 (2006).
Navarro-Millán et al., Changes in Lipoproteins Associated With Methotrexate Therapy or Combination Therapy in Early Rheumatoid Arthritis: Results From the Treatment of Early Rheumatoid Arthritis Trial, Arthritis & Rheumatism, vol. 65, No. 6, pp. 1430-1438 (Jun. 2013).
Nilsson, CRP-Marker or Maker of Cardiovascular Disease?, Arterioscler. Thromb., vol. 25, No. 8, pp. 1527-1528 (2005).
O'Shea et al., Back to the Future: Oral targeted therapy for RA and other autoimmune diseases, Nat. Rev. Rheumatol., vol. 9, No. 3, pp. 173-182 (Mar. 2013).
O'Shea et al., JAK and STAT Signaling Molecules in Immunoregulation and Immune-Mediated Disease, Immunity Review, vol. 36, No. 4, pp. 542-550 (Apr. 20, 2012).
Price et al., Development and validation of a particle-enhanced turbidimetric immunoassay for C-reactive protein, Journal of Immunological Methods, vol. 99, No. 2, pp. 205-211 (1987).
Rene Galien et al. : "4-Week Treatment of Rheumatoid Arthritis patients with the JAK1-selective inhibitor Filgotinib (GLPG0634) Changes lipid profile with a preferential increase in HDL", Sep. 29, 2015, Abstract Number: 1681 of 2015 ACR/ARHP Annual Meeting.
Ridker et al., Comparison of C-Reactive Protein and Low-Density Lipoprotein Cholesterol Levels in the Prediction of First Cardiovascular Events, N. Engl. J. Med., vol. 347, No. 20, pp. 1557-1565 (Nov. 14, 2002).
Rifai et al., Measurement of low-density-lipoprotein cholesterol in serum: a status report, Clin. Chem., vol. 38, No. 1, pp. 150-160 (1992).
Robertson et al., Changes in lipid levels with inflammation and therapy in RA: a maturing paradigm, Nature Reviews Rheumatology, vol. 9, No. 9, pp. 513-523 (2013).
Sipponen et al., Endoscopic evaluation of Crohn's disease activity: comparison of the CDEIS and the SES-CD, Inflamm. Bowel Dis., vol. 16, No. 16, pp. 2131-2136 (Dec. 2010).
Song et al., Low-Density-Lipoprotein Particle Size Predicts a Poor Outcome in Patients with Atherothrombotic Stroke, J. Clin. Neurol., vol. 11, No. 1, pp. 80-86 (2015).
Wells et al., Validation of the 28-joint Disease Activity Score (DAS28) and European League Against Rheumatism response criteria based on C-reactive protein against disease progression in patients with rheumatoid arthritis, and comparison with the DAS28 based on erythrocyte sedimentation rate, Ann. Rheum. Dis., vol. 68, No. 6, pp. 954-960 (2009).

* cited by examiner

METHODS FOR THE TREATMENT OF CARDIOVASCULAR DISORDERS

FIELD OF THE INVENTION

The present invention relates to a compound for use in the prophylaxis and/or treatment of cardiovascular disorders and/or dyslipidemia. In particular, the compound of the invention inhibits JAK, a family of tyrosine kinase. More particularly, the compound inhibits JAK1. The present invention also provides methods for the prophylaxis and/or treatment of cardiovascular disorders and/or dyslipidemia by administering the compound of the invention.

BACKGROUND OF THE INVENTION

Cholesterol is a lipid molecule, which is biosynthesized by animal cells or absorbed from food such as egg yolks, meat, poultry, fish, and dairy products. It is an essential component to cell membranes and it is required for cell integrity and fluidity. In particular, cholesterol is a precursor for the biosynthesis of steroid hormones, bile acid and vitamin D.

Cholesterol is transported through bloodstream as lipoproteins, which are made of lipids on the inside and proteins on the outside. These lipoproteins are divided into five major lipoproteins: chylomicrons, very low-density lipoproteins (VLDL), intermediate-density lipoproteins (IDL), low-density lipoproteins (LDL) and high-density lipoproteins (HDL).

Amongst those lipoproteins, LDL is often referred to as "bad" cholesterol, since high LDL level leads to a buildup of cholesterol deposits in arteries. On the other hand, HDL is considered as "good" cholesterol, because it carries cholesterol from all parts of the body back to the liver, which in turn eliminates the excess cholesterol from the body, therefore HDL has anti-atherogenic properties.

High blood cholesterol or hypercholesterolemia is a condition characterized by an excess of cholesterol in blood. Although, this condition usually has no signs or symptoms, individuals with high blood cholesterol have a greater chance to develop cardiovascular disorders (cardiovascular disorder). Guidelines regarding cholesterol levels are available recommending [total cholesterol] within 150-199 mg/dL (3.88-5.15 mmol/L), [LDL] levels below 130 mg/dL (<3.36 mmol/L), and [HDL] above 40 mg/dL (>1.04 mmol/L) (*The Merck Manual of Diagnosis and Therapy*, 2011).

According to the World Health Organization (WHO), cardiovascular disorder is the leading cause of death globally, with an estimated 17.5 million deaths in 2012.

One particular type of cardiovascular disorder is atherosclerosis, which is a condition where a plaque made up of cholesterol, fat, calcium, and other blood components builds up inside arteries, in particular in coronary arteries. Over time, this plaque grows and hardens, thus limiting blood circulation and oxygen supply to the heart leading eventually to angina or heart attack, which may be fatal.

Therefore, reducing [LDL] levels and increasing [HDL] levels would be beneficial in reducing cardiovascular disorder (Barter, 2011; Chapman, 2006).

In rheumatoid arthritis (RA) patients, it has been observed that the [total cholesterol] level is lower. It could therefore be expected that low cholesterol levels would render RA patients less subject to cardiovascular disorder. However, against all expectations, these same patients having a high inflammatory burden were found to be at heightened cardiovascular disorder risk. This heightened cardiovascular disorder risk with low [LDL] and cholesterol levels has been branded the 'RA-lipid paradox' (Robertson et al., 2013). In particular, it has been observed that not only do RA patients suffer from low lipid levels, but in addition the [LDL] proportion is higher compared to [HDL] (Kumar and Armstrong, 2008).

With the numerous therapies being developed to treat RA, many clinical studies have been conducted, and the relationship between inflammation and lipid profile has been investigated, but remains unclear. In particular, upon treatment of inflammation, it was observed that lipid levels returned to normality, albeit with a higher [LDL] proportion compared to [HDL] (Navarro-Millán et al., 2013), therefore potentially increasing the cardiovascular disorder risk again.

The association between moderately elevated CRP levels and an increased risk for development of cardiovascular disease is well established (Nilsson, 2005). Moreover, the rise in blood cholesterol in patients with inflammation after treatment has been argued to be associated with the resolution of inflammation and reduction in CRP. For this reason, CRP has emerged as an interesting and potentially clinically useful marker for increased cardiovascular risk (Nilsson, 2005; Ridker et al., 2002). Guidelines regarding the levels of CRP associated to the rise in cardiovascular disorders have also been issued setting normal CRP levels at <0.5 mg/dL (*The Merck Manual of Diagnosis and Therapy*, 2011). Similarly and independently, heightened [LDL] has been identified as a predictor for cardiovascular disease (Song et al., 2015). Therefore, it would be particularly beneficial if anti-inflammatory therapy would not only increase abnormally low cholesterol levels in patients, but if such therapy would do so with a preferential increase in [HDL], relative to [LDL] and [total cholesterol].

In addition to CRP, additional biomarkers which may play a role in cardiovascular disorders, particularly atherogenesis, have been identified in the recent years (Chait et al., 2005). Such biomarkers include Serum Amyloid A (SAA), secretory phospholipase $A_2$ (sPLA$_2$), Apolipoprotein A-I (ApoA-1), or paraoxonase 1 (PON1).

SAA is carried by lipoproteins, in particular HDL, and its levels are markedly raised during acute inflammatory episodes, but also in conditions associated with increased cardiovascular risks including obesity, insulin resistance, diabetes, metabolic syndrome, and RA. High levels of SAA may contribute to the stimulation of monocyte adhesion and chemotaxis into the artery wall cells, and increased delivery of cholesterol to artery cell walls, thus suggesting that SAA is a mediator of atherosclerosis and a marker for cardiovascular disorders (Chait et al., 2005).

sPLA$_2$ is present in artery walls, and hydrolyses phospholipids in both LDL and HDL; but it also converts LDL into particles associated with increased risk of cardiovascular disorders (Chait et al., 2005).

ApoA-I is the major component of HDL, therefore, low levels of ApoA-I are correlated to low HDL levels, and thereby higher cardiovascular risks (Chait et al., 2005).

PON1 belongs to the paraoxonase family, which protects cells from damages by organophosphate toxins, and is synthesized by the liver, from where it is transported into the plasma by HDL. In turn, HDL associated PON1 inhibits lipid peroxidation, which may prevent atherosclerosis (Chait et al., 2005).

In fighting RA, Janus kinases (JAKs) inhibitors have been developed. JAKs are cytoplasmic tyrosine kinases that transduce cytokine signaling from membrane receptors to STAT transcription factors. Four JAK family members have been described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL (Vainchenker W. et al. (2008)).

The combination of genetic models and small molecule JAK inhibitor research revealed the therapeutic potential of inhibition of several JAKs.

JAK1 is a target in the immuno-inflammatory disease area. JAK1 heterodimerizes with the other JAKs to transduce cytokine-driven pro-inflammatory signaling. Therefore, inhibition of JAK1 is of interest for immuno-inflammatory diseases with pathology-associated cytokines that use JAK1 signaling, such as IL-6, IL-4, IL-9, IL-15, IL-21, or IFNgamma, as well as for other diseases driven by JAK-mediated signal transduction. The compound according to Formula I, cyclopropanecarboxylic acid {5-[4-(1,1-dioxo-thiomorpholin-4-ylmethyl)-phenyl]-[1,2,4]triazolo[1,5-a]pyridin-2yl}-amide (Compound 1), is disclosed in WO2010/149769 (Menet and Smits, 2010) and has the chemical structure shown below:

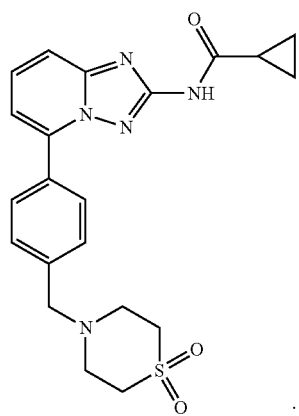

Compound 1 is a JAK inhibitor, more particularly a JAK1 inhibitor, and useful in the treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons.

However, whereas JAK inhibitors are useful and effective molecules in the treatment of RA, or inflammatory bowel disorders (IBD) one drawback to the use of these compounds that has been reported is hypercholesterolemia (O'Shea et al., 2013; O'Shea and Plenge, 2012).

The identification and development of new agents for the treatment of cardiovascular disorders and/or dyslipidemia would be highly desirable, both for patients suffering from inflammatory disorders, e.g. RA patients, and non-inflamed patients alike. In particular, there is a need for anti-inflammatory therapies which not only restore abnormal lipid profile levels in patients to normal recommended values as defined herein, but which do so with a preferential increase in [HDL], relative to [LDL].

SUMMARY OF THE INVENTION

The present invention provides the compound of the invention according to Formula I (Compound 1) for use in the prophylaxis and/or treatment of cardiovascular disorders and/or dyslipidemia. In particular, the compound of the invention may act as an inhibitor of JAK, and more particularly of JAK1.

Furthermore, the present invention provides pharmaceutical compositions comprising the compound according to Formula I (Compound 1) for use in the prophylaxis and/or treatment of cardiovascular disorders and/or dyslipidemia.

The present invention also provides methods for the production of these pharmaceutical compositions of the invention and methods for the treatment and/or prophylaxis of cardiovascular disorders by administering the pharmaceutical compositions of the invention.

When Compound 1 was administered orally in humans, an unexpected change in the lipid profile was observed.

Without being limited by theory, the inventors believe that this effect could be associated with Compound 1's particular kinase selectivity profile, particular towards JAK1, since the same effect is not shown by other JAK inhibitors that have been tested.

For example, in the controlled clinical trials of Tofacitinib, a JAK inhibitor, dose-related elevations in lipid parameters, including [total cholesterol], [LDL], and [HDL], were observed. In particular the following changes in lipid parameters during the first 3 months of exposure in the controlled clinical trials were as follows: mean [LDL] increased by 15% in the 5 mg twice daily arm and 19% in the 10 mg twice daily arm; mean [HDL] increased by 10% in the 5 mg twice daily arm and 12% in the 10 mg twice daily arm, whereas mean [LDL]/[HDL] ratios were essentially unchanged in patients, (FDA Application No. (NDA) 203214, summary review 203214Orig1s000), thus raising initial lipid levels, but with a unfavorable [HDL] vs [LDL] ratio.

In contrast, whereas Compound 1 raised the low [total cholesterol] levels, an unexpected disproportionate rise in blood of [HDL] vs [LDL] was observed. In particular, [HDL] levels of 5-23% compared to initial levels were seen. Moreover, this rise in [HDL] was substantially higher than the corresponding increases in [LDL] levels. In particular between 1.1 and 4 fold higher increases in [HDL] vs. [LDL] were seen.

Moreover, it has been coined in that the [total cholesterol]/[HDL] ratio otherwise known as the 'atherogenic index', has a great predictive capacity of cardiovascular risks (Millán et al., 2009). Accordingly, for example, in men a [total cholesterol]/[HDL] ratio of 1.68-4.21 resulted in a cardiovascular risk increase of 11-16%, a [total cholesterol]/[HDL] ratio of 4.22-5.53 resulted in a cardiovascular risk increase of 19-29%, and a [total cholesterol]/[HDL] ratio of 5.54-18.1 resulted in a cardiovascular risk increase of 26-33% (Nam et al., 2006).

Typically, in a recent treatment study with Tofacitinib, a JAK inhibitor for 6 weeks at a dose of 10 mg bid in RA patient, the atherogenic index was unchanged before and after treatment at about 3.5 (Charles-Schoeman et al., 2015) thus leaving the patient at an increased cardiovascular risk before and after treatment. In contrast, upon administration of Compound 1 at doses ranging from 50 mg to 200 mg (once or twice daily) for a period of at least 4 weeks resulted in a drop of the atherogenic index, thereby reducing the initial cardiovascular risk.

Furthermore, this effect was sustained over at least 12 weeks, and at least 24 weeks and were observed over a dose range of 50-200 mg administered either twice daily (b.i.d) or once a day (q.d.).

Additionally, this effect was seen both in healthy volunteers, and patients suffering from inflammatory diseases (for example RA and Crohn's disease).

Therefore Compound 1 would be particularly advantageous in preventing and/or treating cardiovascular disorder, and the object of the present invention is Compound 1 for use in the prophylaxis and/or treatment of cardiovascular disorder and/or dyslipidemia.

Accordingly, in a first aspect of the invention, the compound of the invention having a Formula (I):

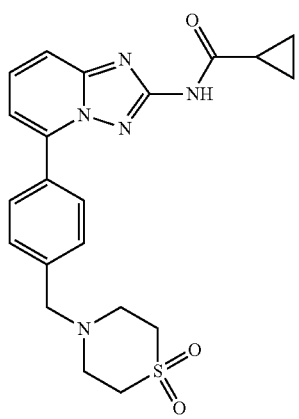

is provided for use is the prophylaxis and/or treatment of cardiovascular disorders and/or dyslipidemia.

In a particular aspect is provided the compound of the invention for use in the prophylaxis and/or treatment of chronic cardiovascular disorders. In a more particular aspect, the cardiovascular disorder is atherosclerosis.

In a particular aspect is provided the compound of the invention for use in the prophylaxis and/or treatment of chronic dyslipidemia. In a more particular aspect, the cardiovascular disorder is hypolipidemia.

In a particular aspect is provided the compound of the invention for use in the prophylaxis and/or treatment of cardiovascular disorders in patients not suffering from RA as measured by the DAS28(CRP) score method (Wells et al., 2008), wherein the DAS28(CRP) value is less than 2.6.

In another particular aspect is provided the compound of the invention for use in the prophylaxis and/or treatment of cardiovascular disorders in RA patients, wherein the treatment extends for longer than 4 weeks.

In yet another aspect is provided the compound of the invention for use in the prophylaxis and/or treatment of cardiovascular disorders in IBD patients. In a particular aspect is provided the compound of the invention for use in the prophylaxis and/or treatment of cardiovascular disorders in ulcerative colitis and/or Crohn's disease patients. In a more particular aspect, is provided the compound of the invention for use in the prophylaxis and/or treatment of cardiovascular disease in Crohn's disease patients.

The present invention also provides pharmaceutical compositions comprising a compound of the invention, and a suitable pharmaceutical carrier, excipient or diluent for use in the prophylaxis and/or treatment of cardiovascular disorders. In a more particular aspect, the cardiovascular disorder is atherosclerosis.

The present invention also provides pharmaceutical compositions comprising a compound of the invention, and a suitable pharmaceutical carrier, excipient or diluent for use in the prophylaxis and/or treatment of dyslipidemia. In a more particular aspect, the cardiovascular disorder is hypolipidemia.

In a further particular aspect, the pharmaceutical composition may additionally comprise further therapeutically active ingredients suitable for use in combination with the compounds of the invention. In a more particular aspect, the further therapeutically active ingredient is an agent for the treatment of cardiovascular disorders.

In a further particular aspect, the pharmaceutical composition may additionally comprise further therapeutically active ingredients suitable for use in combination with the compounds of the invention. In a more particular aspect, the further therapeutically active ingredient is an agent for the treatment of dyslipidemia.

Moreover, the compounds of the invention, useful in the pharmaceutical compositions and treatment methods disclosed herein, are pharmaceutically acceptable as prepared and used.

In a further aspect of the invention, this invention provides a method for the prophylaxis and/or treatment of cardiovascular disorders and/or dyslipidemia in a mammal in need thereof, in particular humans, which method comprises administering an effective amount of the pharmaceutical composition or compounds of the invention as described herein.

In another further aspect of the invention, this invention provides a method of decreasing the risk of cardiovascular risk in a mammal, in particular humans, which method comprises administering an effective amount of the pharmaceutical composition or compounds of the invention as described herein.

In yet a further aspect of the invention, this invention provides a method of increasing [HDL] blood levels in in a mammal in need thereof, in particular humans, which method comprises administering an effective amount of the pharmaceutical composition or compounds of the invention as described herein. In a particular aspect, the [HDL] compared to prior to the treatment level is increased by at least 5%, at least 10%, at least 15%, at least 20%, and/or at least 23%.

In yet a further aspect of the invention, this invention provides a method of decreasing the atherogenic index in a mammal in need thereof, in particular humans, which method comprises administering an effective amount of the pharmaceutical composition or compounds of the invention as described herein. In a particular aspect, the atherogenic index compared to prior to the treatment level is decreased by at least 0.2, by at least 0.3, and/or at least 0.35.

In additional aspects, this invention discloses methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

BRIEF DESCRIPTION OF THE DRAWINGS

FIG. 11. Shows the mean percentage change in [Total Cholesterol], [HDL] and [LDL] vs baseline compared to placebo in Study 1 in RA patients upon administration of Compound 1 (dosed as [Compound 1:HCl:3H$_2$O] after 24 weeks treatment. At week 12, the subjects on placebo who did not achieve at least a 20% improvement in swollen joint count (SJC66) and tender joint count (TJC68) were re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

FIG. 12. Shows the mean percentage change vs baseline in [LDL] level in Study 1 in RA patients upon administration of Compound 1 (dosed as [Compound 1:HCl:3H$_2$O] after 24 weeks treatment. At week 12, the subjects on placebo who did not achieve at least a 20% improvement in swollen joint count (SJC66) and tender joint count (TJC68) were re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

FIG. 13. Shows the mean percentage change vs baseline in [HDL] level in Study 1 in RA patients upon administration of Compound 1 (dosed as [Compound 1:HCl:3H$_2$O] after 24 weeks treatment. At week 12, the subjects on placebo who did not achieve at least a 20% improvement in swollen joint count (SJC66) and tender joint count (TJC68) were re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

FIG. 14. Shows the mean percentage change vs baseline in atherogenic index in Study 1 in RA patients upon administration of Compound 1 (dosed as [Compound 1:HCl:$3H_2O$] after 24 weeks. At week 12, the subjects on placebo who did not achieve at least a 20% improvement in swollen joint count (SJC66) and tender joint count (TJC68) were re-randomized automatically to receive Compound 1 (dosed as a [Compound 1:HCl:$3H_2O$]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

FIG. 18 shows the mean % variation in the following groups: a) placebo switching to 100 mg q.d. at week 12 (filled diamonds), b) non-responders switching from 50 mg q.d. to 100 mg q.d. at week 12 (tilted crosses), c) continued 50 mg q.d. (filled triangles), d) continued 100 mg q.d. (100 mg, asterisks), and e) 200 mg q.d. (filled circles).

FIG. 19. Shows the decrease in the serum CRP level in mg/L in the patient population at the 1, 2, 4, 8, 12, 16, 20 and 24 week time points for each dose in Study 1. At Week 12, the subjects on placebo who did not achieve at least a 20% improvement in swollen joint count (SJC66) and tender joint count (TJC68) were re-randomized automatically to receive Compound 1 (dosed as a [Compound 1:HCl:$3H_2O$]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d. Subjects who switched treatment at week 12 were handled as if they discontinued at week 12 for the purpose of statistical analysis, whereas subjects in the other groups maintained their randomized treatment until Week 24. Consequently, the data reported from week 16 to week 24 only refers to the data for the subjects continuing on the same treatment course from week 0 to week 24.

Figure 21:
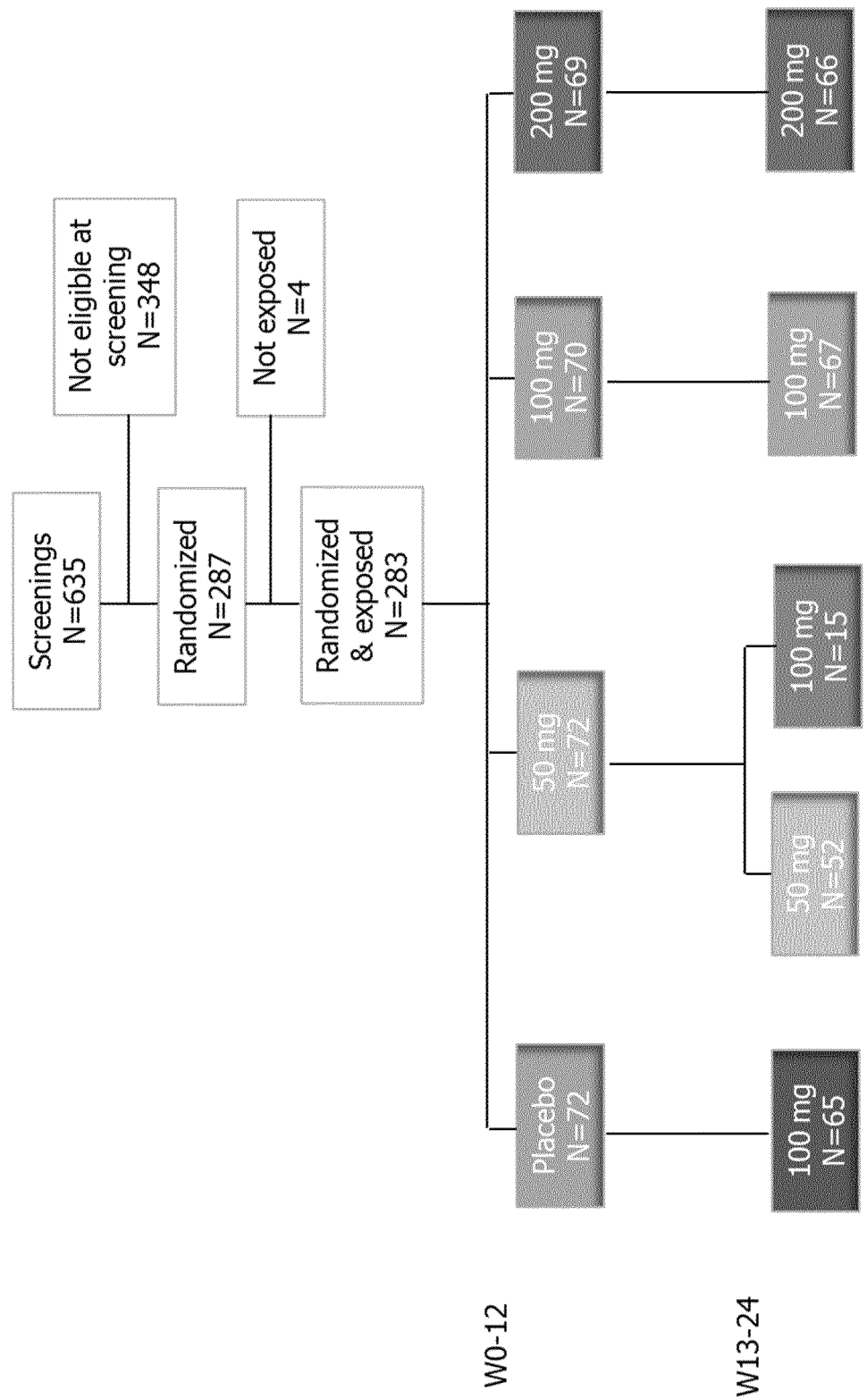

FIG. 21. Shows the patient distribution throughout Study 2 over the 24 weeks. From week 0 to 12, the patients were randomized and distributed within the following groups: a) placebo, b) 50 mg q.d., c) 100 mg q.d., and d) 200 mg q.d. At Week 12, all subjects on placebo and the subjects on the 50 mg dose who did not achieve at least a 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.

Figure 22:
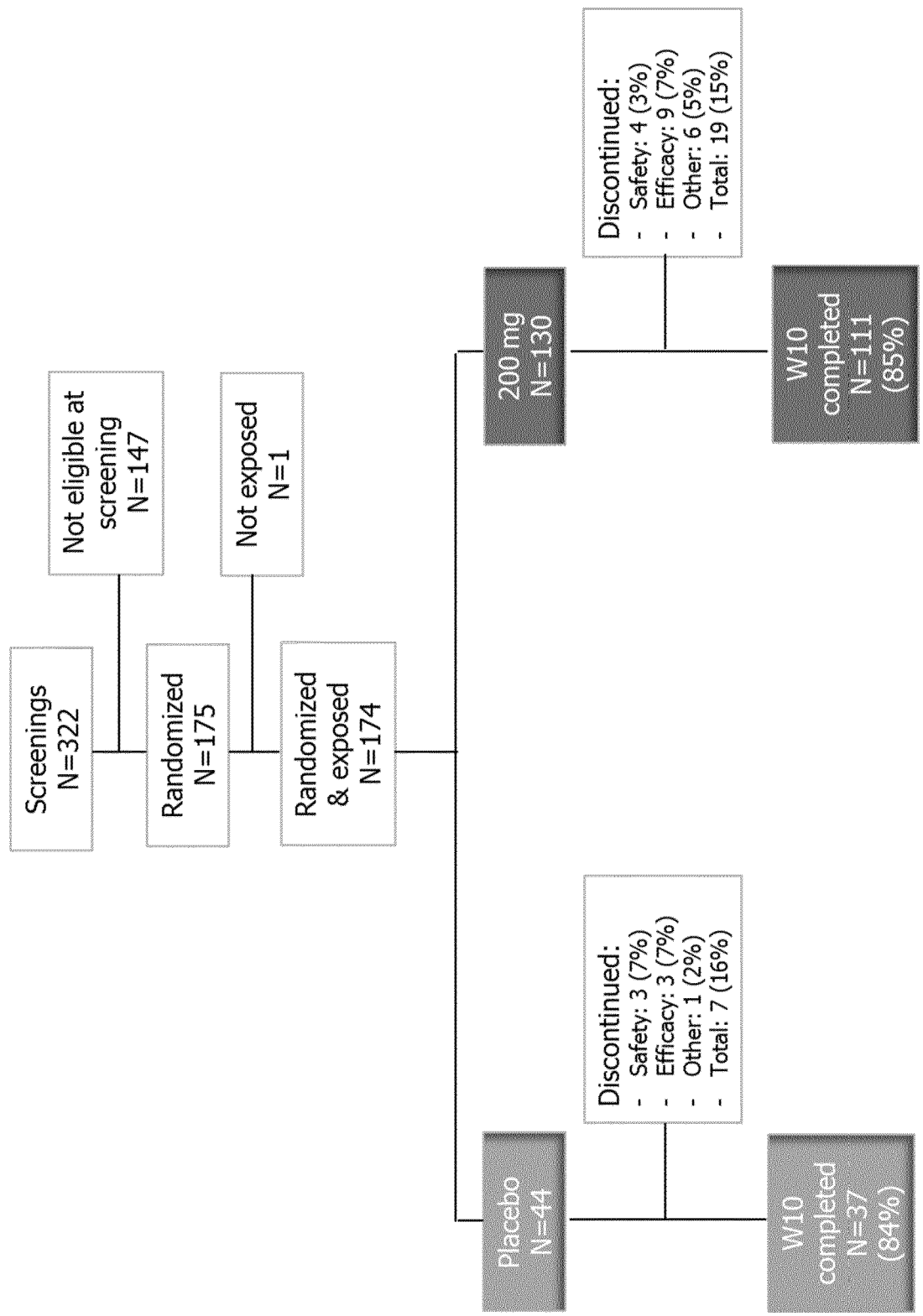

FIG. 22. Shows the patient distribution throughout Study 5 over 10 weeks. From week 0 to 10, the patients were randomized and distributed within the following groups: a) placebo, and b) 200 mg q.d.

Figure 23A:
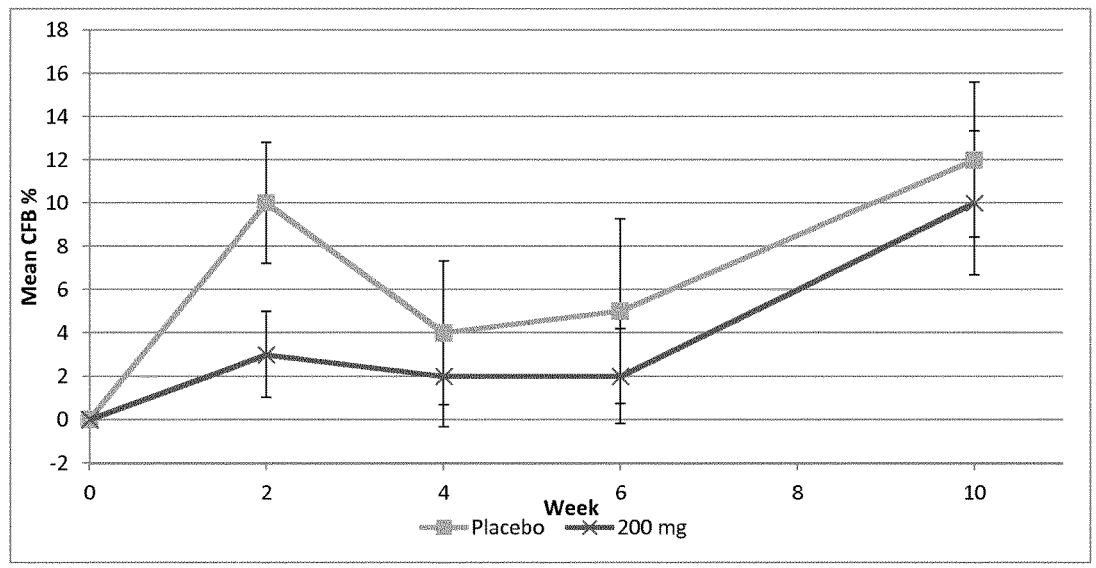
Figure 23B:
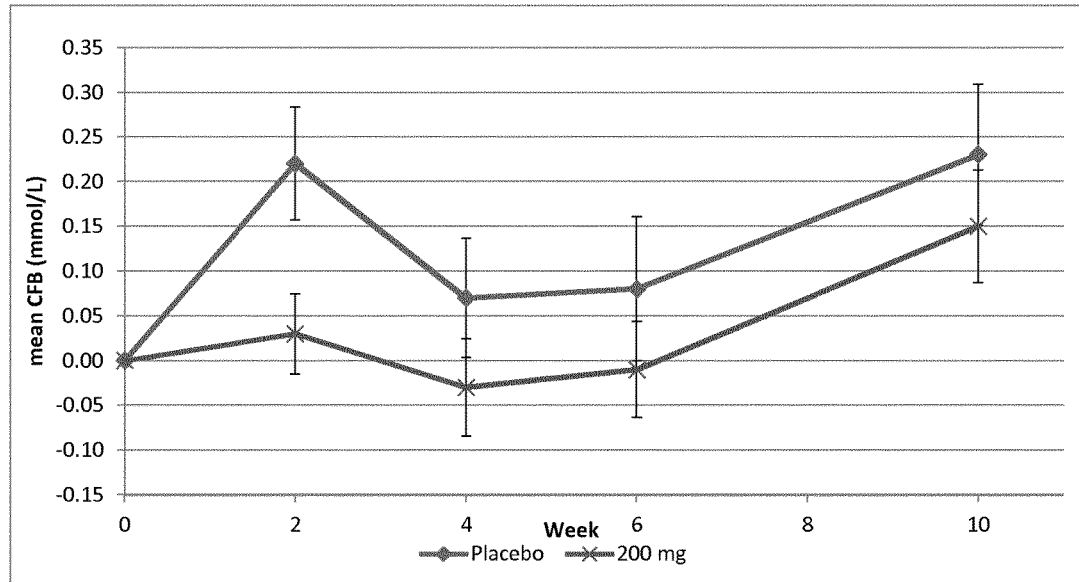

FIG. 23. Shows the change vs baseline (CFB) in [LDL] level in the patient population upon administration of Compound 1 (dosed as [Compound 1:HCl:3H$_2$O] at the 2, 4, 6, and 10 week time points in Study 5. FIG. 23A shows the mean % variation, and FIG. 23B shows the mean variation in mmol/L in the following groups: a) placebo (filled squares), and b) 200 mg q.d. (tilted crosses).

Figure 24A:
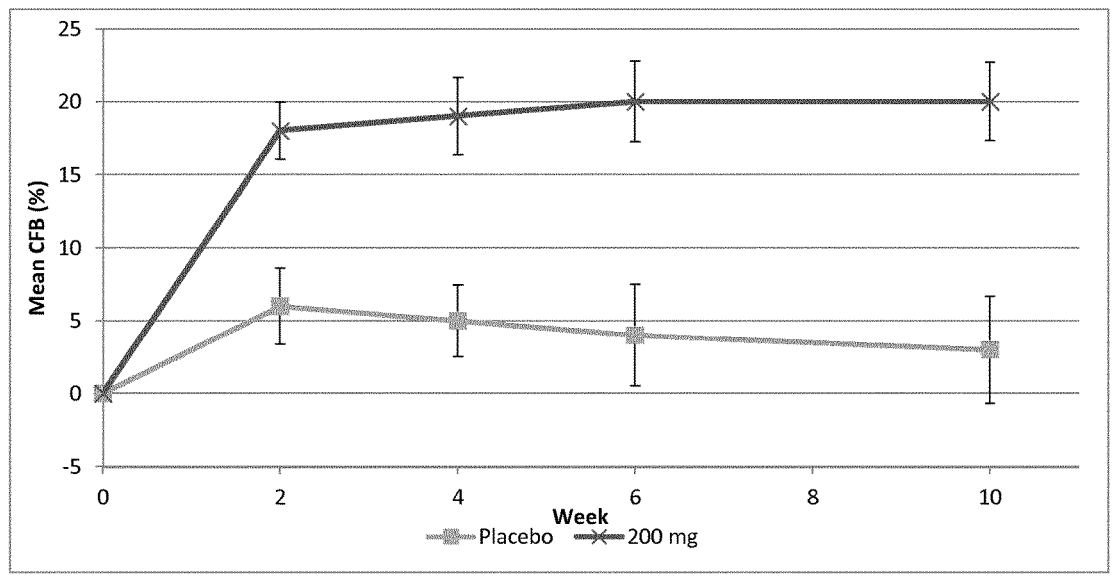
Figure 24B:
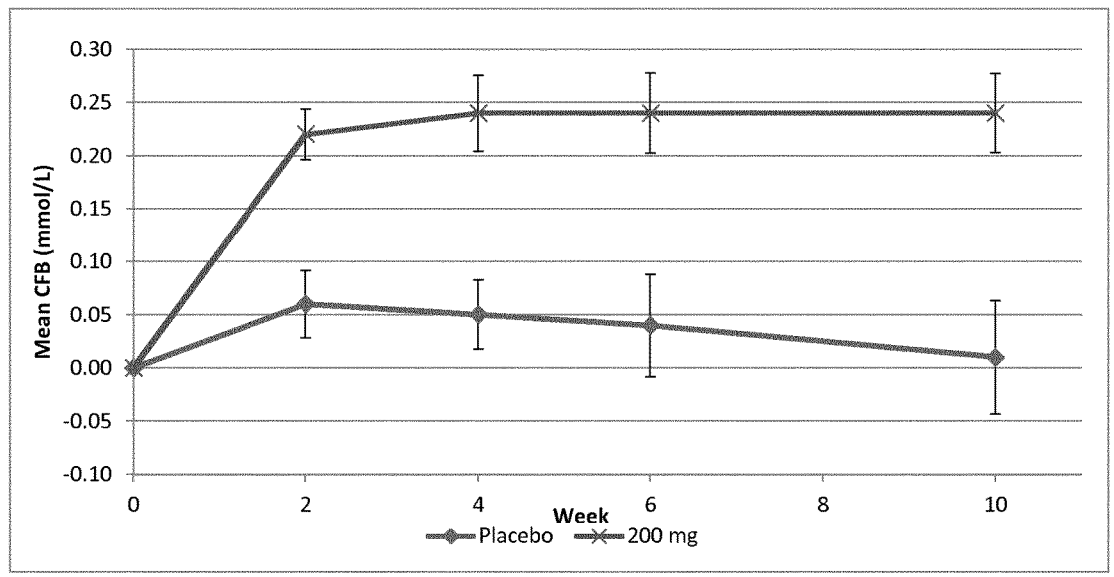

FIG. 24. Shows the change vs baseline (CFB) in [HDL] level in the patient population upon administration of Compound 1 (dosed as [Compound 1:HCl:3H$_2$O] at the 2, 4, 6, and 10 week time points in Study 5. FIG. 24A shows the mean % variation, and FIG. 24B shows the mean variation in mmol/L in the following groups: a) placebo (filled diamonds), and b) 200 mg q.d. (tilted crosses).

Figure 25A:
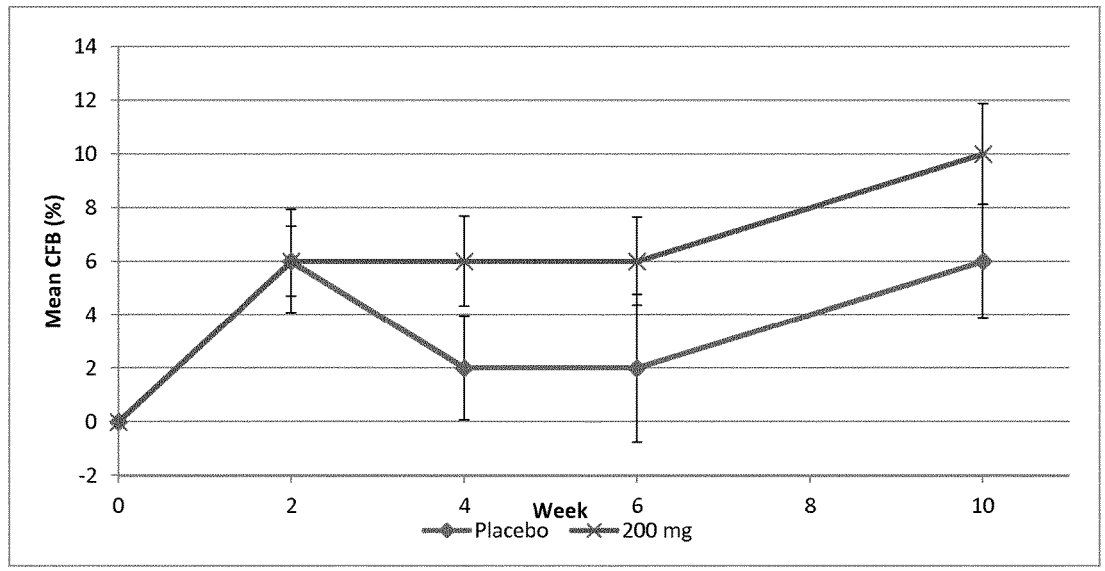
Figure 25B:
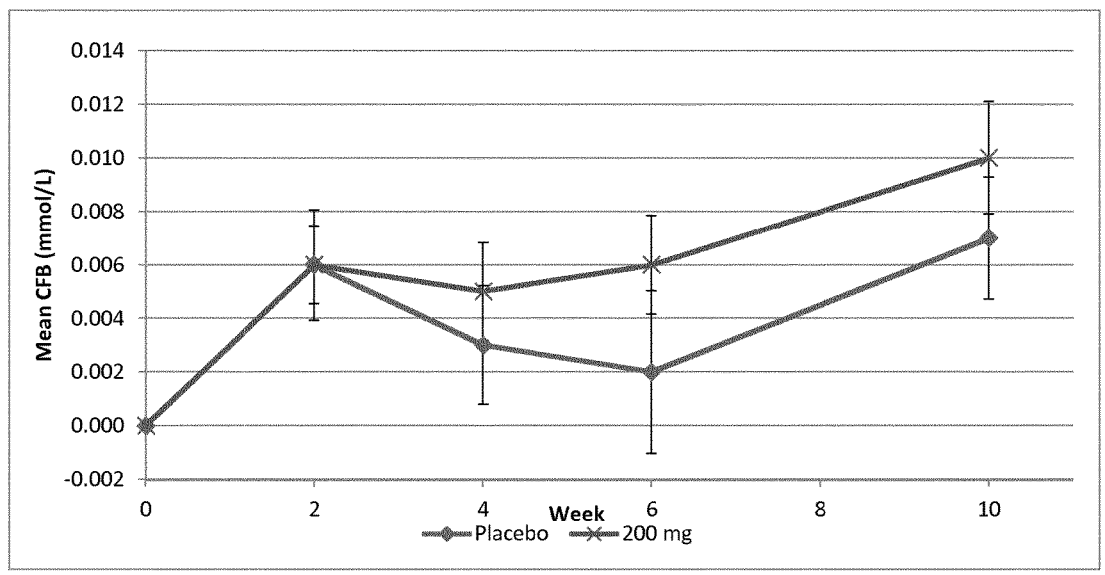

FIG. 25. Shows the change vs baseline in atherogenic index in the patient population upon administration of Compound 1 (dosed as [Compound 1:HCl:3H$_2$O] at the 2, 4, 6, and 10 weeks time points in Study 5. FIG. 25A shows the mean % variation, and FIG. 25B shows the mean variation in mmol/L in the following groups: a) placebo (filled diamonds), and b) 200 mg q.d. (tilted crosses).

Figure 26A:
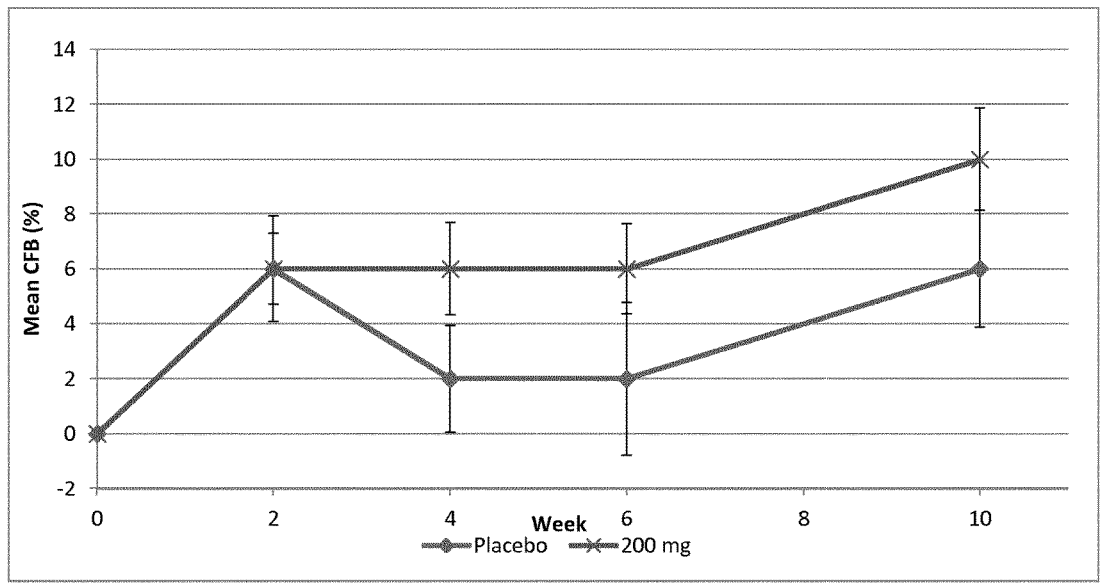
Figure 26B:
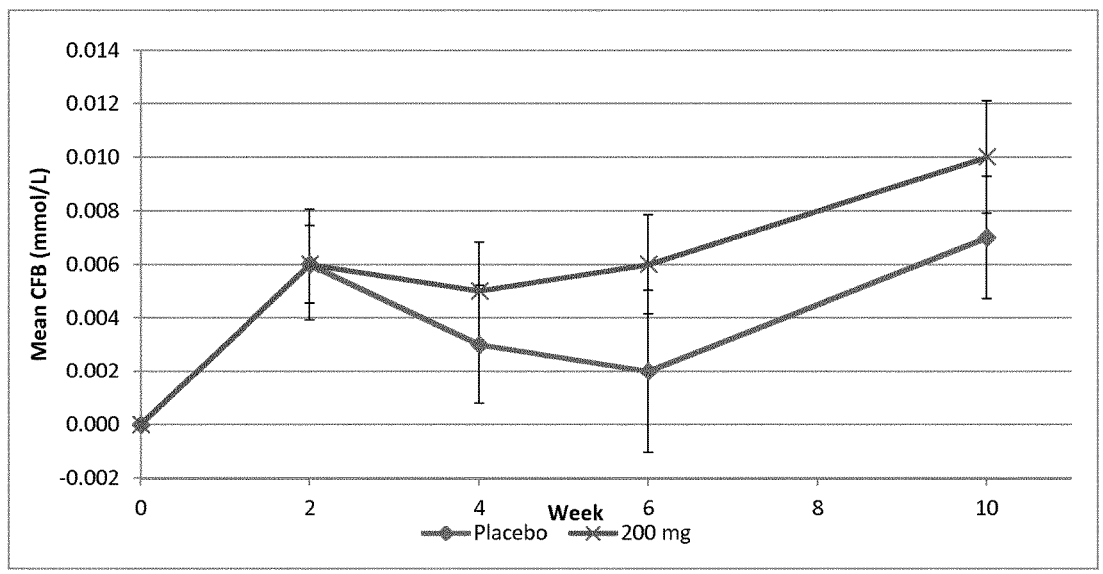

FIG. 26. Shows the change vs baseline in [Total cholesterol] level in the patient population upon administration of Compound 1 (dosed as [Compound 1:HCl:3H$_2$O] at the 2, 4, 6, and 10 weeks time points in Study 5. FIG. 26A shows the mean % variation, and FIG. 26B shows the mean variation in mmol/L in the following groups: a) placebo (filled diamonds), and b) 200 mg q.d. (tilted crosses).

Figure 27:
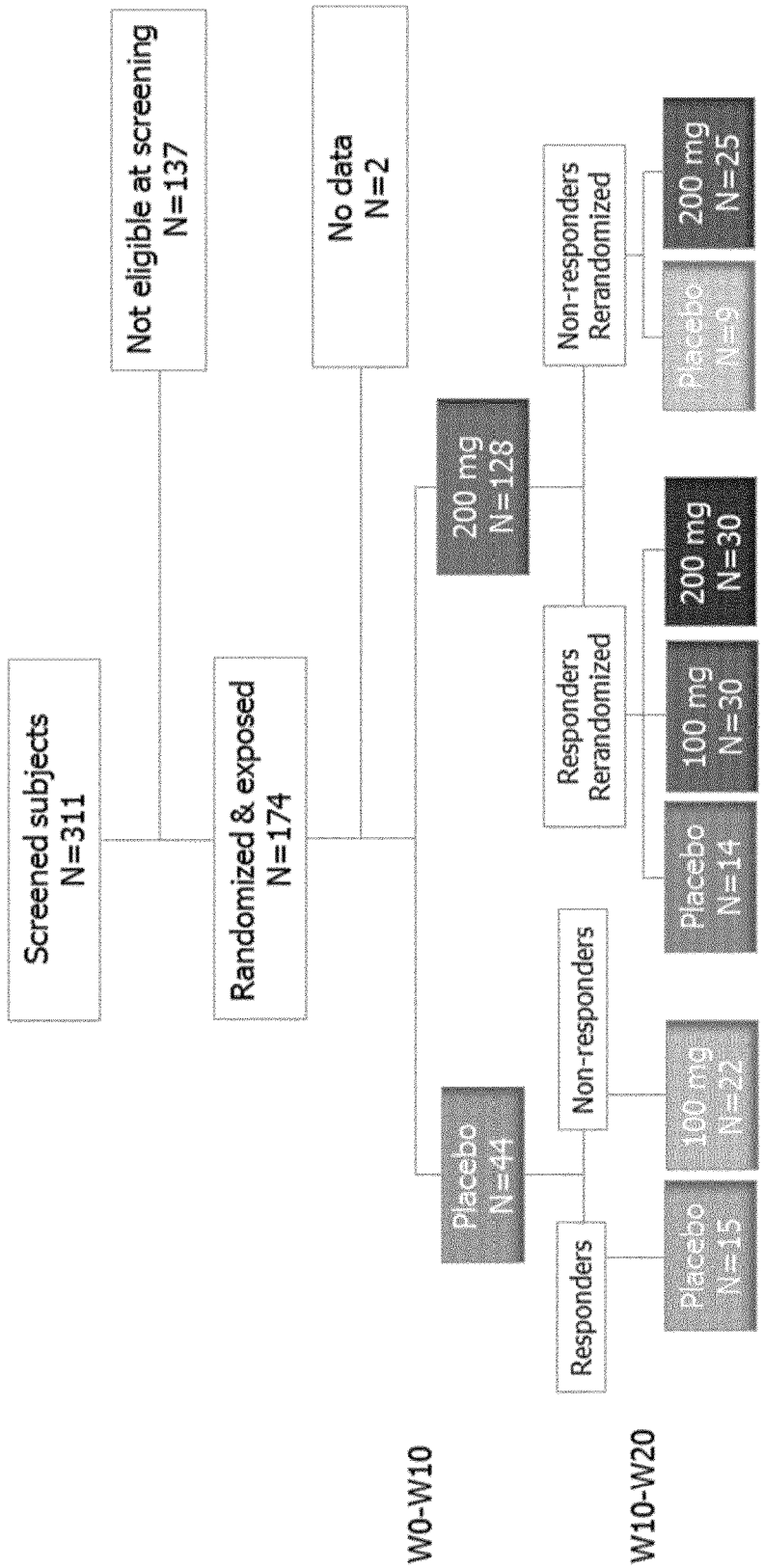

FIG. 27. Shows the patient distribution throughout Study 5 over 20 weeks. From week 0 to 10, the patients were randomized and distributed within the following groups: a) placebo, and b) 200 mg q.d. At week 10, patients are categorized as responders and non-responders. From the week 10 to week 20, a) the initial placebo responders are kept on placebo, and b) the initial placebo non-responders are put on a 100 mg q.d. dose regimen. In the initial 200 mg q.d. group, the responders are randomized between c) placebo, d) 100 mg q.d., e) 200 mg q.d. until week 20, whereas the non-responders are randomized between f) placebo, and g) 200 mg q.d. dose until week 20.

Figure 28A:
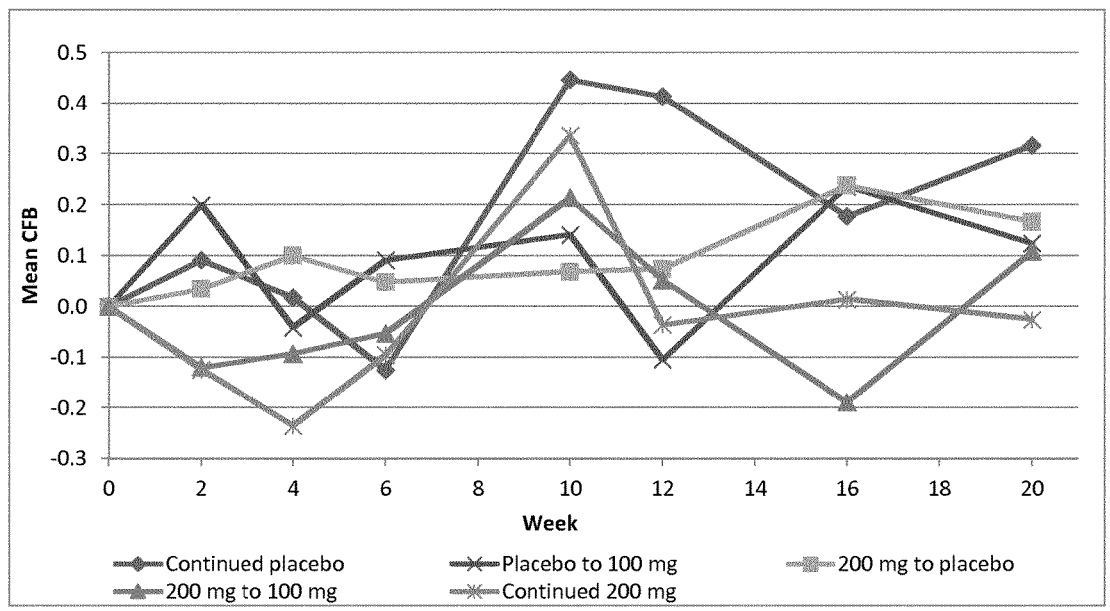
Figure 28B:
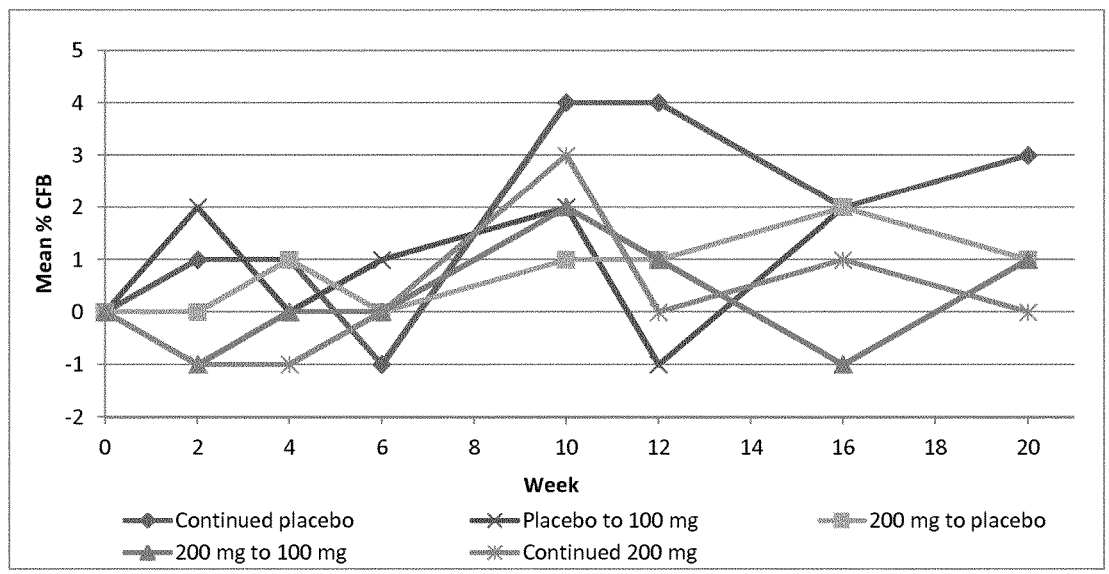

FIG. 28. Shows the change vs baseline (CFB) in [LDL] level in the patient population upon administration of Compound 1 (dosed as [Compound 1:HCl:3H$_2$O] over 20 weeks in Study 5. FIG. 28A shows the mean variation in mmol/L, and FIG. 28B shows the mean % variation in the following groups: a) continued placebo (filled diamonds), b) placebo switching to 100 mg q.d. at week 10 (tilted crosses), c) 200 mg swiching to placebo at week 10 (filled square), d) 200 mg switching to 100 mg at week 10 (filled triangles), e) and continued 200 mg q.d. (asterisk).

Figure 29A:
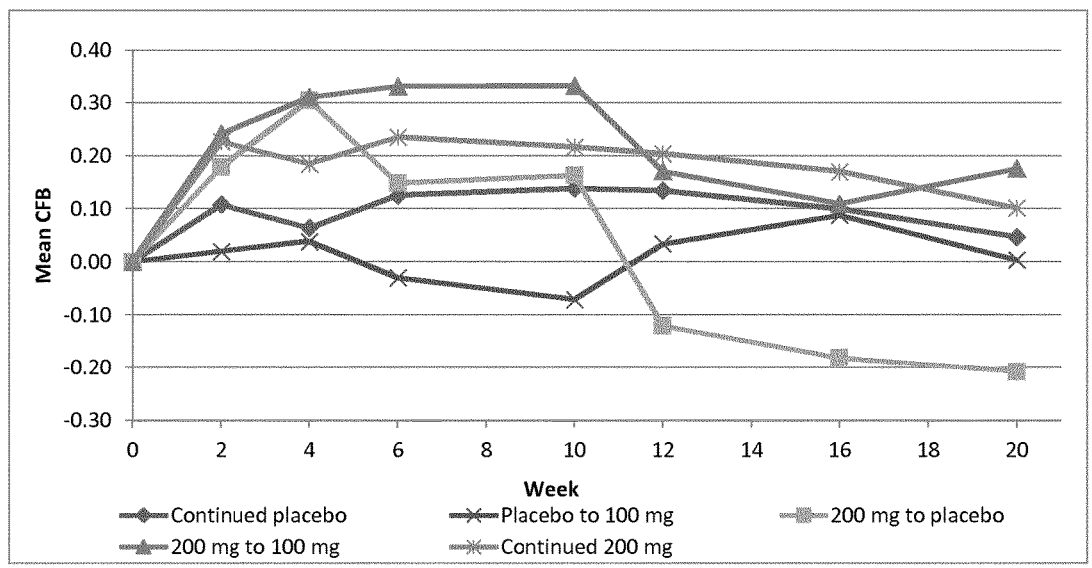
Figure 29B:
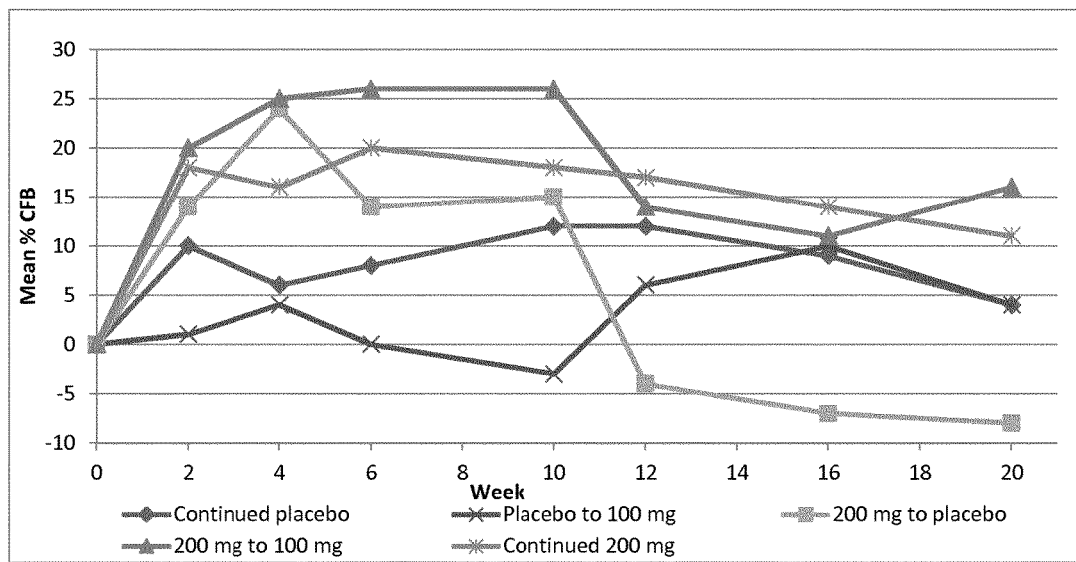

FIG. 29. Shows the change vs baseline (CFB) in [HDL] level in the patient population upon administration of Compound 1 (dosed as [Compound 1:HCl:3H$_2$O] over 20 weeks in Study 5. FIG. 29A shows the mean variation in mmol/L, and FIG. 29B shows the mean % variation in the following groups: a) continued placebo (filled diamonds), b) placebo switching to 100 mg q.d. at week 10 (tilted crosses), c) 200 mg swiching to placebo at week 10 (filled square), d) 200 mg switching to 100 mg at week 10 (filled triangles), e) and continued 200 mg q.d. (asterisk).

Figure 30A:
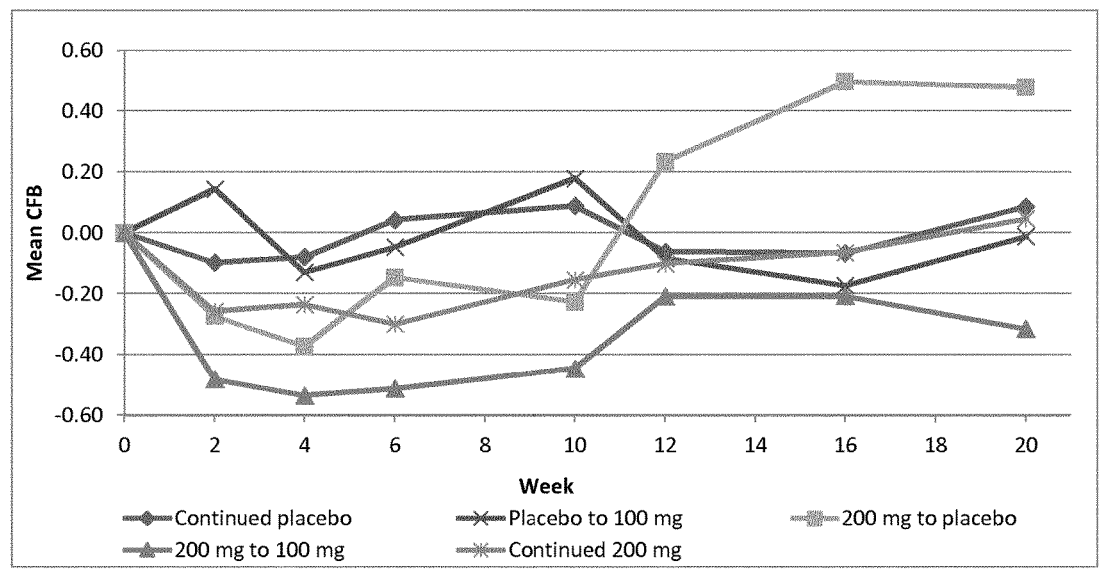
Figure 30B:
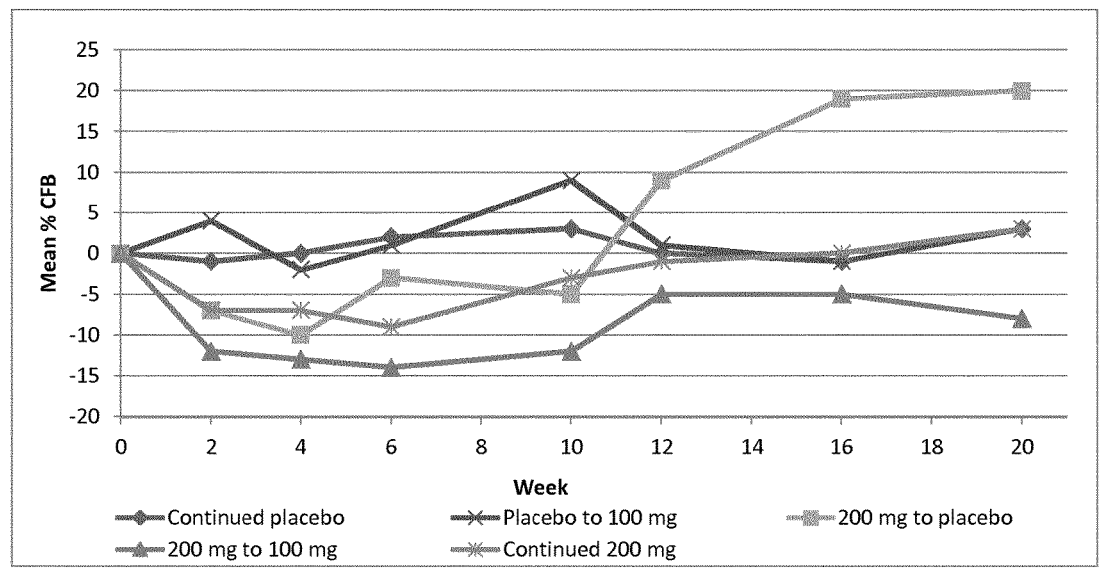

FIG. 30. Shows the change vs baseline in atherogenic index in the patient population upon administration of Compound 1 (dosed as [Compound 1:HCl:3H$_2$O] over 20 weeks in Study 5. FIG. 30A shows the mean variation in mmol/L, and FIG. 30B shows the mean % variation in the following groups: a) continued placebo (filled diamonds), b) placebo switching to 100 mg q.d. at week 10 (tilted crosses), c) 200 mg swiching to placebo at week 10 (filled square), d) 200 mg switching to 100 mg at week 10 (filled triangles), e) and continued 200 mg q.d. (asterisk).

Figure 31A:
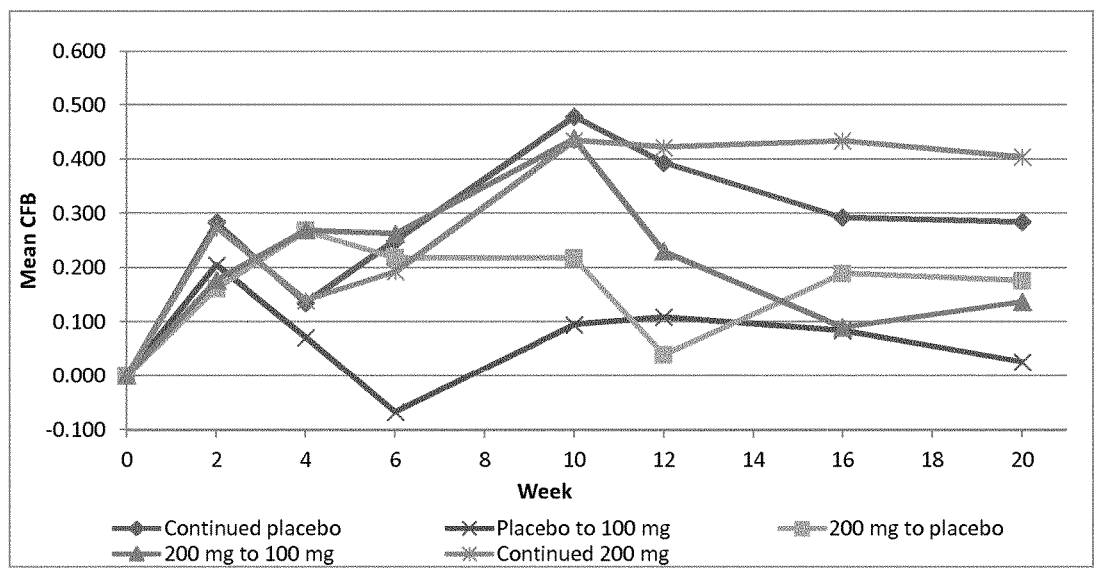
Figure 31B:
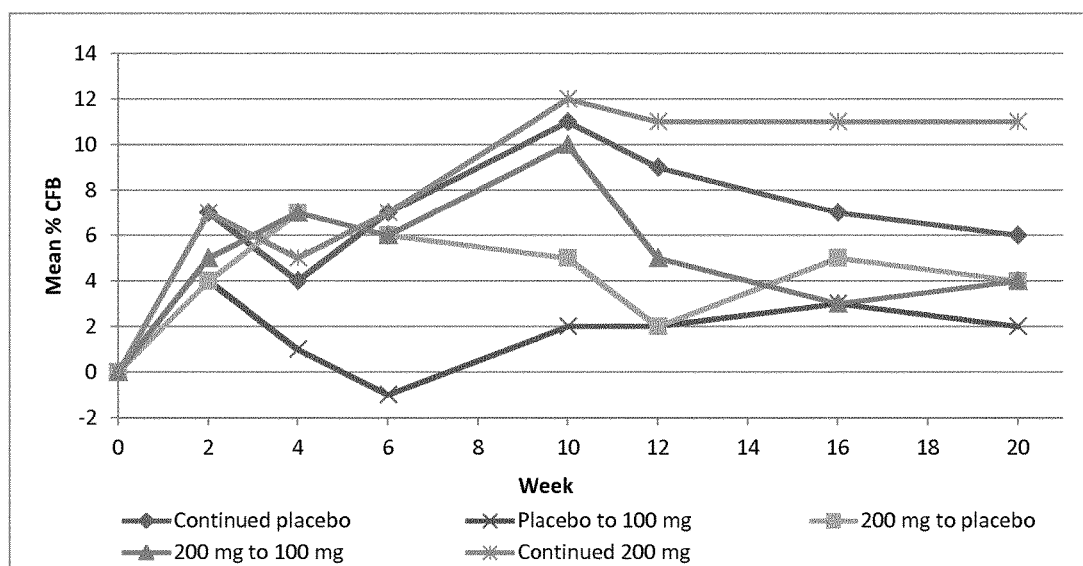

FIG. 31. Shows the change vs baseline in [Total cholesterol] level in the patient population upon administration of Compound 1 (dosed as [Compound 1:HCl:3H$_2$O] over 20 weeks in Study 5. FIG. 31A shows the mean variation in mmol/L, and FIG. 31B shows the mean % variation in the following groups: a) continued placebo (filled diamonds), b) placebo switching to 100 mg q.d. at week 10 (tilted crosses), c) 200 mg swiching to placebo at week 10 (filled square), d) 200 mg switching to 100 mg at week 10 (filled triangles), e) and continued 200 mg q.d. (asterisk).

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; the administration of an anti-malarial agent such as chloroquine, in advance of a visit to a geographical region where malaria is endemic or the risk of contracting malaria is high; and the administration of a lipid modulating agent to a patient at risk of developing cardiovascular disorders as measured for example, by the atherogenic index, or [LDL], [HDL], and/or [total cholesterol] to restore normal lipid blood level in said patient.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein, the term 'chronic' in a chronic condition, refers to a condition or disease that is persistent, and/or long-lasting in the effects it produces, and/or comes with time. In particular, the term refers to a condition or disease that persists over a period of greater than 4 weeks, or at least 8 weeks, or at least 12 weeks, or at least 16 weeks, or at least 20 weeks, or at least 24 weeks.

As used herein the term "cardiovascular disease" or "cardiovascular disorder" refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; shock; vasoconstriction (including that associated with migraines); vascular abnormality, insufficiency limited to a single organ or tissue. More particularly, the term refers to atherosclerosis.

As used herein, the term '[total cholesterol]' refers to concentration of lipoproteins in blood serum. In particular guidelines for [total cholesterol] are widely available, and normal values between 150 and 199 mg/dL (or 3.88 and 5.15 mmol/L) are recommended (*The Merck Manual of Diagnosis and Therapy*, 2011).

As used herein, the term '[LDL]' refers to the concentration of low density lipoprotein in blood serum. In particular guidelines for [LDL] are widely available, and normal values of ≤130 mg/dL (or 3.36 mmol/L) are recommended (*The Merck Manual of Diagnosis and Therapy*, 2011).

As used herein, the term '[HDL]' refers to the concentration of high density lipoprotein in blood serum. In particular guidelines for [HDL] are widely available, and normal values of ≥40 mg/dL (or ≥1.04 mmol/L) are recommended (*The Merck Manual of Diagnosis and Therapy*, 2011).

As used herein the term "dyslipidemia" refers to an abnormal amount of lipids in the blood, wherein the term lipid includes triglycerides, [LDL], [HDL] and/or [total cholesterol]. This may be excess of lipids, i.e. hyperlipidemia, or deficit of lipids i.e. hypolipidemia.

As used herein, the term 'Hypolipidemia' is defined as a condition, wherein an individual exhibits a [total cholesterol]<120 mg/dL (or <3.1 mmol/L) or [LDL]<50 mg/dL (or <1.3 mmol/L) (*The Merck Manual of Diagnosis and Therapy*, 2011).

As used herein, the term 'abnormal lipid profile' refers to a profile wherein [total cholesterol], [LDL], and/or [HDL] is outside of the recommended values as specified above. In a particular aspect, the abnormal lipid profile is characterized by a a [total cholesterol] below 120 mg/dL (or below 3.1 mmol/L) [LDL] below 50 mg/dL (or below 1.3 mmol/L). In another particular aspect, the abnormal lipid profile is characterized by a [HDL] below 40 mg/dL (or below 1.04 mmol/L).

As used herein, the term 'atherogenic index' refers to $$\frac{[total\ cholesterol]}{[HDL]}$$

As used herein, the term 'CRP' refers to t the C-Reactive protein in blood serum and is a marker of inflammation. In particular guidelines for CRP are widely available, and, and normal values of <0.5 mg/dL are recommended (*The Merck Manual of Diagnosis and Therapy*, 2011).

The unexpected finding of low cholesterol or low [LDL] cholesterol in a patient not taking a lipid-lowering drug should prompt a diagnostic evaluation, including measurements of AST, ALT, and thyroid-stimulating hormone; a negative evaluation suggests a possible primary cause.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

As used herein, the term 'DAS28(CRP)' refers to a clinical scoring ranging from 2.0 to 10.0 to measure the disease status at a given point in time, and thereby follow the progress and improvement of rheumatoid arthritis in a patient, and includes a 28 tender and swollen joint count, CRP measurement from blood analysis, and a general health assessment on a visual analog scale. A DAS28(CRP) value below 2.6 is indicative of remission, A DAS28(CRP) between 2.6 and 3.2 is indicative of low disease activity, between 3.2 and 5.1 is indicative of moderate disease activity, whereas a DAS28(CRP) above 5.1 is linked to high disease activity. (Wells et al., 2008)

As used herein, the term 'clinical RA afflicted individual' refers to an individual suffering from RA, and particularly refers to an individual showing a DAS28(CRP) score above 2.6.

As used herein, the term 'clinical non-RA afflicted individual' refers to an individual not suffering from RA, and particularly refers to an individual showing a DAS28(CRP) score below 2.6.

As used herein, the "Mayo Score" is a clinical scoring method to determine the severity of inflammatory bowel diseases (IBD) such as Crohn's disease and ulcerative colitis. It is composed of four categories (bleeding, stool frequency, physician assessment, and endoscopic appearance) each of which is rated from 0-3, the four scores are then summed to give a total score that ranges from 0-12.

"Crohn's Disease Activity Index" or "CDAI" is a clinical scoring methods used to determine the severity of Crohn's disease, which is made up of a number of items which are then multiplied by a weighting factor to give a final score. The items included are: number of liquid or very soft stools, abdominal pain, general well-being, extra-intestinal manifestations of Crohn's Disease, use of Lomotil/Imodium/opiates for diarrhea, abdominal mass, hematocrit (%) and body weight (Freeman, 2008).

"Ulcerative colitis disease activity index" or "UC DAI" is a clinical scoring method used to determine the severity of ulcerative colitis. The index assesses four variables, which include stool frequency, severity of bleeding, colonic mucosal appearance, and the physician's overall assessment of disease activity. Each variable is scored from 0-3 so that the total index score ranges from 0-12; 0-2: remission; 3-6: mild; 7-10: moderate; >10: severe UC (Tursi et al., 2010).

As used herein the term 'TNF-naïve patient' refers to a patient previously not exposed to anti-TNF monoclonal antibody treatment or subjects previously exposed to anti-TNF therapy (for example and without limitation infliximab, golimumab, adalimumab, certolizumab and/or certolizumab pegol) at a dose registered for the treatment of CD that has been discontinued at least 8 weeks prior to entering the study.

As used herein the term 'TNF-experienced patient' refers to a patient that is receiving at the time of entering the study or has received anti-TNF monoclonal antibody treatment (for example and without limitation infliximab, golimumab, adalimumab, certolizumab and/or certolizumab pegol) and is no longer responsive to such treatment.

As used herein the term 'anti-TNF pharmaceutical' refers a class of drugs that are used to treat inflammatory conditions, in particular rheumatoid arthritis (RA), psoriatic arthritis, juvenile arthritis, inflammatory bowel disease (Crohn's and ulcerative colitis), ankylosing spondylitis and psoriasis. TNF is a chemical produced by the immune system that causes inflammation in the body. In healthy individuals, excess TNF in the blood is blocked naturally, but in those inflammatory conditions, higher levels of TNF in the blood lead to more inflammation and persistent symptoms. Particular examples of anti-TNF pharmaceutical include infliximab, golimumab, adalimumab, certolizumab and certolizumab pegol.

As used herein the term 'corticosteroid' or 'glucocorticoid' refers to pharmaceutical agents that act by downregulating the transcription of proinflammatory genes (e.g., NF-κB) involved in cytokine production. Particular examples of corticosteroids include hydrocortisone, methylprednisolone, prednisone, prednisolone, or budesonide.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitro ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

The Invention

The present invention provides the compound of the invention for use in the prophylaxis and/or treatment of cardiovascular disorders and/or dyslipidemia. In particular, the compound of the invention may act as an inhibitor of JAK, and more particularly of JAK1.

Furthermore, the present invention provides pharmaceutical compositions comprising the compound of the invention for use in the prophylaxis and/or treatment of cardiovascular disorders and/or dyslipidemia.

The present invention also provides methods for the production of these pharmaceutical compositions of the invention and methods for the prophylaxis and/or treatment of cardiovascular disorders and/or dyslipidemia by administering the pharmaceutical compositions of the invention.

Accordingly, in a first aspect of the invention, is provided the compound of the invention for use is the prophylaxis and/or treatment of cardiovascular disorders and/or dyslipidemia, wherein said compound of the invention is according to Formula (I):

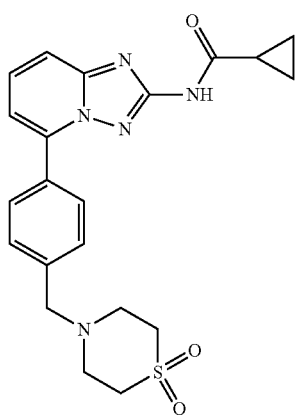

I or a pharmaceutically acceptable salt thereof, or a solvate or the salt of a solvate thereof, or an active metabolite thereof for use in the prophylaxis and/or treatment of cardiovascular disorders and/or dyslipidemia.

In one embodiment, the compound of the invention is a metabolite of the compound according to Formula I, said metabolite being according to Formula II:

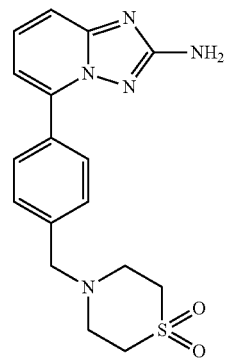

II

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound. In a particular embodiment, the solvate of a pharmaceutically acceptable salt is a [Compound according to Formula I:HCl:3H$_2$O] adduct.

It will be appreciated that compounds of the invention may be metabolized to yield biologically active metabolites.

CLAUSES

1. A compound according to Formula I:

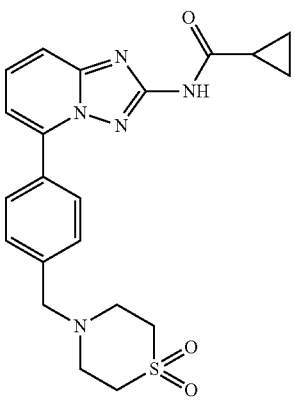

I or a pharmaceutically acceptable salt thereof, or a solvate or the salt of a solvate thereof, or an active metabolite thereof for use in the prophylaxis and/or treatment of cardiovascular disorders and/or dyslipidemia.

2. The compound according to clause 1, wherein the compound is the free base.

3. The compound according to clause 1, wherein the pharmaceutically acceptable salt of the solvate is a [Compound according to Formula I:HCl:3H$_2$O] adduct.

4. A compound according to Formula II:

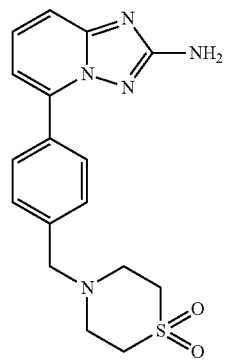

or a pharmaceutically acceptable salt thereof, or a solvate or the salt of a solvate thereof, for use in the prophylaxis and/or treatment of cardiovascular disorders and/or dyslipidemia.

5. A compound, or a pharmaceutically acceptable salt thereof for use according to any one of clauses clause 1-4, wherein the cardiovascular disorder is atherosclerosis.

6. A compound, or a pharmaceutically acceptable salt thereof for use according to any one of clauses clause 1-4, wherein the dyslipidemia is hypolipidemia.

7. A compound, or a pharmaceutically acceptable salt thereof for use according to any one of clauses 1-6, in combination with a further therapeutic agent.

8. A pharmaceutical composition for use in the prophylaxis and/or treatment of cardiovascular disorders and/or dyslipidemia, comprising the compound according to Formula I, or a pharmaceutically acceptable salt thereof, and a pharmaceutically acceptable carrier, excipient, or diluent.

9. A pharmaceutical composition for use according to clause 8, comprising a further therapeutic agent.

10. A compound, or a pharmaceutically acceptable salt thereof, for use according to any one of clauses 1-7, or a pharmaceutical composition according to clause 8 or 9 in an individual presenting an abnormal lipid profile.

11. A compound, or a pharmaceutically acceptable salt thereof, or a pharmaceutical composition for use according to clause 10, wherein the abnormal lipid profile is characterized by [total cholesterol] below 120 mg/dL.

12. A compound, or a pharmaceutically acceptable salt thereof, or a pharmaceutical composition for use according to clause 10, wherein the abnormal lipid profile is characterized by [total cholesterol] below 3.1 mmol/L.

13. A compound, or a pharmaceutically acceptable salt thereof, or a pharmaceutical composition for use according to clause 10, wherein the abnormal lipid profile is characterized by [LDL] below 50 mg/dL.

14. A compound, or a pharmaceutically acceptable salt thereof, or a pharmaceutical composition for use according to clause 10, wherein the abnormal lipid profile is characterized by [LDL] below 1.3 mmol/L.

15. A compound, or a pharmaceutically acceptable salt thereof, or a pharmaceutical composition for use according to clause 10, wherein the abnormal lipid profile is characterized by [HDL] below 40 mg/dL.

16. A compound, or a pharmaceutically acceptable salt thereof, or a pharmaceutical composition for use according to clause 10, wherein the abnormal lipid level is characterized by [HDL] levels below 1.04 mmol/L.

17. A compound, or a pharmaceutically acceptable salt thereof, for use according to any one of clauses 1-7, or a pharmaceutical composition according to clause 8 or 9 in a clinical non RA-afflicted patient.

18. A compound, or a pharmaceutically acceptable salt thereof, for use according to any one of clauses 1-7, or a pharmaceutical composition according to clause 8 or 9 in a clinical patient afflicted with IBD.

19. A compound, or a pharmaceutically acceptable salt thereof, for use according to any one of clauses 1-7, or a pharmaceutical composition according to clause 8 or 9 in a clinical patient afflicted with IBD.

20. A compound, or a pharmaceutically acceptable salt thereof, for use according to any one of clauses 1-7, or a pharmaceutical composition according to clause 8 or 9 in a clinical non RA-afflicted patient, wherein the non RA-afflicted condition is measured by the DAS28(CRP) score.

21. A compound, or a pharmaceutically acceptable salt thereof, for use according to any one of clauses 1-7, or a pharmaceutical composition according to clause 8 or 9 in a clinical non RA-afflicted patient, wherein the non RA-afflicted condition is measured by the DAS28(CRP) score, and wherein the DAS28(CRP) score is less than 2.6.

22. A compound, or a pharmaceutically acceptable salt thereof, for use according to any one of clauses 1-7, or a pharmaceutical composition according to clause 8 or 9 in a clinical non RA-afflicted patient, wherein the non RA-afflicted condition is measured by the DAS28(CRP) score, wherein the DAS28(CRP) score is less than 2.6 and having a CRP level greater than 3 mg/L 23. A compound, or a pharmaceutically acceptable salt thereof, for use according to any one of clauses 1-7, or a pharmaceutical composition according to clause 8 or 9 in a clinical RA-afflicted patient, wherein the compound of the invention or pharmaceutical compositions comprising a compound of the invention is administered at least once a week over a period of greater than 4 weeks.

24. A compound, or a pharmaceutically acceptable salt thereof, for use according to any one of clauses 1-7, or a pharmaceutical composition according to clause 8 or 9 in a clinical RA-afflicted patient, wherein the compound of the invention or pharmaceutical compositions comprising a compound of the invention is administered at least once a week over a period of at least 12 weeks.

25. A compound, or a pharmaceutically acceptable salt thereof, or a pharmaceutical composition for use according to clause 23 or 24, wherein the clinical RA-afflicted patient condition is measured by the DAS28(CRP) score.

26. A compound, or a pharmaceutically acceptable salt thereof, or a pharmaceutical composition according for use according to clause 23 or 24, wherein the clinical RA-afflicted patient condition is measured by the DAS28 (CRP) score, and wherein the DAS28(CRP) score is greater than 3.2.

27. A compound, or a pharmaceutically acceptable salt thereof, or a pharmaceutical composition according for use according to any one of clauses 23-26, wherein the RA-afflicted patient has previously had an insufficient response to methotrexate.

28. A compound, or a pharmaceutically acceptable salt thereof, or a pharmaceutical composition according for use according to any one of clauses 23-26, wherein the RA-afflicted patient is concomitantly treated with methotrexate.

29. A compound, or a pharmaceutically acceptable salt thereof, or a pharmaceutical composition according for use according to any one of clauses 23-26, wherein the RA-afflicted patient is concomitantly treated with methotrexate and receives between 7.5-25 mg once per week of methotrexate.

30. A compound, or a pharmaceutically acceptable salt thereof, or a pharmaceutical composition according for use according to any one of clauses 23-26, wherein the RA-afflicted patient is concomitantly treated with methotrexate and receives between 10-25 mg once per week of methotrexate.

31. A compound, or a pharmaceutically acceptable salt thereof for use according to any one of clauses 1-30, wherein said compound, or pharmaceutically acceptable salt thereof is administered 1, 2, 3, 4, 5, 6 or 7 times a week.

32. A compound, or a pharmaceutically acceptable salt thereof for use according to any one of clauses 1-30, wherein said compound, or pharmaceutically acceptable salt thereof is administered 1, 2, or 3 times a week.

33. A compound, or a pharmaceutically acceptable salt thereof for use according to clauses 31 or 32, wherein said compound, or pharmaceutically acceptable salt thereof is administered over a period greater than 4 weeks.

34. A compound, or a pharmaceutically acceptable salt thereof for use according to clauses 31 or 32, wherein said compound, or pharmaceutically acceptable salt thereof is administered over a period of at least 12 weeks.

35. A compound, or a pharmaceutically acceptable salt thereof for use according to clauses 31 or 32, wherein said compound, or pharmaceutically acceptable salt thereof is administered over a period of at least 24 weeks.

36. A compound, or a pharmaceutically acceptable salt thereof for use according to any one of clauses 1-35, wherein said compound, or pharmaceutically acceptable salt thereof is administered at a dose of 25-400 mg per day.

37. A compound, or a pharmaceutically acceptable salt thereof for use according to any one of clauses 1-35, wherein said compound, or pharmaceutically acceptable salt thereof is administered at a dose of 100-250 mg per day.

38. A compound, or a pharmaceutically acceptable salt thereof for use according to any one of clause 1-35, wherein said compound, or pharmaceutically acceptable salt thereof is administered at a dose of 200 mg once a day.

39. A compound, or a pharmaceutically acceptable salt thereof for use according to any one of clauses 1-35, wherein said compound, or pharmaceutically acceptable salt thereof is administered at a dose of 100 mg twice a day.

40. A method for the treatment the prophylaxis and/or treatment of cardiovascular disorders and/or dyslipidemia comprising the steps of:

measuring the DAS28(CRP) levels of an individual by performing a 28 tender and swollen joint count, CRP measurement from blood analysis, and a general health assessment on a visual analog scale, comparing said DAS28(CRP) level to the disease scoring index wherein a score below 2.6 is indicative of remission, a score between 2.6 and 3.2 is indicative of low disease activity, a score between 3.2 and 5.1 is indicative of moderate disease activity, and a score above 5.1 is linked to high disease activity, determining a dose of the compound according to Formula I, or a pharmaceutically acceptable salt thereof comprised between 25 mg and 400 mg for administration to said individual.

41. The compound or a pharmaceutically acceptable salt thereof, according to clause 7 or the pharmaceutical composition for use according to clause 9, wherein the further therapeutic agent is an agent for the prophylaxis and/or treatment of cardiovascular disease.

42. The compound or a pharmaceutically acceptable salt thereof, according to clause 7 or the pharmaceutical composition for use according to clause 9, wherein the further therapeutic agent is an agent for the prophylaxis and/or treatment of atherosclerosis.

43. The compound or a pharmaceutically acceptable salt thereof, according to clause 7 or the pharmaceutical composition for use according to clause 9, wherein the further therapeutic agent is an agent for the prophylaxis and/or treatment of dyslipidemia.

44. The compound or a pharmaceutically acceptable salt thereof, according to clause 7 or the pharmaceutical composition for use according to clause 9, wherein the further therapeutic agent is an agent for the prophylaxis and/or treatment of hypolipidemia 45. The compound or a pharmaceutically acceptable salt thereof, according to clause 7 or the pharmaceutical composition for use according to clause 9, wherein the further therapeutic agent is an agent for the prophylaxis and/or treatment of inflammatory disorders.

46. The compound or a pharmaceutically acceptable salt thereof, according to clause 7 or the pharmaceutical composition for use according to clause 9, wherein the further therapeutic agent is an agent for the prophylaxis and/or treatment of rheumatoid arthritis.

47. The compound or a pharmaceutically acceptable salt thereof, according to clause 7 or the pharmaceutical composition for use according to clause 9, wherein the further therapeutic agent is methotrexate.

48. The compound or a pharmaceutically acceptable salt thereof, according to clause 7 or the pharmaceutical composition for use according to clause 9, wherein the further therapeutic agent is an agent for the prophylaxis and/or treatment of IBD.

49. The compound or a pharmaceutically acceptable salt thereof, according to clause 7 or the pharmaceutical composition for use according to clause 9, wherein the further therapeutic agent is an agent for the prophylaxis and/or treatment of Crohn's disease.

50. A method for the prophylaxis and/or treatment of cardiovascular disorders and/or dyslipidemia in a patient in need thereof, said method comprising administering an amount sufficient to effect said prophylaxis and/or treatment, of a compound according to Formula I:

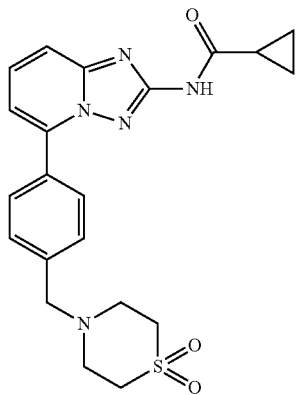

I or a pharmaceutically acceptable salt thereof, or a solvate or the salt of a solvate thereof, or an active metabolite thereof.

51. A method for the prophylaxis and/or treatment of cardiovascular disorders and/or dyslipidemia in a patient in need thereof, said method comprising administering an amount sufficient to effect said prophylaxis and/or treatment, of a compound according to Formula II:

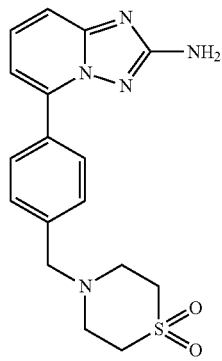

II or a pharmaceutically acceptable salt thereof, or a solvate or the salt of a solvate thereof.

52. The method according to clause 50, wherein the pharmaceutically acceptable salt of a solvate is a [Compound according to Formula I:HCl:3H$_2$O] adduct.
53. The method according to any one of clauses 50-52, wherein the cardiovascular disorder is atherosclerosis.
54. The method according to any one of clauses 50-52, wherein the dyslipidemia is hypolipidemia.
55. A method of increasing [HDL] levels in the blood of a patient in need thereof, which method comprises administering an amount sufficient to increase said [HDL] levels, of a compound according to Formula I:

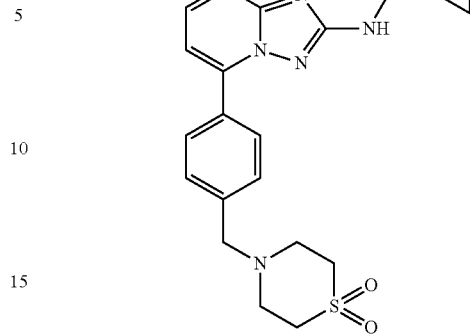

I or a pharmaceutically acceptable salt thereof, or a solvate or the salt of a solvate thereof, or an active metabolite thereof.

56. The method according to clause 55, wherein the pharmaceutically acceptable salt of a solvate is a [Compound according to Formula I:HCl:3H$_2$O] adduct.
57. The method according to clauses 55 or 56, wherein the [HDL] compared to prior to the treatment level is increased by at least 5%, at least 10%, at least 15%, at least 20% and/or 23%.
58. A method of decreasing the atherogenic index in a patient in need thereof, which method comprises administering an amount sufficient to decrease said atherogenic index, of a compound according to Formula I:

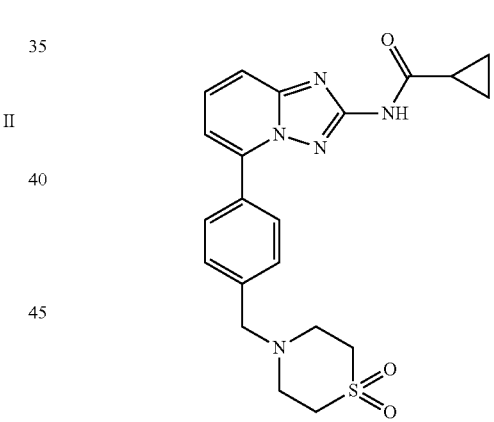

I or a pharmaceutically acceptable salt thereof, or a solvate or the salt of a solvate thereof, or an active metabolite thereof.

59. The method according to clause 58, wherein the pharmaceutically acceptable salt of a solvate is a [Compound according to Formula I:HCl:3H$_2$O] adduct.
60. The method according to clauses 58 or 59, wherein the atherogenic index compared to prior to the treatment level is decreased by at least 0.2, by at least 0.3, and/or at least 0.35.

PHARMACEUTICAL COMPOSITIONS

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, $17^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 300 mg tablets (100 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 200 mg capsules (100 mg of active compound of the invention according to Formula I per capsule).

Formulation 3—Liquid

A compound of the invention according to Formula I (100 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 300-600 mg tablets (100-200 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (100 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention or pharmaceutical compositions comprising a compound of the invention, for use in the prophylaxis and/or treatment of cardiovascular disorders and/or dyslipidemia. In a particular embodiment, the cardiovascular disorder is atherosclerosis. In another particular embodiment, the dyslipidemia is hypolipidemia.

In another embodiment, the present invention provides compounds of the invention, or pharmaceutical compositions comprising a compound of the invention for use in the manufacture of a medicament for the prophylaxis and/or treatment of cardiovascular disorders and/or dyslipidemia. In a particular embodiment, the cardiovascular disorder is atherosclerosis. In another particular embodiment, the dyslipidemia is hypolipidemia.

In additional method of treatment aspects, this invention provides methods of prophylaxis and/or treatment of a mammal afflicted with cardiovascular disorders and/or dyslipidemia, which methods comprise the administration of an effective amount of a compound of the invention or one or more of the pharmaceutical compositions herein described for the treatment or prophylaxis of said condition. In a particular embodiment, the cardiovascular disorder is atherosclerosis. In another particular embodiment, the dyslipidemia is hypolipidemia.

In one embodiment, the present invention provides compounds of the invention or pharmaceutical compositions comprising a compound of the invention, for use in the prophylaxis and/or treatment of patients presenting an abnormal lipid profile. In a particular embodiment, the abnormal lipid profile is characterized by [total cholesterol] below 120 mg/dL or 3.1 mmol/L. In another particular embodiment, the abnormal lipid profile is characterized by [LDL] below 50 mg/dL (or below 1.3 mmol/L). In yet another particular embodiment, the abnormal lipid profile is characterized by [HDL] below 40 mg/dL (or below 1.04 mmol/L). In a more particular embodiment, the abnormal lipid profile is characterized by [LDL] below 50 mg/dL (or below 1.3 mmol/L) and [HDL] below 40 mg/dL (or below 1.04 mmol/L).

In another embodiment, the present invention provides compounds of the invention, or pharmaceutical compositions comprising a compound of the invention for use in the manufacture of a medicament for the prophylaxis and/or treatment of patients presenting an abnormal lipid profile. In a particular embodiment, the abnormal lipid profile is characterized by [total cholesterol] below 120 mg/dL or 3.1 mmol/L. In another particular embodiment, the abnormal lipid profile is characterized by [LDL] below 50 mg/dL (or below 1.3 mmol/L). In yet another particular embodiment, the abnormal lipid profile is characterized by [HDL] below 40 mg/dL (or below 1.04 mmol/L). In a more particular embodiment, the abnormal lipid profile is characterized by [LDL] below 50 mg/dL (or below 1.3 mmol/L) and [HDL] below 40 mg/dL (or below 1.04 mmol/L).

In additional method of treatment aspects, this invention provides methods of prophylaxis and/or treatment of patients presenting an abnormal lipid profile, which methods comprise the administration of an effective amount of a compound of the invention or one or more of the pharmaceutical compositions herein described for the treatment or prophylaxis of said condition. In a particular embodiment, the abnormal lipid profile is characterized by [total cholesterol] below 120 mg/dL or 3.1 mmol/L. In another particular embodiment, the abnormal lipid profile is characterized by [LDL] below 50 mg/dL (or below 1.3 mmol/L). In yet another particular embodiment, the abnormal lipid profile is characterized by [HDL] below 40 mg/dL (or below 1.04 mmol/L). In a more particular embodiment, the abnormal lipid profile is characterized by [LDL] below 50 mg/dL (or below 1.3 mmol/L) and [HDL] below 40 mg/dL (or below 1.04 mmol/L).

In one embodiment, the present invention provides compounds of the invention or pharmaceutical compositions comprising a compound of the invention, for use in the prophylaxis and/or treatment of cardiovascular disorders and/or dyslipidemia in a clinical non RA-afflicted patient. In a particular embodiment, the non-RA afflicted condition is measured by the DAS28(CRP) score. In a more particular embodiment, the non-RA afflicted condition is measured by the DAS28(CRP) wherein the DAS28(CRP) score is less than 2.6. In a most particular embodiment, the non-RA afflicted condition is measured by the DAS28(CRP) score, wherein the DAS28(CRP) score is less than 2.6, and the CRP is greater than 3 mg/L.

In another embodiment, the present invention provides compounds of the invention, or pharmaceutical compositions comprising a compound of the invention for use in the manufacture of a medicament for the prophylaxis and/or treatment of cardiovascular disorders and/or dyslipidemia in a clinical non RA-afflicted patient. In a particular embodiment, the non-RA afflicted condition is measured by the DAS28(CRP) score. In a more particular embodiment, the non-RA afflicted condition is measured by the DAS28(CRP) wherein the DAS28(CRP) score is less than 2.6. In a most particular embodiment, the non-RA afflicted condition is measured by the DAS28(CRP) score, wherein the DAS28 (CRP) score is less than 2.6, and the CRP is greater than 3 mg/L.

In additional method of treatment aspects, this invention provides methods of prophylaxis and/or treatment of cardiovascular disorders and/or dyslipidemia in a clinical non RA-afflicted patient, which methods comprise the administration of an effective amount of a compound of the invention or one or more of the pharmaceutical compositions herein described for the treatment or prophylaxis of said condition. In a particular embodiment, the non-RA afflicted condition is measured by the DAS28(CRP) score. In a more particular embodiment, the non-RA afflicted condition is measured by the DAS28(CRP) wherein the DAS28(CRP) score is less than 2.6. In a most particular embodiment, the non-RA afflicted condition is measured by the DAS28(CRP) score, wherein the DAS28(CRP) score is less than 2.6, and the CRP is greater than 3 mg/L.

In one embodiment, the present invention provides a compound of the invention or pharmaceutical compositions comprising a compound of the invention, for use in the prophylaxis and/or treatment of chronic cardiovascular disorders in a clinical RA-afflicted patient, wherein the compound of the invention or pharmaceutical compositions comprising a compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising a compound of the invention is administered over a period of at least 12, at least 24, or at least 36 weeks. In a more particular embodiment, the clinical RA-afflicted patient condition is measured by the DAS28(CRP) score. In a particular embodiment, the clinical RA-afflicted patient condition is measured by the DAS28(CRP) score, wherein said DAS28(CRP) score is greater than 3.2.

In one embodiment, the present invention provides a compound of the invention or pharmaceutical compositions comprising a compound of the invention, for use in the manufacture of a medicament for the prophylaxis and/or treatment of chronic cardiovascular disorders in a clinical RA-afflicted patient, wherein the compound of the invention or pharmaceutical compositions comprising a compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising a compound of the invention is administered over a period of at least 12, at least 24, or at least 36 weeks. In a more particular embodiment, the clinical RA-afflicted patient condition is measured by the DAS28(CRP) score. In a particular embodiment, the clinical RA-afflicted patient condition is measured by the DAS28(CRP) score, wherein said DAS28(CRP) score is greater than 3.2.

In additional method of treatment aspects, this invention provides methods of prophylaxis and/or treatment of chronic cardiovascular disorders in a clinical RA-afflicted patient, which methods comprise the administration of an effective amount of a compound of the invention or one or more of the pharmaceutical compositions herein described for the treatment or prophylaxis of said condition. In a particular embodiment, the compound of the invention or pharmaceutical compositions comprising a compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising a compound of the invention is administered over a period of at least 12, at least 24, or at least 36 weeks. In a more particular embodiment, the clinical RA-afflicted patient condition is measured by the DAS28(CRP) score. In a particular embodiment, the clinical RA-afflicted patient condition is measured by the DAS28(CRP) score, wherein said DAS28(CRP) score is greater than 3.2.

In one embodiment, the present invention provides a compound of the invention or pharmaceutical compositions comprising a compound of the invention, for use in the prophylaxis and/or treatment of chronic cardiovascular disorders in a clinical RA-afflicted patient which have previously had an insufficient response to methotrexate, wherein the compound of the invention or pharmaceutical compositions comprising the compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising the compound of the invention is administered over a period of at least 12, at least 24, or at least 36 weeks. In a more particular embodiment, the clinical RA-afflicted patient's condition is measured by the DAS28(CRP) score. In a particular embodiment, the clinical RA-afflicted patient's condition is measured by the DAS28(CRP) score, wherein said DAS28(CRP) score is greater than 3.2.

In one embodiment, the present invention provides a compound of the invention or pharmaceutical compositions comprising the compound of the invention, for use in the manufacture of a medicament for the prophylaxis and/or treatment of chronic cardiovascular disorders in a clinical RA-afflicted patient who has previously had an insufficient response to methotrexate, wherein the compound of the invention or pharmaceutical compositions comprising the compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising the compound of the invention is administered over a period of at least 12, at least 24, or at least 36 weeks. In a more particular embodiment, the clinical RA-afflicted patient's condition is measured by the DAS28(CRP) score. In a particular embodiment, the clinical RA-afflicted patient's condition is measured by the DAS28(CRP) score, wherein said DAS28(CRP) score is greater than 3.2.

In additional method of treatment aspects, this invention provides methods of prophylaxis and/or treatment of chronic cardiovascular disorders in a clinical RA-afflicted patient who has previously had an insufficient response to methotrexate, which methods comprise the administration of an effective amount of the compound of the invention or one or more of the pharmaceutical compositions herein described for the treatment or prophylaxis of said condition. In a particular embodiment, the compound of the invention or pharmaceutical compositions comprising the compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising the compound of the invention is administered over a period of at least 12, at least 24, or at least 36 weeks. In a more particular embodiment, the clinical RA-afflicted patient's condition is measured by the DAS28(CRP) score. In a particular embodiment, the clinical RA-afflicted patient's condition is measured by the DAS28(CRP) score, wherein said DAS28(CRP) score is greater than 3.2.

In one embodiment, the present invention provides a compound of the invention or pharmaceutical compositions comprising the compound of the invention, for use in the prophylaxis and/or treatment of chronic cardiovascular disorders in a clinical RA-afflicted patient which patient is concomitantly treated with methotrexate, wherein the compound of the invention or pharmaceutical compositions comprising the compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising the compound of the invention is administered over a period of at least 12, at least 24, or at least 36 weeks. In a more particular embodiment, the clinical RA-afflicted patient's condition is measured by the DAS28(CRP) score. In a particular embodiment, the clinical RA-afflicted patient's condition is measured by the DAS28(CRP) score, wherein said DAS28 (CRP) score is greater than 3.2. In a more particular embodiment, the patient concomitantly receives between 7.5-25 mg once per week of methotrexate. In a further more particular embodiment, the patient concomitantly receives between 10-25 mg once per week of methotrexate.

In one embodiment, the present invention provides a compound of the invention or pharmaceutical compositions comprising the compound of the invention, for use in the manufacture of a medicament for the prophylaxis and/or treatment of chronic cardiovascular disorders in a clinical RA-afflicted patient which patient is concomitantly treated with methotrexate, wherein the compound of the invention or pharmaceutical compositions comprising the compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising the compound of the invention is administered over a period of at least 12, at least 24, or at least 36 weeks. In a more particular embodiment, the clinical RA-afflicted patient's condition is measured by the DAS28(CRP) score. In a particular embodiment, the clinical RA-afflicted patient's condition is measured by the DAS28(CRP) score, wherein said DAS28(CRP) score is greater than 3.2. In a more particular embodiment, the patient concomitantly receives between 7.5-25 mg once per week of methotrexate. In a further more particular embodiment, the patient concomitantly receives between 10-25 mg once per week of methotrexate.

In additional method of treatment aspects, this invention provides methods of prophylaxis and/or treatment of chronic cardiovascular disorders in a clinical RA-afflicted patient which patient is concomitantly treated with methotrexate, which methods comprise the administration of an effective amount of a compound of the invention or one or more of the pharmaceutical compositions herein described for the treatment or prophylaxis of said condition. In a particular embodiment, the compound of the invention or pharmaceutical compositions comprising a compound of the invention is administered at least once a week over a period of greater than 4 weeks, or at least 8, at least 10, at least 12, at least 16, at least 20, at least 24, at least 28, at least 32, or at least 36 weeks. In a particular embodiment, the compound of the invention or pharmaceutical compositions comprising the compound of the invention is administered over a period of at least 12, at least 24, or at least 36 weeks. In a more particular embodiment, the clinical RA-afflicted patient's condition is measured by the DAS28(CRP) score. In a particular embodiment, the clinical RA-afflicted patient's condition is measured by the DAS28(CRP) score, wherein said DAS28(CRP) score is greater than 3.2. In a more particular embodiment, the patient concomitantly receives between 7.5-25 mg once per week of methotrexate. In a further more particular embodiment, the patient concomitantly receives between 10-25 mg once per week of methotrexate.

In one embodiment, the present invention provides a compound of the invention or pharmaceutical compositions comprising a compound of the invention, for use in the prophylaxis and/or treatment of chronic cardiovascular disorders wherein said compound, or pharmaceutically acceptable salt thereof is administered 1, 2, 3, 4, 5, 6 or 7 times a week. In a particular embodiment, the compound, or pharmaceutically acceptable salt thereof is administered 1, 2, or 3 times a week.

In one embodiment, the present invention provides a compound of the invention or pharmaceutical compositions comprising a compound of the invention, for use in the prophylaxis and/or treatment of chronic cardiovascular disorders wherein said compound, or pharmaceutically acceptable salt thereof is administered 1, 2, 3, 4, 5, 6 or 7 times a week, over a period greater than 4 weeks. In a particular embodiment, the compound, or pharmaceutically acceptable salt thereof is administered 1, 2, or 3 times a week, over a period greater than 4 weeks.

In one embodiment, the present invention provides a compound of the invention or pharmaceutical compositions comprising a compound of the invention, for use in the prophylaxis and/or treatment of chronic cardiovascular disorders wherein said compound, or pharmaceutically acceptable salt thereof is administered 1, 2, 3, 4, 5, 6 or 7 times a week, over a period of at least 12 weeks. In a particular embodiment, the compound, or pharmaceutically acceptable salt thereof is administered 1, 2, or 3 times a week, over a period of at least 12 weeks.

In one embodiment, the present invention provides a compound of the invention or pharmaceutical compositions comprising a compound of the invention, for use in the prophylaxis and/or treatment of chronic cardiovascular disorders wherein said compound, or pharmaceutically acceptable salt thereof is administered 1, 2, 3, 4, 5, 6 or 7 times a week, over a period of at least 24 weeks. In a particular embodiment, the compound, or pharmaceutically acceptable salt thereof is administered 1, 2, or 3 times a week, over a period of at least 24 weeks.

In one embodiment, the present invention provides a compound of the invention or pharmaceutical compositions comprising a compound of the invention, for use in the prophylaxis and/or treatment of cardiovascular disorders in IBD patients. In a particular embodiment, the present invention provides a compound of the invention or pharmaceutical compositions comprising a compound of the invention, for use in the prophylaxis and/or treatment of cardiovascular disorders in ulcerative colitis and/or Crohn's disease patients. In a more particular embodiment, the present invention provides a compound of the invention or pharmaceutical compositions comprising a compound of the invention, for use in the prophylaxis and/or treatment of cardiovascular disorders in Crohn's disease patients.

In one embodiment, the present invention provides a compound of the invention or pharmaceutical compositions comprising a compound of the invention, for use in the prophylaxis and/or treatment of chronic cardiovascular disorders wherein said compound, or pharmaceutically acceptable salt thereof is administered at a dose of 25-400 mg per day. In a particular embodiment, the compound, or pharmaceutically acceptable salt thereof is administered at a dose of 100-250 mg per day.

In one embodiment, the present invention provides a compound of the invention or pharmaceutical compositions comprising a compound of the invention, for use in the prophylaxis and/or treatment of chronic cardiovascular disorders wherein said compound, or pharmaceutically acceptable salt thereof is administered at a dose of 200 mg once a day.

In one embodiment, the present invention provides a compound of the invention or pharmaceutical compositions comprising a compound of the invention, for use in the prophylaxis and/or treatment of chronic cardiovascular disorders wherein said compound, or pharmaceutically acceptable salt thereof is administered at a dose of 100 mg twice a day.

In one embodiment, the present invention provides a method for the treatment the prophylaxis and/or treatment of cardiovascular disorders and/or dyslipidemia comprising the steps of:
- measuring the DAS28(CRP) levels of an individual by performing a 28 tender and swollen joint count, CRP measurement from blood analysis, and a general health assessment on a visual analog scale (Fransen et al., 2003),
- comparing said DAS28(CRP) level to the disease scoring index wherein a score below 2.6 is indicative of remission, a score between 2.6 and 3.2 is indicative of low disease activity, a score between 3.2 and 5.1 is indicative of moderate disease activity, and a score above 5.1 is linked to high disease activity,
- determining a dose of the compound according to Formula I, or a pharmaceutically acceptable salt thereof comprised between 25 and 400 mg for administration to said individual.

In one embodiment, the present invention provides a method of increasing [HDL] levels in the blood of a patient in need thereof, which method comprises administering an amount sufficient to increase said [HDL] levels of Compound 1. In a particular embodiment, the [HDL] compared to the prior to the treatment level is increased by at least 5%, at least 10%, at least 15%, at least 20%, and/or 23%.

In one embodiment, the present invention provides a method of decreasing the atherogenic index in a patient in need thereof, which method comprises administering an amount sufficient to decrease said atherogenic index of Compound 1. In a particular embodiment, the atherogenic index compared to prior to the treatment level is decreased by at least 0.2, by at least 0.3, and/or at least 0.35.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as chronic conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 25 to about 400 mg of a compound of the invention, with particular doses each providing from about 50 to about 250 mg and especially about 100 to about 200 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, the present invention provides pharmaceutical compositions comprising a compound of the invention, and another therapeutic agent.

In one embodiment, a compound of the invention is co-administered with another therapeutic agent for the treatment and/or prophylaxis of cardiovascular disorder. In a particular embodiment, the cardiovascular disorder is atherosclerosis. In a particular embodiment, the other therapeutic agent for the treatment and/or prophylaxis of cardiovascular disorders is selected from lipid lowering statins (HMG-CoA reductase inhibitors) (e.g. Atorvastatin, Fluvastatin, Lovastatin, Mevastatin, Pitavastatin, Pravastatin, Rosuvastatin, and/or Simvastatin); anti-hypertensives (e.g. angiotensin converting enzyme inhibitors (Benazepril, Captopril, Cilazapril, Enalapril, Fosinopril, Lisinopril, Perindopril, Quinapril, Ramipril, Trandolapril, and/or Zofenopril), angiotensin II receptor antagonists (Candesartan, Eprosartan, Irbesartan, Losartan, Olmesartan, Telmisartan, Valsartan), Calcium channel blockers (Amlodipine, Barnidipine, Cilnidipine, Felodipine, Isradipine, Lacidipine, Lercanidipine, Levamlodipine, Nicardipine, Nifedipine, Nimodipine, Nisoldipine, Nitrendipine, Verapamil, and/or Diltiazem), thiazide diuretics (Epitizide, Hydrochlorthiazide, Chlorthiazide, Bendroflumethiazide, Chlorthalidone, Indapamide, and/or Metolazone), beta-blockers (Acebutolol, Atenolol, Betaxolol, Bisoprolol, Carvedilol, Celiprolol, Esmolol, Labetalol, Metoprolol, Nadolol, Nebivolol, Oxprenolol, Pindolol, Propranolol, and/or Timolol), alpha-blockers (Doxazosin, Phentolamine, Indoramin, Phenoxybenzamine, Prazosin, Terazosin, and/or Talazoline), renin inhibitor (Aliskiren); and/or anti platelet (Low dose aspirin, or Clopidogrel).

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts and Greene, 2012).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 µm). Thin layer chromatography was carried out using pre-coated silica gel F-254 plates (thickness 0.25 mm). $^1$H NMR spectra were recorded on a Bruker DPX 400 NMR spectrometer (400 MHz) or a Bruker Advance 300 NMR spectrometer (300 MHz). Chemical shifts (δ) for $^1$H NMR spectra are reported in parts per million (ppm) relative to tetramethylsilane (δ 0.00) or the appropriate residual solvent peak, i.e. CHCl$_3$ (δ 7.27) as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or Waters Acquity H-Class UPLC coupled to a Waters Mass detector 3100 spectrometer. Columns used: Waters Acquity UPLC BEH C18 1.7 µm, 2.1 mm ID×50 mm L, Waters Acquity UPLC BEH C18 1.7 µm, 2.1 mm ID×30 mm L, or Waters Xterra MS 5 µm C18, 100×4.6 mm. The methods are using either MeCN/H$_2$O gradients (H$_2$O contains either 0.1% TFA or 0.1% NH$_3$) or MeOH/H$_2$O gradients (H$_2$O contains 0.05% TFA). Microwave heating was performed with a Biotage Initiator.

TABLE I

List of abbreviations used in the experimental section:

| Abbreviation | Definition |
|---|---|
| µL | microliter |
| µM | micromolar |
| br s | broad singlet |
| DCM | Dichloromethane |
| DMF | N,N-dimethylformamide |
| DMSO | Dimethylsulfoxide |
| cpm | Counts per minute |
| Et$_2$O | Diethyl ether |
| EtOAc | Ethyl acetate |
| FBS | Fetal bovine serum |
| eq | equivalents |
| g | gram |
| h | hour |
| LCMS | Liquid Chromatography-Mass Spectrometry |
| m | multiplet |
| MeCN | Acetonitrile |
| mg | milligram |
| min | minute |
| mL | milliliter |
| MHz | megahertz |
| N | Normal |
| NMR | Nuclear Magnetic Ressonance |

TABLE I-continued

List of abbreviations used in the experimental section:

| Abbreviation | Definition |
|---|---|
| PdCl$_2$dppf | [1,1'-Bis(diphenylphosphino)ferrocene]dichloropalladium(II) |
| ppm | part-per-million |
| q | quadruplet |
| RNA | Ribonucleic acid |
| q.d. | quo die (once a day) |
| s | singlet |
| b.i.d. | bis in die (twice daily) |
| shRNA | short hairpin RNA |
| t | triplet |
| TFA | Trifluoroacetic acid |
| THF | Tetrahydrofuran |
| v:v | volume:volume |
| CRP | c-Reactive Protein |
| NRI | nonresponder imputation |
| LOCF | last-observation-carried-forward |
| CFB | Change from baseline |

SYNTHETIC PREPARATION OF THE COMPOUND OF THE INVENTION

Example 1. Preparation of Compound 1

1.1. Route 1

1.1.1. 4-[4-(4,4,5,5-Tetramethyl-[1,3,2]dioxaborolan-2-yl)-benzyl]-thiomorpholine-1,1-dioxide

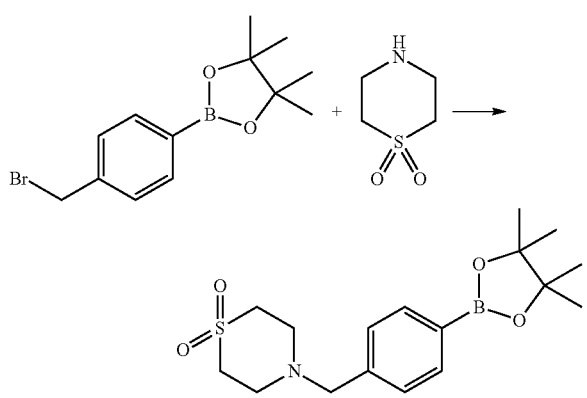

2-(4-Bromomethyl-phenyl)-4,4,5,5-tetramethyl-[1,3,2]dioxaborolane (1 eq) and DIPEA (2 eq) are dissolved in DCM/MeOH (5:1 v:v) under N$_2$ and thiomorpholine 1,1-dioxide (2 eq) is added portionwise. The resulting solution is stirred at room temperature for 16 h. After this time, the reaction is complete. The solvent is evaporated. The compound is extracted with EtOAc and water, washed with brine and dried over anhydrous MgSO$_4$. Organic layers are filtered and evaporated. The final compound is isolated without further purification.

1.1.2. Cyclopropanecarboxylic acid (5-bromo-[1,2,4]triazolo[1,5-a]pyridin-2-yl)-amide

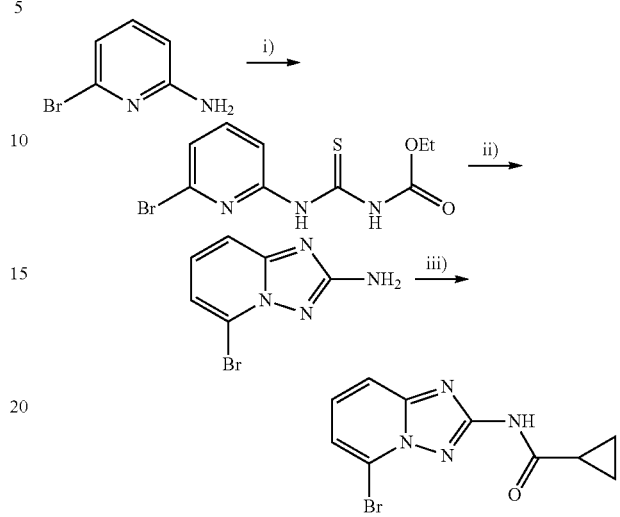

1.1.2.1. Step i): 1-(6-Bromo-pyridin-2-yl)-3-carboethoxy-thiourea

To a solution of 2-amino-6-bromopyridine (1) (253.8 g, 1.467 mol) in DCM (2.5 L) cooled to 5° C. is added ethoxycarbonyl isothiocyanate (173.0 mL, 1.467 mol) dropwise over 15 min. The reaction mixture is then allowed to warm to room temp. (20° C.) and stirred for 16 h. Evaporation in vacuo gives a solid which may be collected by filtration, thoroughly washed with petrol (3×600 mL) and air-dried to afford the desired product. The thiourea may be used as such for the next step without any purification.

$^1$H (400 MHz, CDCl$_3$) δ 12.03 (1H, br s), 8.81 (1H, d), 8.15 (1H, br s), 7.60 (1H, t), 7.32 (1H, dd), 4.31 (2H, q), 1.35 (3H, t).

1.1.2.2. Step ii): 5-Bromo-[1,2,4]triazolo[1,5-a]pyridin-2-ylamine

To a suspension of hydroxylamine hydrochloride (101.8 g, 1.465 mol) in EtOH/MeOH (1:1, 900 mL) is added N,N-diisopropylethylamine (145.3 mL, 0.879 mol) and the mixture is stirred at room temp. (20° C.) for 1 h. 1-(6-Bromo-pyridin-2-yl)-3-carboethoxy-thiourea (2) (89.0 g, 0.293 mol) is then added and the mixture slowly heated to reflux (Note: bleach scrubber is required to quench H$_2$S evolved). After 3 h at reflux, the mixture is allowed to cool and filtered to collect the precipitated solid. Further product is collected by evaporation in vacuo of the filtrate, addition of H$_2$O (250 mL) and filtration. The combined solids are washed successively with H$_2$O (250 mL), EtOH/MeOH (1:1, 250 mL) and Et$_2$O (250 mL) then dried in vacuo to afford the triazolopyridine derivative (3) as a solid. The compound may be used as such for the next step without any purification.

$^1$H (400 MHz, DMSO-d$_6$) δ 7.43-7.34 (2H, m, 2× aromatic-H), 7.24 (1H, dd, J 6.8 and 1.8 Hz, aromatic-H), 6.30 (2H, br, NH2); m/z 213/215 (1:1, M+H+, 100%).

1.1.2.3. Step iii): Cyclopropanecarboxylic acid (5-bromo-[1,2,4]triazolo[1,5-a]pyridin-2-yl)-amide To a solution of the 2-amino-triazolopyridine obtained in the previous step (7.10 g, 33.3 mmol) in dry MeCN (150 mL) at 5° C. is added Et₃N (11.6 mL, 83.3 mmol) followed by cyclopropanecarbonyl chloride (83.3 mmol). The reaction mixture is then allowed to warm to ambient temperature and stirred until all starting material is consumed. If required, further Et₃N (4.64 mL, 33.3 mmol) and cyclopropanecarbonyl chloride (33.3 mmol) is added to ensure complete reaction. Following solvent evaporation in vacuo the resultant residue is treated with 7 N methanolic ammonia solution (50 mL) and stirred at ambient temp. (for 1 h-16 h) to hydrolyse any bis-acylated product. Product isolation is made by removal of volatiles in vacuo followed by trituration with Et₂O (50 mL). The solids are collected by filtration, washed with H₂O (2×50 mL), acetone (50 mL) and Et₂O (50 mL), then dried in vacuo to give the desired compound.

1.1.3. Compound 1

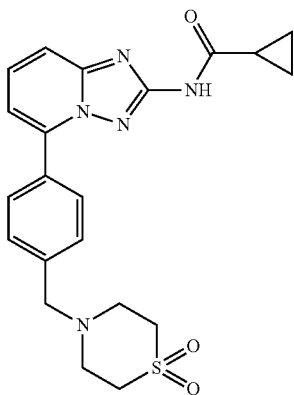

Compound 1

4-[4-(4,4,5,5-Tetramethyl-[1,3,2]dioxaborolan-2-yl)-benzyl]-thiomorpholine-1,1-dioxide (1.1 eq.) is added to a solution of cyclopropanecarboxylic acid (5-bromo-[1,2,4]triazolo[1,5-a]pyridin-2-yl)-amide in 1,4-dioxane/water (4:1). K₂CO₃ (2 eq.) and PdCl₂dppf (0.03 eq.) are added to the solution. The resulting mixture is then heated in an oil bath at 90° C. for 16 h under N₂. Water is added and the solution is extracted with ethyl acetate. The organic layers are dried over anhydrous MgSO₄ and evaporated in vacuo. The final compound is obtained after purification by flash chromatography.

Alternatively, after completion of the reaction, a palladium scavenger such as 1,2-bis(diphenylphosphino)ethane, is added, the reaction mixture is allowed to cool down and a filtration is performed. The filter cake is reslurried in a suitable solvent (e.g. acetone), the solid is separated by filtration, washed with more acetone, and dried. The resulting solid is resuspended in water, aqueous HCl is added, and after stirring at room temperature, the resulting solution is filtered on celite (Celpure P300). Aqueous NaOH is then added to the filtrate, and the resulting suspension is stirred at room temperature, the solid is separated by filtration, washed with water and dried by suction. Finally the cake is re-solubilised in a mixture of THF/H₂O, treated with a palladium scavenger (e.g. SMOPEX 234) at 50° C., the suspension is filtered, the organic solvents are removed by evaporation, and the resulting slurry is washed with water and methanol, dried and sieved, to obtain the desired compound as a free base.

1.2. Route 2

1.2.1. Step 1: cyclopropanecarboxylic acid [5-(4-hydroxymethyl-phenyl)-[1,2,4]triazolo[1,5-a]pyridin-2-yl]-amide

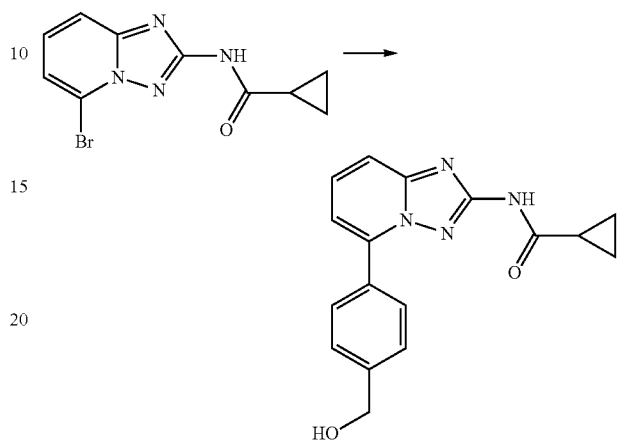

4-(Hydroxymethyl)phenylboronic acid (1.1 eq.) is added to a solution of cyclopropanecarboxylic acid (5-bromo-[1,2,4]triazolo[1,5-a]pyridin-2-yl)-amide in 1,4-dioxane/water (4:1). K₂CO₃ (2 eq.) and PdCl₂dppf (0.03 eq.) are added to the solution. The resulting mixture is then heated in an oil bath at 90° C. for 16 h under N₂. Water is added and the solution is extracted with ethyl acetate. The organic layers are dried over anhydrous MgSO₄ and evaporated in vacuo. The resulting mixture is used without further purification.

1.2.2. Step 2: Cyclopropanecarboxylic acid [5-(4-bromomethyl-phenyl)-[1,2,4]triazolo[1,5-a]pyridin-2-yl]-amide

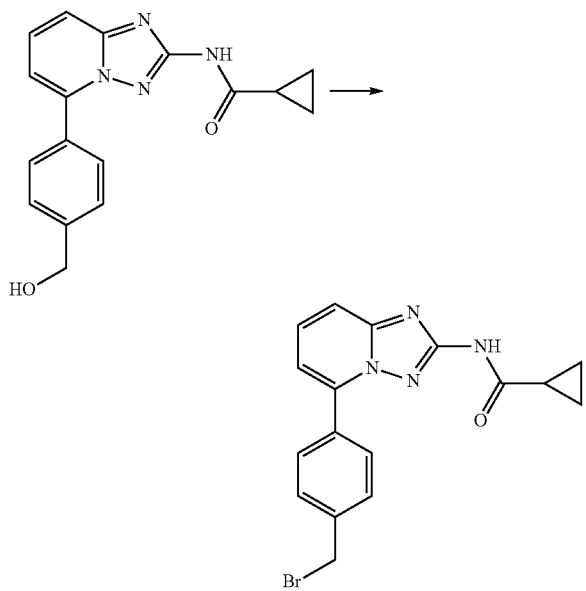

To a solution of cyclopropanecarboxylic acid [5-(4-hydroxymethyl-phenyl)-[1,2,4]triazolo[1,5-a]pyridin-2-yl]- amide (1.0 eq) in chloroform is slowly added phosphorus tribromide (1.0 eq.). The reaction mixture is stirred at room temperature for 20 h, quenched with ice and water (20 mL) and extracted with dichloromethane. The organic layer is dried over anhydrous MgSO$_4$, filtered and concentrated to dryness. The resulting white residue is triturated in dichloromethane/diethyl ether 2:1 to afford the desired product.

1.2.3. Step 3

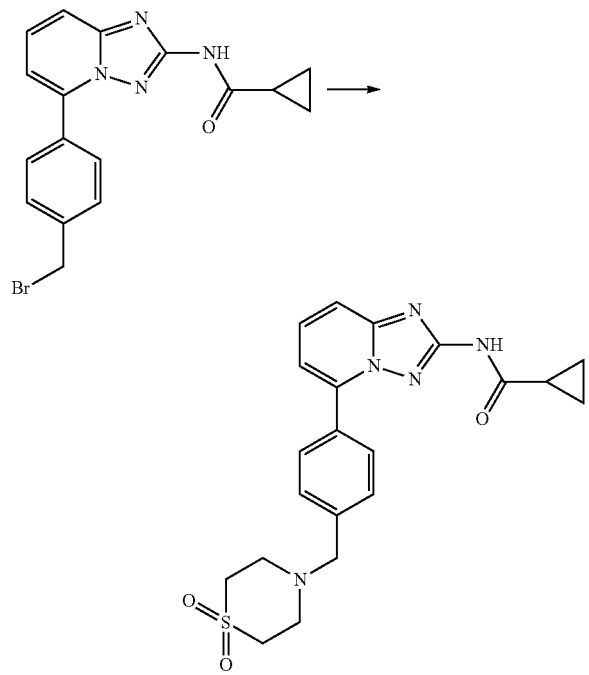

Cyclopropanecarboxylic acid [5-(4-bromomethyl-phenyl)-[1,2,4]triazolo [1,5-a]pyridin-2-yl]-amide (1 eq) and DIPEA (2 eq) are dissolved in DCM/MeOH (5:1 v:v) under N$_2$ and thiomorpholine 1,1-dioxide (1.1 eq) is added dropwise. The resulting solution is stirred at room temperature for 16 h. After this time, the reaction is complete. The solvent is evaporated. The compound is dissolved in DCM, washed with water and dried over anhydrous MgSO$_4$. Organic layers are filtered and evaporated. The final compound is isolated by column chromatography using EtOAc to afford the desired product.

1.3. Preparation of the [Compound 1:HCl:3H$_2$O] Adduct

The identification and preparation of the salt and solvates of Compound 1 are disclosed in PCT application PCT/EP2015/052242.

1.3.1. Protocol 1

To Compound 1 (44 kg, 1.0 eq) under inert atmosphere, is added water (15 rel vol, 1000 L), and the mixture is stirred at 50° C. 3.5 eq. aq HCl (5 rel vol) is added over 10-15 min, at a maximum temperature of 55° C. Upon completion of the addition, the stirring is continued at 50° C. for 15 min, and the reaction is then cooled to 15° C. and stirred at that temperature for at least 12 h but no more than 24 h.

The resulting solid is separated by filtration, and the cake is washed with water (2.0 rel vol), and the cake is dried under nitrogen for at least 4 h to afford the desired product.

1.3.2. Protocol 2

To Compound 1 (45 g, 106 mmol, 1 eq.) under inert atmosphere is added DCM (675 mL) and methanol (225 mL). The resulting suspension is heated to 35° C. under stirring, and trimercaptotriazine trisodium salt 15% in water (22.5 g, 14 mmol, 0.13 eq) is added, and the resulting solution is stirred for 5 h, after which the solution is filtered on 0.45 µm paper under nitrogen pressure.

To the filtrate is added water (50 mL), and the resulting biphasic mixture is stirred at 35° C. for 15 min, after which period the phases are separated, and the organic layer is allowed to cool down to 20° C., and washed twice more with 50 mL water.

The organic layer is cooled down to 15-20° C., then HCl 10% in methanol (42.4 g, 116 mmol, 1.10 eq.) is added over 30 min, causing the precipitation of a solid. The suspension is further stirred at 20° C. for 3 h, then the precipitate is isolated by filtration, the cake is washed with methanol (2×50 mL) to afford the desired compound, which is dried under vacuum at 45° C. for 3 h. The cake is then resuspended in water (220 mL) and stirred for 6 h at 50° C., and then cooled to 15-20° C. The resulting solid is separated by filtration and the cake is washed with water (2×30 mL), and dried at 45° C. for 3 h to afford the desired product.

1.3.3. Protocol 3

1.3.3.1. Step 1: Compound 1.HCl.MeOH

To Compound 1 (100 g, 235 mmol, 1 eq.) suspended in DCM (1.5 L), is added MeOH (0.5 L), and the resulting solution is heated to 35° C. Trimercaptotriazine trisodium 85% (8.7 g, 3 mmol, 0.13 eq.) in water (42 mL) is added and the resulting mixture is stirred at 35° C. for at least 5 h. The solution is then filtered on a 0.45 µm paper filter under nitrogen pressure.

To the resulting solution is added water (150 g), stirred at 35° C. for 15 to 30 min, and the biphasic mixture is separated. The organic layer is washed again twice with water (2×150 g).

Finally, a solution of HCl in MeOH (10% w/w) (141 g) is added, and the suspension is stirred at 20° C. for 3 h, and the resulting solid is separated by filtration, the cake is washed with MeOH (2×118 g), dried under vacuum for 3 h at 45° C., to afford Compound 1.HCl.MeOH.

1.3.3.2. Step 2: Compound 1.HCl.3H$_2$O

To formic acid (200 g, 1.6 eq) in water (36 g, 0.4 eq.) is added Compound 1.HCl.MeOH (100 g, 1 eq.) obtained in Step 1 above. The resulting mixture is heated to 55° C. under stirring, and the solution is filtered through a 0.45 µm filter cartridge. Formic acid 85% aq (200 g) is added, and the mixture is cooled to 28-32° C. under gentle stirring.

Water (100 g) is then added, followed with Compound 1.HCl.3H$_2$O (1 g) causing the precipitation of Compound 1.HCl.1.5HCO$_2$H.

Under stirring at 28-32° C., water (2 L) is added portionwise in 8 portions of 100 mL, 1 portion of 200 mL, and 2 portions of 500 mL.

The resulting suspension is then filtered, the cake is washed with water (2×100 mL) and dried at 30-35° C. to yield Compound 1.HCl.3H$_2$O.

Biological Examples

The compound of the invention according to Formula I has been extensively profiled, and data are disclosed in WO 2010/149769 (Menet and Smits, 2010). The synthesis of the salt and suitable formulations have been described in PCT/EP2015/052239, and in PCT/EP2015/052242.

Similarly, the compound of the invention according to Formula I has been extensively profiled, and data are disclosed in WO 2013/189771 (Van't Klooster et al., 2013).

Example 2. Clinical Setting 2.1. Study 1—RA Patients with Inadequate Response to Methotrexate 2.1.1. Study Design Double-blind, placebo-controlled add on study in subjects with moderately to severely active RA who have an inadequate response to methotrexate (MTX) (oral or parenteral).

595 subjects randomized to one of 6 dose regimens of Compound 1 (dosed as a [Compound 1:HCl:3H$_2$O]) (3 dose levels administered either once or twice daily) or placebo on top of each subject's stable dose of MTX.

2.1.2. Study Duration

Treatment duration: 24 weeks.

2.1.3. Treatment

Compound 1 (dosed as a [Compound 1:HCl:3H$_2$O]) is dosed for twelve weeks once daily (q.d.) (50 mg, 100 mg or 200 mg) or twice daily (b.i.d.) (25 mg, 50 mg or 100 mg); or placebo.

At Week 12, the subjects on placebo who have not achieved 20% improvement in swollen joint count (SJC66) and tender joint count (TJC68) are re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who have not achieved 20% improvement in SJC66 and TJC68 will be assigned to 100 mg q.d. and subjects on 25 mg b.i.d. that have not achieved a 20% improvement in SJC66 and TJC68 will be assigned to 50 mg b.i.d. Subjects who switch treatment at week 12 are handled as if they discontinued at week 12 for the purpose of statistical analysis, whereas subjects in the other groups will maintain their randomized treatment until Week 24.

2.1.4. Participants 2.1.4.1. Main Inclusion Criteria male or female subjects who are ≥18 years of age, on the day of signing informed consent,
diagnosis of RA at least 6 months prior to screening and meeting the 2010 ACR/EULAR criteria of RA and ACR functional class I-III (Aletaha et al., 2010),
≥6 swollen joints (from a 66 joint count) and ≥8 tender joints (from a 68 joint count) at Screening and at Baseline,
screening serum c-reactive protein (CRP)≥0.7× upper limit of laboratory normal range (ULN),
on MTX for ≥6 months and on a stable dose (15 to 25 mg/week) of MTX for at least 4 weeks prior to Screening and continued on their current regimen for the duration of the study. Stable doses of MTX as low as 10 mg/week are allowed when there is documented evidence of intolerance or safety issues at higher doses.

2.1.4.2. Main Exclusion Criteria current therapy with any disease-modifying anti-rheumatic drugs (DMARD) other than MTX, including oral or injectable gold, sulfasalazine, antimalarials, azathioprine, or D-penicillamine within 4 weeks prior to Baseline, cyclosporine within 8 weeks prior to Baseline, and leflunomide within 3 months prior to Baseline or a minimum 4 weeks prior to Baseline if after 11 days of standard cholestyramine therapy,
current or previous RA treatment with a biologic DMARD, with the exception of biologic DMARDs administered in a single clinical study setting more than 6 months prior to Screening (12 months for rituximab or other B cell depleting agents), where the biologic DMARD was effective, and if discontinued, this should not be due to lack of efficacy,
previous treatment at any time with a cytotoxic agent, other than MTX, before Screening.

2.2. Study 2—RA Patients Monotherapy with Compound 1

2.2.1. Purpose of the Study

Randomized, double-blind, placebo-controlled, multicenter, phase IIb dose finding study of Compound 1 (dosed as a [Compound 1:HCl:3H$_2$O]) administered for 24 weeks as monotherapy to subjects with moderately to severely active rheumatoid arthritis who have an inadequate response to methotrexate alone 2.2.2. Study Design Double-blind, placebo-controlled, monotherapy study in subjects with moderately to severely active RA who have an inadequate response to methotrexate (MTX) (oral or parenteral).

280 subjects randomized to one of 3 doses of Compound 1 (dosed as a [Compound 1:HCl:3H$_2$O]) or to placebo, given once daily (q.d.).

2.2.3. Study Duration

Treatment duration: 24 weeks.

2.2.4. Treatment

Twelve weeks of treatment with Compound 1 (dosed as a [Compound 1:HCl:3H$_2$O]) at 50 mg, 100 mg, or 200 mg q.d.; or placebo. At Week 12, all subjects on placebo and the subjects on the 50 mg dose who have not achieved 20% improvement in swollen joint count (SJC66) and tender joint count (TJC68) will be assigned to 100 mg q.d. in a blinded fashion and will continue treatment until Week 24. Subjects in the other groups will maintain their randomized treatment until Week 24.

2.2.5. Participants

2.2.5.1. Main Inclusion Criteria male or female subjects who are ≥18 years of age on the day of signing informed consent,
diagnosis of RA since at least 6 months prior to Screening and meeting the 2010 ACR/EULAR criteria of RA and ACR functional class I-III,
≥6 swollen joints (from a 66-joint count) and ≥8 tender joints (from a 68-joint count) at Screening and at Baseline,
Screening serum c-reactive protein (CRP)≥0.7× upper limit of laboratory (reference) normal range (ULN),
inadequate response in terms of either lack of efficacy or toxicity to MTX,
washed out from MTX for a period of at least 4 weeks before or during the Screening period.

2.2.5.2. Main Exclusion Criteria modifying anti-rheumatic drug (DMARD), including oral or injectable gold, sulfasalazine, azathioprine, or D penicillamine within 4 weeks prior to Baseline, cyclosporine within 8 weeks prior to Baseline, and leflunomide within 3 months prior to Baseline or a minimum 4 weeks prior to Baseline if after 11 calendar days of standard cholestyramine therapy, with the exception of antimalarials, which must be at a stable dose for at least 12 weeks prior to Baseline,
current or previous RA treatment with a biologic DMARD, with the exception of biologic DMARDs: administered in a single clinical study setting, and; more than 6 months prior to Screening (12 months for rituximab or other B cell depleting agents), and; where the biologic DMARD was effective, and if discontinued, this should not be due to lack of efficacy,
previous treatment at any time with a cytotoxic agent, other than MTX, before Screening.

2.3. Study 3—Healthy Volunteers

2.3.1. Purpose of the Study

Randomized, double-blind, placebo-controlled study for the assessment of safety, tolerability, pharmacokinetics, and pharmacodynamics, of multiple oral doses of Compound 1 (dosed as a [Compound 1:HCl:3H$_2$O]) in Japanese and Caucasian healthy subjects.

2.3.2. Study Design

Randomized, double-blind, placebo-controlled, single center, sequential design study.

2.3.3. Study Duration

Approximately 6 weeks

2.3.4. Treatment

Compound 1 (dosed as a [Compound 1:HCl:3H$_2$O]) is administered for 10 days as oral film-coated tablet (25 and 100 mg and matching placebos). Placebo are provided as a matching tablet.
The study drug is ingested with 240 mL water after a standardized breakfast on Days 2-9. On PK days (Day 1 and Day 10) the study drug is administered in a fasted state (subjects will receive lunch 4 h after dosing on Day 1 and Day 10).

2.3.5. Participants

2.3.5.1. Panel Contingent

Subjects are enrolled according to the inclusion and exclusion criteria below and divided into three panels:
Panel 1:
8 Japanese subjects receive once daily an oral dose of 50 mg Compound 1 (dosed as a [Compound 1:HCl:3H$_2$O]) or matching placebo (6 active, 2 placebo) as two tablets of 25 mg or matching placebo for 10 days.
Panel 2:
8 Japanese subjects receive once daily an oral dose of 100 mg Compound 1 (dosed as a [Compound 1:HCl:3H$_2$O]) or matching placebo (6 active, 2 placebo) as one tablet of 100 mg or matching placebo for 10 days.
Panel 3:
10 Japanese subjects (6 active, 4 placebo) and 10 Caucasian subjects (6 active, 4 placebo) will receive once daily an oral dose of 200 mg Compound 1 (dosed as a [Compound 1:HCl:3H$_2$O]) or matching placebo as two tablets of 100 mg or matching placebo for 10 days. For practical reasons, these subjects may be split over separate groups, each group consisting of an equal number of Japanese and Caucasian Compound 1 (dosed as a [Compound 1:HCl:3H$_2$O]) treated subjects and Japanese and Caucasian placebo subjects.

2.3.5.2. Main Exclusion Criteria modifying anti-rheumatic drug (DMARD), including oral or injectable gold, sulfasalazine, azathioprine, or D penicillamine within 4 weeks prior to Baseline, cyclosporine within 8 weeks prior to Baseline, and leflunomide within 3 months prior to Baseline or a minimum 4 weeks prior to Baseline if after 11 calendar days of standard cholestyramine therapy, with the exception of antimalarials, which must be at a stable dose for at least 12 weeks prior to Baseline,
current or previous RA treatment with a biologic DMARD, with the exception of biologic DMARDs: administered in a single clinical study setting, and; more than 6 months prior to Screening (12 months for rituximab or other B cell depleting agents), and; where the biologic DMARD was effective, and if discontinued, this should not be due to lack of efficacy,
previous treatment at any time with a cytotoxic agent, other than MTX, before Screening.

2.3.6. Endpoints

Pharmacokinetics (Plasma concentrations, Cmax, tmax, $C_{24h}$, AUC, Ae, CLR, t1/2,λ,z, the metabolite over parent exposure ratio (R), and the accumulation ratio (Rac)). Dose normalized parameters (Cmax/dose, C24 h/dose AUC/dose, Ae/dose).
Pharmacodynamics (only for Panel 3): (JAK/STAT, Whole blood assay, IL-6/STAT1, IL-6/STAT3 phosphorylation, or GM-CSF/STATS phosphorylation determination).

2.4. Study 4—4 Weeks Study in RA Patients with Inadequate Response to Methotrexate Purpose of the Study Randomized, double-blind, placebo-controlled, multi-center, phase II study of Compound 1 (dosed as a [Compound 1:HCl:3H$_2$O]) to compare four dose regimens versus placebo, in combination with methotrexate, administered for 4 weeks in the treatment of subjects with active rheumatoid arthritis who have an inadequate response to methotrexate alone.

2.4.2. Study Design

Randomized double-blind, placebo-controlled add on study in subjects with active RA who have an inadequate response to MTX monotherapy, in combination with methotrexate, administered for 4 weeks in the treatment of subjects with active rheumatoid arthritis who have an inadequate response to methotrexate alone.

90 subjects randomized to one of 4 dose regimens of Compound 1 (dosed as a [Compound 1:HCl:3H$_2$O]) or placebo, on top of their stable dose of MTX. Thus, each of the 4 different doses of Compound 1 (dosed as a [Compound 1:HCl:3H$_2$O]) and placebo groups has 18 subjects.

2.4.3. Study Duration

Treatment duration: 4 weeks.

2.4.4. Treatment

Compound 1 (dosed as a [Compound 1:HCl:3H$_2$O]) capsules administered orally in 30 mg, 75 mg, 150 mg, or 300 mg doses per day for 4 weeks.

Placebo capsules administered orally daily for 4 weeks.

2.4.5. Participants

2.4.5.1. Main Inclusion Criteria

Male or female subjects who are 18 to 70 years of age, on the day of signing informed consent,
Fulfill the revised 1987 American Rheumatism Association (ARA) criteria for the classification of RA,
Have ≥5 swollen joints (from a 66 joint count) and ≥5 tender joints (from a 68 joint count), and a serum CRP≥1.0 mg/dL,
Have received MTX for >12 weeks and be on a stable dose (7.5 mg/week to 25 mg/week [extremes included]) of MTX for at least 4 weeks prior to screening and willing to continue on this regimen for the duration of the study,
If taking oral steroids, these should be at a dose ≤10 mg/day of prednisone or prednisone equivalent and stable for at least four weeks prior to screening,
If taking non-steroidal anti-inflammatory drugs (NSAIDs), these must be at a stable dose for at least two weeks prior to screening,
The results of the following laboratory tests performed at the central laboratory at screening must be within the limits specified below:
  a. Hemoglobin ≥8.5 g/dL (International System of Units [SI]: ≥85 g/L);
  b. White blood cells ≥3.0×10$^3$ cells/mm3 (SI: ≥3.0× 10$^9$ cells/L);
  c. Neutrophils ≥1.5×10$^3$ cells/mm$^3$ (SI: ≥1.5×10$^9$ cells/L);
  d. Platelets ≥100×10$^3$ cells/mm3 (SI: ≥100×10$^9$ cells/L);
  e. Serum alanine aminotransferase (ALT) and aspartate aminotransferase (AST)≤1.5×upper limit of laboratory normal range (ULN); and
  f. Total bilirubin level≤1.25×ULN;
  g. Lipase and amylase within normal range.

2.4.5.2. Main Exclusion Criteria

Current therapy with any disease modifying anti-rheumatic drug (DMARD) other than MTX, including oral or injectable gold, sulfasalazine, hydroxychloroquine, azathioprine, or D penicillamine within four weeks prior to screening, cyclosporine within eight weeks prior to screening, and leflunomide within three months prior to screening,
Current or previous RA treatment with a biological agent, with the exception of biologics administered in a single clinical study setting more than six months prior to screening (12 months for rituximab or other B cell depleting agents),
Previous treatment at any time with a cytotoxic agent, other than MTX, before screening. These agents include, but are not limited to chlorambucil, cyclophosphamide, nitrogen mustard, or other alkylating agents,
Previous use of the study drug, Compound 1,
Receipt of an intra-articular or parenteral corticosteroid injection within four weeks prior to screening.

2.5. Study 5: Crohn's Disease Study with Monotherapy of Compound 1

2.5.1. Purpose of the Study

Double-Blind, Randomized, Placebo-Controlled, Multi-Centre Study to Investigate the Efficacy and Safety of Compound 1 in Subjects With Active Crohn's Disease With Evidence of Mucosal Ulceration.

2.5.2. Study Design

This is a double-blind, randomized, placebo-controlled, multi-centre Phase 2 study to investigate the efficacy and safety of Compound 1 administered once daily for the treatment of active CD with evidence of mucosal ulceration. The pharmacokinetics (including a PK substudy) and pharmacodynamics of Compound 1 and metabolite in CD will also be characterised.

A total of 180 eligible subjects will be randomized to receive Compound 1 or placebo in addition to their stable background treatment (eg, corticosteroids, aminosalicylates, or CD-related antibiotics). The study will consist of 2 parts, with total treatment duration of 20 weeks. Randomization in Part 1 will be stratified according the subject's previous anti-TNF exposure/response, CRP level at Screening, and oral corticosteroid use at visit Day −1.

After the first 10 weeks of treatment in Part 1, patients will be re-randomized for Part 2 as shown in the diagram below and will be stratified according to the subject's clinical response, previous anti-TNF exposure/response, and oral corticosteroid use at visit Day −1.

2.5.3. Study Duration

Maximum of 27 weeks: up to 28 days for Screening, up to 20 weeks for treatment, and 2 weeks for follow-up (+5 days visit window, if applicable).

2.5.4. Treatment

A diagram of the study design is shown in Table II below:

TABLE II

Study design

| Week 1-10 | Re-randomization | Week 10-20 |
|---|---|---|
| Placebo (1)* | Responder** | Placebo |
|  | Non responder | 100 mg q.d. Compound 1 |
| 200 mg q.d. of Compound 1 (3)* | Responder** | 200 mg q.d. Compound 1 (2)* |
|  |  | 100 mg q.d. Compound 1 (2)* |
|  |  | Placebo (1)* |
|  | Non responder | 200 mg q.d. Compound 1 (3)* |
|  |  | Placebo (1)* |

*Randomisation Ratio
**Reduction in CDAI of 100 points

2.5.5. Participants

2.5.5.1. Main Inclusion Criteria

Subjects should have all of the following conditions at to be eligible for admission into the study:

1. Male or female subjects between the ages of 18 and 75 years, on the day of signing informed consent.
2. Documented history of ileal, colonic, or ileocolonic CD (at least 3 months prior Screening) as assessed by colonoscopy, and supported by histological assessment.
3. Crohn's Disease Activity Index (CDAI) score during Screening ≥220 to ≤450.
4. Evidence of active inflammation at Screening as demonstrated by endoscopic confirmation of active disease (based on central reading) with evidence of ulceration corresponding to a score of 1 in at least 1 of the 5 ileocolonic segments on the Presence of Ulcers subscore of the Simplified Endoscopy Score for CD (SES CD) and total score of at least 7.
5. Treatment with oral steroids (≤30 mg prednisolone equivalent/day or budesonide dose ≤9 mg/day) is allowed, if at a stable dose since at least 2 weeks prior to the first dose of study drug.
6. Subjects previously not exposed to anti-TNF treatment (eg, TNF-naïve) or subjects previously exposed to anti-TNF therapy (infliximab, adalimumab or certolizumab pegol) at a dose registered for the treatment of CD that has been discontinued at least 8 weeks prior to Baseline. Subjects deemed by the treating physician as a primary or secondary non-responder or intolerant to anti-TNF treatment or responders to anti-TNF treatment, where treatment was stopped for other reasons (TNF-experienced) can also be included.
7. Subjects are allowed to continue on concurrent treatment with the following agents:
    a. Mesalazine and olsalazine if stable dosage for at least 4 weeks prior to Screening (same dosage to be maintained throughout the study). Previous exposure to sulfasalazine is permitted but must be discontinued at least 4 weeks prior to Screening in male subjects.
    b. Crohn's Disease-related antibiotics if stable dosage for at least 4 weeks prior to Screening and no discontinuation in the 14 days prior to the first dose of study drug.
    c. Probiotics if stable dosage for 2 weeks prior to the first dose of study drug.
8. Previous exposure to immunomodulators (e.g. thiopurines and methotrexate) is permitted, but must be discontinued (and agreed by the subject) at least 25 days prior to the first dose of the study drug. Subjects whose immunomodulators (e.g. thiopurines and methotrexate) were discontinued prior to Screening are also permitted to participate. In these cases documented evidence for the reasons of discontinuation should be provided.
9. The results of the following laboratory tests during Screening must be as specified below:
    a) Haemoglobin ≥9 g/dL (International System of Units [SI]: ≥90 g/L)
    b) White blood cells (WBCs) ≥3.0×10$^9$ cells/L
    c) Neutrophils ≥2.0×10$^9$ cells/L
    d) Lymphocytes ≥0.5×10$^9$ cells/L
    e) Platelets ≥100×10$^9$ cells/L
    f) Serum alanine transaminase (ALT) and aspartate transaminase (AST)≤1.5×ULN
    g) Total bilirubin level ≤1.5×ULN
    h) Alkaline phosphatase ≤1.5×ULN
    i) Lipase ≤1.5×ULN and amylase ≤1.5×ULN
    j) Creatinine clearance >60 mL/min. Creatinine clearance will be calculated using the Cockroft-Gault formula.
10. Women of childbearing potential must have a negative blood pregnancy test, unless they are surgically sterile, had a hysterectomy, or have been postmenopausal for at least 1 year (12 consecutive months without menses); in case of doubt a determination of serum follicle-stimulating hormone (FSH) can be done with FSH levels >35 mIU/mL confirming menopause status.
11. Subjects willing to use highly effective contraceptive methods prior to the first dose of the study drug, during the study and for at least 12 weeks after the last dose of the study drug.
    a) If the subject is a sexually active woman of childbearing potential, she and her male partner are required to simultaneously use two effective contraceptive methods as listed in section 10.4.8.1.2 of the protocol. Female subjects who wish to use non-hormonal contraception must have done so for at least 14 days prior to the first dose of the study drug.
    b) Non-vasectomized males with female partners of childbearing potential must be willing to use a condom in addition to having their female partner using another form of contraception as listed in section 10.4.8.1.3 of the protocol.
12. Able and willing to give voluntary written informed consent and meet all of the inclusion and none of the exclusion criteria before being enrolled in the study. The subjects must sign the informed consent form prior to any study related procedures and agree to the schedule of assessments (including 2 colonoscopies).
13. Judged to be in good health, except for their CD, as determined by the Investigator based upon the results of medical history, laboratory profile, physical examination, chest X-ray, and a 12-lead electrocardiogram (ECG) performed during Screening.

2.5.5.2. Main Exclusion Criteria

Subjects who exhibit any of the following conditions at screening will not be eligible for admission into the study:
1. Diagnosis of indeterminate colitis, ulcerative colitis (UC), or clinical findings suggestive of UC.

2. Stoma, gastric or ileanal pouch, proctocolectomy or total colectomy, symptomatic stenosis or obstructive strictures, abscess or suspected abscess, history of bowel perforation.
3. Subject who has had surgical bowel resections within the past 6 months or is planning any resection at any time point while enrolled in the study.
4. Subject who has short bowel syndrome.
5. Subject who is receiving tube feeding, defined formula diets, or total parenteral alimentation.
6. Subjects with positive *Clostridium difficile* (*C. difficile*) toxin stool assay or test positive for stool culture of enteric pathogens, ova or parasites during the screening period.
7. Subject has received nonsteroidal anti-inflammatory drugs (NSAIDs) within 14 days prior to Screening or during screening period.
8. Subject has received therapeutic enema or suppository, other than required for colonoscopy, within 7 days prior to Screening or during screening period.
9. Subject has received intravenous corticosteroids within 14 days prior to Screening or during screening period.
10. If non-systemic steroids are being used for other conditions than CD, subjects may be included at the discretion of the Investigator after discussion with the Medical Monitor.
11. Treatment with cyclosporine, mycophenolate mofetil, tacrolimus, or interferon within 10 weeks prior to Screening or during screening period.
12. Any prior treatment with lymphocyte-depleting agents (such as CamPath®[Alemtuzumab]). Also subjects who have previously received either lymphocyte apheresis or selective monocyte granulocyte apheresis (eg Cellsobra®) within 12 months prior to Screening or during screening period.
13. Subjects who have previously received fecal microbiota transplants or stem cell transplantation.
14. Subjects who have received previous treatment with investigational chemical agents within 4 weeks prior to Screening or during screening period.
15. Subjects who have previously received treatment with biological investigational medicinal products including murine, chimeric or humanized monoclonal antibodies or a chemokine receptor blocker within less than 5 half-lives prior to Baseline. Previous treatment with a janus kinase inhibitor is prohibited.
16. Known hypersensitivity to study drug ingredients or a significant allergic reaction to any drug as determined by the Investigator, such as anaphylaxis requiring hospitalization.
17. Subject with a previous history of dysplasia of the gastrointestinal tract (high or low grade, flat or raised including discrete adenoma-like dysplasia or indefinite dysplasia) or found to have above described dysplasia in any biopsy performed during the Screening colonoscopy.
18. Concurrent gastro-intestinal (GI) malignancy or a history of cancer elsewhere (other than basal cell carcinoma or carcinoma in situ of the cervix successfully treated more than 5 years prior to the initial study drug administration).
19. History of lymphoproliferative disease; or signs and symptoms suggestive of possible lymphoproliferative disease including lymphadenopathy or splenomegaly.
20. Positive serology for human immunodeficiency virus (HIV) 1 or 2 or hepatitis B or C, or any history of HIV or hepatitis from any cause with the exception of hepatitis A.
21. Known active infection of any kind (excluding fungal infections of nail beds), or any major episode of infection requiring hospitalization or treatment with parenteral (intramuscular or IV) anti-infectives (antibiotics, antiviral, anti-fungals or anti-parasitic agents) within 4 weeks of the Screening visit or completion of oral anti-infectives within 2 weeks of the Screening visit (except Crohn's disease-related antibiotics) Immunocompromised subjects who in the opinion of the investigator are at an unacceptable risk for participating in the study.
22. Previous history of symptomatic herpes zoster or herpes simplex infection within 12 weeks prior to Screening or have a history of disseminated/complicated herpes zoster infection (multi-dermatomal involvement, ophthalmic zoster CNS involvement, or postherpetic neuralgia).
23. History of invasive infection (e.g., listeriosis, histoplasmosis).
24. Significant blood loss (>500 mL) or transfusion of any blood product within 4 weeks prior to Screening.
25. Currently on any therapy for chronic infection (such as *pneumocystis*, CMV, herpes simplex, herpes zoster, or atypical mycobacteria).
26. History of active or latent tuberculosis (TB) infection as determined by:
    a. positive diagnostic TB test result (defined as a positive QuantiFERON TB Gold test) OR
    b. a chest X-ray radiograph (both posterior-anterior and lateral views), taken within 3 months prior to Screening or at Screening and read by a qualified radiologist, with evidence of current active TB or old inactive TB.
27. Administration of a live vaccine within 90 days or an attenuated vaccine within 30 days prior to the initial study drug administration.
28. History within the previous year or current evidence of drug or alcohol abuse according to the opinion of the investigator.
29. Currently pregnant or breastfeeding or not willing to maintain birth control methods for at least 12 weeks after last study drug administration.
30. Medical, psychiatric, cognitive, or other conditions that, according to the Investigator's medical judgment, compromise the subject's ability to understand the subject information, to give informed consent, to comply with the requirements of the study protocol (that is likely to affect the subject's return for visits on schedule), or ability to complete the study.
31. If applicable to national or local legislation: history of being admitted to an institution under an administrative or court order.
32. Any concurrent illness, disability, or clinically significant abnormality (including laboratory tests) that may affect the interpretation of clinical safety or efficacy data or prevent the subject from safely completing the assessments required by the protocol as judged by the Investigator.

Example 3. In Vivo Assays

The following assays were conducted at Eurofins Global Central Laboratory, Bergschot 71, 4817 PA Breda, The Netherlands, and at Quest Diagnostics, Clinical Trials, Quest House, 125-135 Staines Road, Hounslow, Middlesex, TW3 3JB, United Kingdom. The assays for Study 5 were performed at BARC Europe, 3B, Industrie Park, Zwijnaarde, B-9052 Ghent, Belgium.

3.1. Cholesterol Determination (Total Cholesterol+ [HDL]+[LDL])

Cholesterol level determinations are widely available, and the following methods are provided as non-exclusive general protocols.

3.1.1. Cholesterol Determination

Total cholesterol determination is available at Quest Diagnostics, Clinical Trials, Quest House, 125-135 Staines Road, Hounslow, Middlesex, TW3 3JB, United Kingdom. Under Catalogue n#82465.

This method is based on the determination of $\Delta^4$ cholestenone after enzymatic cleavage of the cholesterol ester by cholesterol esterase, conversion of cholesterol by cholesterol oxidase, and subsequent measurement by the Trinder reaction of the hydrogen peroxide formed (Allain et al., 1974).

Cholesterol esters are cleaved by the action of cholesterol esterase to yield free cholesterol and fatty acids. Cholesterol oxidase then catalyzes the oxidation of cholesterol to cholest-4-en-3-one and hydrogen peroxide. In the presence of peroxidase, the hydrogen peroxide formed effects the oxidative coupling of phenol and 4-aminophenazone to form a red quinone-imine dye. The color intensity of the dye formed is directly proportional to the cholesterol concentration. It is determined by measuring the increase in absorbance.

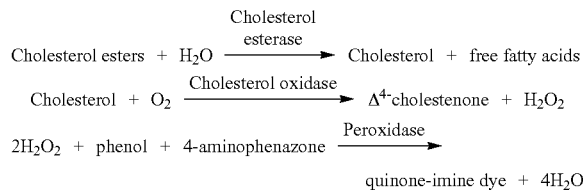

3.1.1.1. Assay

Human serum and plasma samples cholesterol determination was done on a Roche/Hitachi Cobas c 701/702 system which automatically calculate the analyte concentration of each sample.

Samples containing precipitates are centrifuged before performing the assay.

The Cobas c 701/702 machine parameters are listed in Table III below.

TABLE III

| Cobas c 701/702 test parameters for cholesterol determination | |
|---|---|
| Assay type | 1 Point |
| Reaction time/Assay points | 10/38 |
| Wavelength (sub/main) | 700/505 nm |
| Reaction direction | Increase |
| Units | mmol/L (mg/dL, g/L) |
| Reagent pipetting | Diluent (H$_2$O) |
| PIPES buffer: 225 mmol/L, pH 6.8; Mg2+: 10 mmol/L; sodium cholate: 0.6 mmol/L; 4-aminophenazone: ≥0.45 mmol/L; phenol: ≥12.6 mmol/L; fatty alcohol polyglycol ether: 3%; cholesterol esterase (*Pseudomonas* spec.): ≥25 μkat/L (≥1.5 U/mL); cholesterol oxidase ≥7.5 μkat/L (≥0.45 U/mL); peroxidase (horseradish): ≥12.5 μkat/L (≥0.75 U/mL); stabilizers; preservative | 47 μL + H$_2$O (93 μL) |

| Sample volumes | Sample dilution | Diluent (NaCl) |
|---|---|---|
| Normal (2 μL) | — | — |
| Decreased (4 μL) | 15 μL | 135 μL |
| Increased (4 μL) | — | — |

As disclosed in the respective study protocols for Study 1 or 2, at week 12, depending on the outcome of their treatment, the subjects may be continued in their initial treatment course, or reassigned to another treatment group in a randomized blinded fashion until week 24. Therefore, the number of subjects (N) for the period of either 12 weeks, or 24 weeks is provided to reflect this redistribution at week 12.

Namely, in Study 1, at Week 12, the subjects on placebo who did not achieve at least a 20% improvement in swollen joint count (SJC66) and tender joint count (TJC68) were re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

In Study 2, at Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.

3.1.1.2. Results

3.1.1.2.1 Study 1

TABLE IV

| | [total cholesterol] Mean CFB (mmol/L) - 12 weeks results | | | | | | |
|---|---|---|---|---|---|---|---|
| | | q.d. groups | | | b.i.d. groups | | |
| Weeks | Placebo (N = 86) | 50 mg (N = 82) | 100 mg (N = 85) | 200 mg (N = 86) | 2 x 25 mg (N = 86) | 2 x 50 mg (N = 85) | 2 x 100 mg (N = 84) |
| 0 | 0.0 | 0.0 | 0.0 | 0.0 | 0.0 | 0.0 | 0.0 |
| 1 | −0.1 | 0.0 | 0.2 | 0.3 | 0.1 | 0.1 | 0.3 |

TABLE IV-continued

[total cholesterol] Mean CFB (mmol/L) - 12 weeks results

| | q.d. groups | | | b.i.d. groups | | |
|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 2 | −0.1 | 0.1 | 0.1 | 0.3 | 0.1 | 0.1 | 0.4 |
| 4 | 0.0 | 0.1 | 0.2 | 0.4 | 0.1 | 0.3 | 0.4 |
| 8 | 0.0 | 0.1 | 0.1 | 0.4 | 0.1 | 0.2 | 0.6 |
| 12 | −0.1 | 0.2 | 0.2 | 0.5 | 0.2 | 0.2 | 0.6 |

TABLE V

[total cholesterol] Median CFB (mmol/L) - 12 weeks results

| | q.d. groups | | | b.i.d. groups | | |
|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0.0 | 0.0 | 0.0 | 0.0 | 0.0 | 0.0 | 0.0 |
| 1 | −0.11 | 0.05 | 0.14 | 0.25 | 0.12 | 0.21 | 0.28 |
| 2 | −0.10 | 0.04 | 0.07 | 0.34 | 0.10 | 0.18 | 0.31 |
| 4 | 0.02 | 0.06 | 0.25 | 0.33 | 0.05 | 0.28 | 0.45 |
| 8 | 0.00 | 0.16 | 0.09 | 0.54 | 0.05 | 0.22 | 0.55 |
| 12 | −0.05 | 0.20 | 0.30 | 0.26 | 0.13 | 0.23 | 0.80 |

TABLE VI

[total cholesterol] Mean CFB (mmol/L) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| Placebo | Continued (N = 56) | 0.00 | 0.02 | −0.01 | 0.13 | 0.08 | −0.08 | −0.15 | −0.09 | −0.13 |
| | Switched to 100 mg q.d. at week 12 (N = 15) | 0.00 | −0.32 | −0.39 | −0.25 | −0.31 | −0.44 | −0.16 | −0.17 | −0.26 |
| | Switched to 50 mg b.i.d at week 12 (N = 15) | 0.00 | −0.30 | −0.34 | −0.14 | −0.05 | 0.02 | 0.08 | 0.18 | 0.06 |
| Continued q.d. dosage regimen over 24 weeks | 50 mg q.d. (N = 63) | 0.00 | 0.03 | −0.01 | 0.05 | 0.14 | 0.24 | 0.21 | 0.20 | 0.28 |
| | 100 mg q.d. (N = 85) | 0.00 | 0.15 | 0.10 | 0.23 | 0.14 | 0.23 | 0.06 | 0.13 | 0.21 |
| | 200 mg q.d. (N = 86) | 0.00 | 0.26 | 0.29 | 0.37 | 0.44 | 0.46 | 0.37 | 0.43 | 0.39 |
| Continued b.i.d. dosage regimen over 24 weeks | 25 mg b.i.d (N = 69) | 0.00 | 0.11 | 0.12 | 0.14 | 0.15 | 0.26 | 0.20 | 0.27 | 0.24 |
| | 50 mg b.i.d. (N = 85) | 0.00 | 0.15 | 0.14 | 0.28 | 0.21 | 0.23 | 0.24 | 0.32 | 0.34 |
| | 100 mg b.i.d. (N = 84) | 0.00 | 0.30 | 0.36 | 0.43 | 0.64 | 0.64 | 0.56 | 0.54 | 0.66 |
| Increased dosage regimen at 12 weeks | from 50 mg q.d. to 100 mg q.d. (N = 19) | 0.00 | 0.05 | 0.26 | 0.11 | 0.10 | 0.10 | 0.37 | 0.34 | 0.25 |
| | from 25 mg b.i.d. to 50 mg b.i.d (N = 17) | 0.00 | −0.05 | −0.01 | −0.26 | −0.30 | −0.13 | 0.08 | −0.44 | −0.09 |

TABLE VII

[total cholesterol] Median CFB (mmol/L) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| Placebo | Continued (N = 56) | 0.00 | −0.03 | −0.03 | 0.10 | 0.00 | 0.03 | 0.00 | −0.18 | −0.06 |

TABLE VII-continued

[total cholesterol] Median CFB (mmol/L) - 24 weeks results

| Study groups | Dosage | _____ Time points (weeks) _____ | | | | | | | | |
|---|---|---|---|---|---|---|---|---|---|---|
| | | 0 | 1 | 2 | 4 | 8 | 12 | 16 | 20 | 24 |
| | Switched to 100 mg q.d. at week 12 (N = 15) | 0.00 | −0.53 | −0.20 | −0.25 | −0.35 | −0.30 | −0.30 | −0.20 | −0.15 |
| | Switched to 50 mg b.i.d at week 12 (N = 15) | 0.00 | −0.20 | −0.13 | −0.10 | 0.16 | 0.01 | 0.25 | 0.25 | 0.36 |
| Continued q.d. dosage regimen over 24 weeks | 50 mg q.d. (N = 63) | 0.00 | 0.00 | 0.00 | 0.05 | 0.20 | 0.25 | 0.25 | 0.25 | 0.30 |
| | 100 mg q.d. (N = 85) | 0.00 | 0.14 | 0.06 | 0.25 | 0.09 | 0.30 | 0.00 | 0.17 | 0.30 |
| | 200 mg q.d. (N = 86) | 0.00 | 0.25 | 0.34 | 0.33 | 0.54 | 0.36 | 0.34 | 0.47 | 0.37 |
| Continued b.i.d. dosage regimen over 24 weeks | 25 mg b.i.d (N = 69) | 0.00 | 0.15 | 0.10 | 0.10 | 0.05 | 0.24 | 0.10 | 0.25 | 0.19 |
| | 50 mg b.i.d. (N = 85) | 0.00 | 0.21 | 0.17 | 0.28 | 0.22 | 0.23 | 0.22 | 0.37 | 0.26 |
| | 100 mg b.i.d. (N = 84) | 0.00 | 0.28 | 0.31 | 0.45 | 0.55 | 0.80 | 0.53 | 0.50 | 0.42 |
| Increased dosage regimen at 12 weeks | from 50 mg q.d. to 100 mg q.d. (N = 19) | 0.00 | 0.05 | 0.15 | 0.18 | 0.16 | 0.05 | 0.40 | 0.35 | 0.31 |
| | from 25 mg b.i.d. to 50 mg b.i.d (N = 17) | 0.00 | −0.07 | 0.07 | −0.15 | −0.23 | −0.12 | 0.09 | −0.29 | 0.08 |

3.1.1.2.2 Study 2

TABLE VIII

[Total cholesterol] Mean CFB (mmol/L) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −0.103 | 0.058 | 0.191 | 0.279 |
| 2 | −0.124 | −0.021 | 0.214 | 0.375 |
| 4 | −0.074 | 0.113 | 0.369 | 0.418 |
| 8 | −0.067 | 0.252 | 0.335 | 0.460 |
| 12 | −0.010 | 0.184 | 0.517 | 0.581 |

TABLE IX

[Total cholesterol] Median CFB (mmol/L) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −0.110 | 0.100 | 0.100 | 0.260 |
| 2 | −0.055 | 0.000 | 0.140 | 0.330 |
| 4 | −0.135 | 0.000 | 0.265 | 0.390 |
| 8 | −0.080 | 0.250 | 0.250 | 0.400 |
| 12 | −0.130 | 0.140 | 0.350 | 0.560 |

TABLE X

[Total cholesterol] Mean CFB (mmol/L) - 24 weeks results

| Weeks | 0 | 1 | 2 | 4 | 8 | 12 | 16 | 20 | 24 |
|---|---|---|---|---|---|---|---|---|---|
| Placebo switching to 100 mg q.d. (N = 72) | 0.00 | −0.103 | −0.124 | −0.074 | −0.067 | −0.010 | 0.241 | 0.340 | 0.317 |
| 50 mg q.d. responders (N = 57) | 0.00 | 0.003 | −0.071 | 0.047 | 0.257 | 0.165 | 0.267 | 0.089 | 0.117 |
| 50 mg q.d. non responders switching to 100 mg q.d. (N = 15) | 0.00 | 0.264 | 0.165 | 0.359 | 0.237 | 0.253 | 0.454 | 0.395 | 0.532 |
| 100 mg q.d. (N = 70) | 0.00 | 0.191 | 0.214 | 0.369 | 0.335 | 0.517 | 0.505 | 0.439 | 0.529 |
| 200 mg q.d. (N = 69) | 0.00 | 0.279 | 0.375 | 0.418 | 0.460 | 0.581 | 0.517 | 0.504 | 0.581 |

TABLE XI

[Total cholesterol] Median CFB (mmol/L) - 24 weeks results

| Weeks | 0 | 1 | 2 | 4 | 8 | 12 | 16 | 20 | 24 |
|---|---|---|---|---|---|---|---|---|---|
| Placebo switching to 100 mg q.d. (N = 72) | 0.00 | −0.110 | −0.055 | −0.135 | −0.080 | −0.130 | 0.200 | 0.220 | 0.300 |

TABLE XI-continued

[Total cholesterol] Median CFB (mmol/L) - 24 weeks results

| Weeks | 0 | 1 | 2 | 4 | 8 | 12 | 16 | 20 | 24 |
|---|---|---|---|---|---|---|---|---|---|
| 50 mg q.d. responders (N = 57) | 0.00 | 0.020 | −0.040 | −0.030 | 0.350 | 0.060 | 0.165 | 0.215 | 0.250 |
| 50 mg q.d. non responders switching to 100 mg q.d. (N = 15) | 0.00 | 0.150 | 0.100 | 0.350 | 0.140 | 0.330 | 0.540 | 0.280 | 0.550 |
| 100 mg q.d. (N = 70) | 0.00 | 0.100 | 0.140 | 0.265 | 0.250 | 0.350 | 0.400 | 0.400 | 0.445 |
| 200 mg q.d. (N = 69) | 0.00 | 0.260 | 0.330 | 0.390 | 0.400 | 0.560 | 0.410 | 0.490 | 0.565 |

3.1.1.2.3 Study 3

TABLE XII

[Total cholesterol] levels (mmol/L) measured in Study 3 (dosed at 200 mg q.d.)

| Days | Japanese placebo (mmol/L) | Japanese 200 mg q.d. (mmol/L) | Caucasian placebo (mmol/L) | Caucasian 200 mg q.d. (mmol/L) |
|---|---|---|---|---|
| 0 | 4.59 | 4.47 | 4.33 | 4.77 |
| 5 | 4.2 | 4.18 | 4.15 | 4.5 |
| 10 | 4.36 | 4.45 | 4.18 | 4.53 |
| 17 | 4.5 | 4.52 | 4.5 | 4.57 |

3.1.1.2.4 Study 4

TABLE XIII

[Total cholesterol] levels (mmol/L) measured in Study 4

| Time point | placebo | 30 mg q.d. | 75 mg q.d. | 150 mg q.d. | 300 mg q.d. |
|---|---|---|---|---|---|
| Baseline | 4.46 | 5.19 | 4.99 | 4.77 | 4.56 |
| week 1 | 4.65 | 5.31 | 5.04 | 4.94 | 5.13 |
| week 2 | 4.62 | 5.25 | 5.07 | 4.85 | 5.21 |
| week 3 | 4.58 | 5.32 | 5.08 | 4.89 | 5.23 |
| week 4 | 4.61 | 5.50 | 5.18 | 4.96 | 5.33 |

3.1.1.2.5 Study 5

TABLE XIV

[Total cholesterol] Mean CFB (mmol/L) - 10 weeks results

| Weeks | Placebo (N = 44) | 200 mg q.d. (N = 130) |
|---|---|---|
| 0 | — | — |
| 2 | 0.244 | 0.231 |
| 4 | 0.100 | 0.194 |
| 6 | 0.071 | 0.215 |
| 10 | 0.251 | 0.401 |

TABLE XV

[Total cholesterol] Median CFB (mmol/L) - 10 weeks results

| Weeks | Placebo (N = 44) | 200 mg q.d. (N = 130) |
|---|---|---|
| 0 | — | — |
| 2 | 0.210 | 0.200 |
| 4 | 0.075 | 0.180 |
| 6 | 0.000 | 0.300 |
| 10 | 0.210 | 0.340 |

TABLE XVI

[Total cholesterol] Mean CFB (mmol/L) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | 0.28 | 0.14 | 0.25 | 0.48 | 0.39 | 0.29 | 0.28 |
|  | To 100 mg q.d. (N = 22) | — | 0.20 | 0.07 | −0.07 | 0.10 | 0.11 | 0.08 | 0.03 |
| 200 mg q.d. | Continued 200 mg q.d. (N = 77) | — | 0.27 | 0.14 | 0.19 | 0.43 | 0.42 | 0.43 | 0.40 |
|  | To 100 mg q.d. (N = 30) | — | 0.18 | 0.27 | 0.26 | 0.44 | 0.23 | 0.09 | 0.14 |
|  | To placebo (N = 23) | — | 0.16 | 0.27 | 0.22 | 0.22 | 0.04 | 0.19 | 0.18 |

TABLE XVII

[Total cholesterol] Median CFB (mmol/L) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | 0.20 | 0.20 | 0.36 | 0.39 | 0.20 | 0.23 | 0.35 |
|  | To 100 mg q.d. (N = 22) | — | 0.24 | 0.03 | −0.05 | 0.03 | 0.02 | 0.01 | 0.10 |
| 200 mg q.d. | Continued 200 mg q.d. (N = 77) | — | 0.21 | 0.16 | 0.33 | 0.47 | 0.29 | 0.31 | 0.26 |
|  | To 100 mg q.d. (N = 30) | — | 0.19 | 0.12 | 0.28 | 0.38 | 0.33 | 0.13 | 0.10 |
|  | To placebo (N = 23) | — | 0.24 | 0.34 | 0.29 | 0.23 | 0.18 | 0.05 | 0.07 |

3.1.2. LDL Determination

3.1.2.1. Principle of the Assay

LDL determination is available at Quest Diagnostics, Clinical Trials, Quest House, 125-135 Staines Road, Hounslow, Middlesex, TW3 3JB, United Kingdom. Under Catalogue n#83721.

The determination of [LDL]-cholesterol is made using an automated method taking advantage of the selective micellary solubilization of [LDL]-cholesterol by a nonionic detergent and the interaction of a sugar compound and lipoproteins (VLDL and chylomicrons).

When a detergent is included in the enzymatic method for cholesterol determination (cholesterol esterase, cholesterol oxidase coupling reaction), the relative reactivities of cholesterol in the lipoprotein fractions increase in this order: [HDL]<chylomicrons <VLDL <[LDL]. In the presence of $Mg^{2+}$, a sugar compound markedly reduces the enzymatic reaction of the cholesterol measurement in VLDL and chylomicrons. The combination of a sugar compound with detergent enables the selective determination of [LDL]-cholesterol in serum. (Friedewald et al., 1972; Rifai et al., 1992)

Homogeneous enzymatic colorimetric assay.

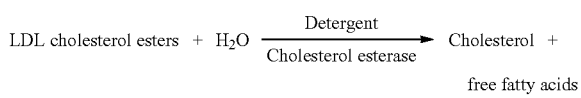

Cholesterol esters are broken down quantitatively into free cholesterol and fatty acids by cholesterol esterase.

In the presence of oxygen, cholesterol is oxidized by cholesterol oxidase to $\Delta^4$-cholestenone and hydrogen peroxide.

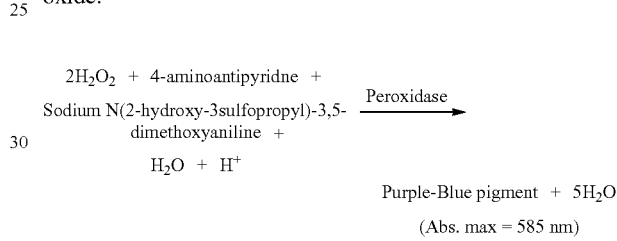

In the presence of peroxidase, the hydrogen peroxide generated reacts with 4-aminoantipyrine and Sodium N-(2-hydroxy-3-sulfopropyl)-3,5-dimethoxyaniline (HSDA) to form a purple-blue dye.

The color intensity of this dye is directly proportional to the cholesterol concentration and is measured photometrically.

3.1.2.2. Assay

Human serum and plasma samples [LDL] determination was done on a Roche/Hitachi Cobas c 701/702 system which automatically calculate the analyte concentration of each sample. Samples containing precipitates are centrifuged before performing the assay.

The machine parameters are listed in Table XVIII below.

TABLE XVIII

| Cobas c 701/702 test parameters for LDL determination | |
|---|---|
| Assay type | 2 Point End |
| Reaction time/Assay points | 10/18-38 |
| Wavelength (sub/main) | 700/600 nm |
| Reaction direction | Increase |
| Units | mmol/L (mg/dL, g/L) |
| Reagent pipetting | Diluent ($H_2O$) |
| MOPS (3-morpholinopropane sulfonic acid) buffer: 20.1 mmol/L, pH 6.5; | 150 μL |
| HSDA: 0.96 mmol/L; | |
| ascorbate oxidase (Eupenicillium spec., recombinant): ≥50 μkat/L; | |
| peroxidase (horseradish): ≥167 μkat/L; preservative | |
| MOPS (3-morpholinopropane sulfonic acid) buffer: 20.1 mmol/L, pH 6.8; | 50 μL |
| $MgSO_4 \cdot 7H_2O$: 8.11 mmol/L; | |
| 4-aminoantipyrine: 2.46 mmol/L; | |

TABLE XVIII-continued

Cobas c 701/702 test parameters for LDL determination cholesterol esterase (Pseudomonas spec.): ≥50 μkat/L; cholesterol oxidase (Brevibacterium spec., recombinant): ≥33.3 μkat/L; peroxidase(horseradish): ≥334 μkat/L; detergent; preservative

| Sample volumes | Sample dilution | Diluent (NaCl) |
|---|---|---|
| Normal (2 μL) | — | — |
| Decreased (10 μL) | 15 μL | 135 μL |
| Increased (4 μL) | — | — |

As disclosed in the respective study protocols for Study 1 or 2, at week 12, depending on the outcome of their treatment, the subjects may be continued in their initial treatment course, or reassigned to another treatment group in a randomized blinded fashion until week 24. Therefore, the number of subjects (N) for the period of either 12 weeks, or 24 weeks is provided to reflect this redistribution at week 12.

Namely, in Study 1, at Week 12, the subjects on placebo who did not achieve at least a 20% improvement in swollen joint count (SJC66) and tender joint count (TJC68) were re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

In Study 2, at Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.

3.1.2.3. Results

3.1.2.3.1 Study 1

TABLE XIX

Figure 4:
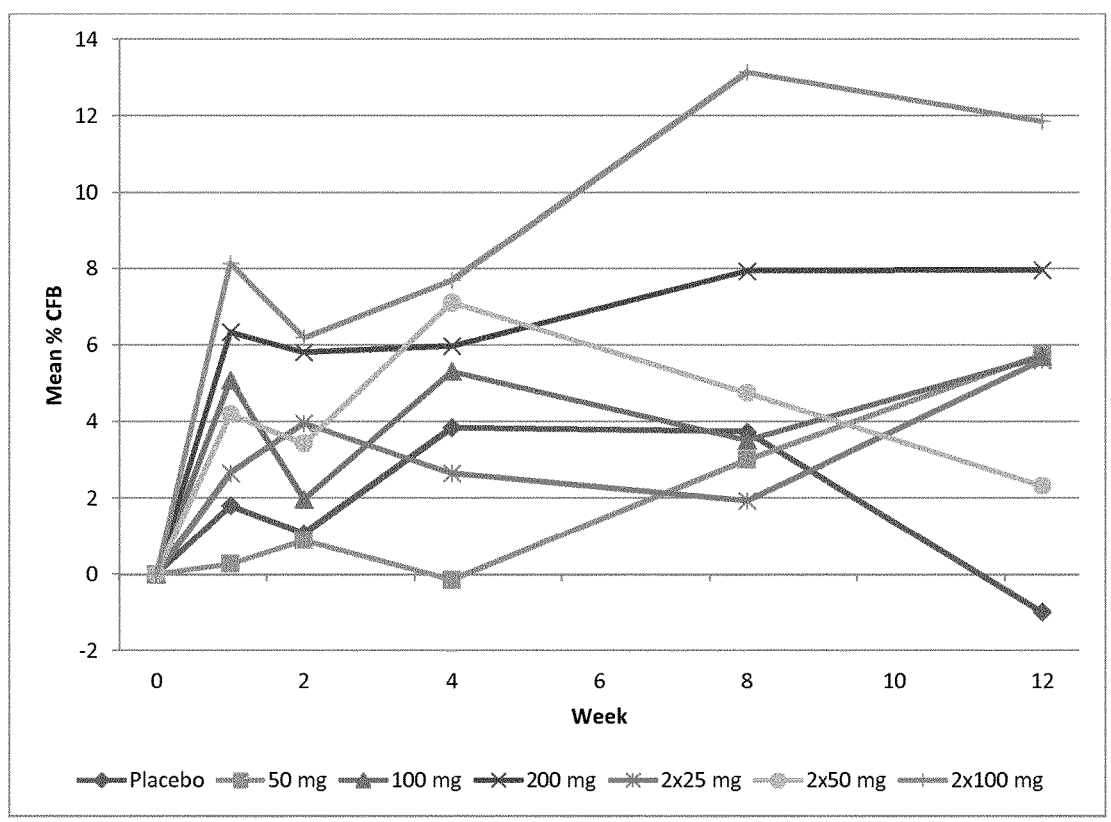
FIG. 4. Shows the mean percentage change vs baseline in [LDL] level in Study 1 in RA patients upon administration of Compound 1 (dosed as [Compound 1:HCl:3H$_2$O] after 12 weeks treatment of varying doses 25 mg b.i.d. (2×25 mg, asterisk), 50 mg b.i.d. (2×50 mg, filled circles), 50 mg q.d. (50 mg, filled squares), 100 mg b.i.d. (2×100 mg, upward crosses), 100 mg q.d. (100 mg, filled triangles), 200 mg q.d. (200 mg, tilted crosses), vs placebo (filled diamonds).
Figure 5:
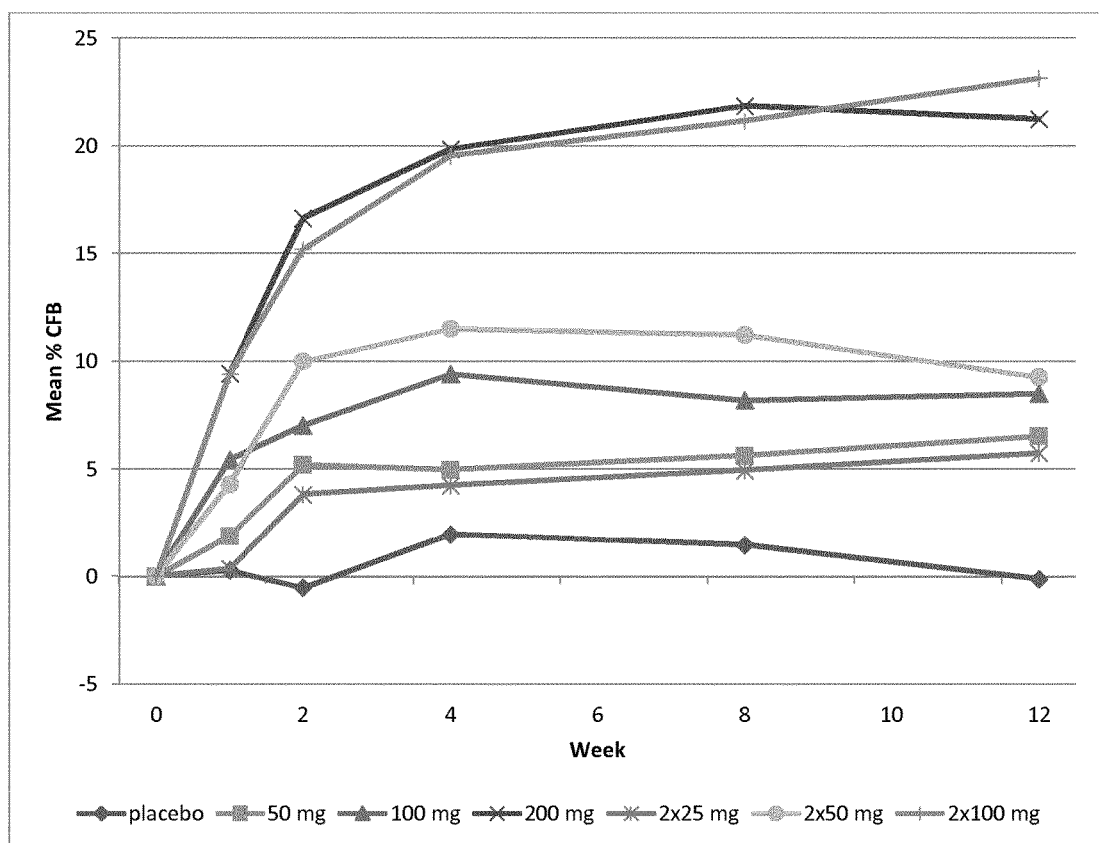
FIG. 5. Shows the mean percentage change vs baseline in [HDL] level in Study 1 in RA patients upon administration of Compound 1 (dosed as [Compound 1:HCl:3H$_2$O] after 12 weeks treatment of varying doses 25 mg b.i.d. (2×25 mg, asterisk), 50 mg b.i.d. (2×50 mg, filled circles), 50 mg q.d. (50 mg, filled squares), 100 mg b.i.d. (2×100 mg, upward crosses), 100 mg q.d. (100 mg, filled triangles), 200 mg q.d. (200 mg, tilted crosses), vs placebo (filled diamonds).

[LDL] Mean CFB (mmol/L) (FIG. 4) - 12 weeks results

| | | q.d. groups | | | b.i.d. groups | | |
|---|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0.00 | 0.00 | 0.00 | 0.00 | 0.00 | 0.00 | 0.00 |
| 1 | 0.01 | −0.01 | 0.11 | 0.16 | 0.04 | 0.10 | 0.20 |
| 2 | −0.03 | 0.02 | 0.01 | 0.11 | 0.04 | 0.04 | 0.15 |
| 4 | 0.06 | 0.01 | 0.13 | 0.13 | −0.01 | 0.14 | 0.17 |
| 8 | 0.04 | 0.06 | 0.03 | 0.16 | −0.05 | 0.07 | 0.31 |
| 12 | −0.06 | 0.14 | 0.13 | 0.19 | 0.07 | 0.05 | 0.27 |

TABLE XX

[LDL] Median CFB (mmol/L) - 12 weeks results

| | | q.d. groups | | | b.i.d. groups | | |
|---|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0.00 | 0.00 | 0.00 | 0.00 | 0.00 | 0.00 | 0.00 |
| 1 | −0.08 | −0.01 | 0.1 | 0.16 | 0.05 | 0.17 | 0.18 |
| 2 | −0.04 | 0.02 | 0.02 | 0.13 | 0.09 | 0.1 | 0.08 |
| 4 | 0.12 | −0.01 | 0.13 | 0.09 | −0.01 | 0.05 | 0.12 |
| 8 | 0.02 | 0.07 | 0.05 | 0.18 | 0.01 | 0.10 | 0.22 |
| 12 | −0.06 | 0.13 | 0.13 | 0.14 | 0.05 | 0.02 | 0.26 |

TABLE XXI

[LDL] Mean CFB (mmol/L) - 24 weeks results

| Study groups | Dosage | Time points (weeks) | | | | | | | |
|---|---|---|---|---|---|---|---|---|---|
| | | 0 | 1 | 2 | 4 | 8 | 12 | 16 | 20 | 24 |
| Placebo | Continued (N = 56) | 0.00 | 0.07 | 0.05 | 0.14 | 0.09 | −0.07 | −0.11 | −0.05 | −0.09 |

TABLE XXI-continued

[LDL] Mean CFB (mmol/L) - 24 weeks results

| Study groups | Dosage | \multicolumn{9}{c}{Time points (weeks)} |
|---|---|---|---|---|---|---|---|---|---|---|

| Study groups | Dosage | 0 | 1 | 2 | 4 | 8 | 12 | 16 | 20 | 24 |
|---|---|---|---|---|---|---|---|---|---|---|
| | Switched to 100 mg q.d. at week 12 (N = 15) | 0.00 | −0.09 | −0.20 | −0.05 | −0.09 | −0.18 | −0.09 | −0.05 | −0.24 |
| | Switched to 50 mg b.i.d at week 12 (N = 15) | 0.00 | −0.14 | −0.17 | −0.09 | −0.01 | 0.09 | 0.07 | 0.13 | −0.01 |
| Continued q.d. dosage regimen over 24 weeks | 50 mg q.d. (N = 63) | 0.00 | 0.00 | −0.02 | 0.02 | 0.08 | 0.16 | 0.15 | 0.14 | 0.13 |
| | 100 mg q.d. (N = 85) | 0.00 | 0.11 | 0.01 | 0.13 | 0.03 | 0.12 | −0.01 | −0.01 | 0.03 |
| | 200 mg q.d. (N = 86) | 0.00 | 0.15 | 0.11 | 0.13 | 0.16 | 0.19 | 0.14 | 0.17 | 0.13 |
| Continued b.i.d. dosage regimen over 12 weeks | 25 mg b.i.d (N = 69) | 0.00 | 0.06 | 0.06 | 0.05 | 0.05 | 0.14 | 0.10 | 0.14 | 0.14 |
| | 50 mg b.i.d. (N = 85) | 0.00 | 0.10 | 0.04 | 0.14 | 0.07 | 0.05 | 0.10 | 0.14 | 0.19 |
| | 100 mg b.i.d. (N = 84) | 0.00 | 0.20 | 0.15 | 0.17 | 0.31 | 0.27 | 0.21 | 0.16 | 0.30 |
| Increased dosage regimen at 12 weeks | from 50 mg q.d. to 100 mg q.d. (N = 19) | 0.00 | −0.02 | 0.15 | −0.03 | 0.02 | 0.06 | 0.12 | 0.10 | 0.14 |
| | from 25 mg b.i.d. to 50 mg b.i.d (N = 17) | 0.00 | −0.07 | −0.05 | −0.25 | −0.42 | −0.17 | −0.13 | −0.48 | −0.25 |

TABLE XXII

[LDL] Median CFB (mmol/L) - 24 weeks results

| Study groups | Dosage | 0 | 1 | 2 | 4 | 8 | 12 | 16 | 20 | 24 |
|---|---|---|---|---|---|---|---|---|---|---|
| Placebo | Continued (N = 56) | 0.00 | −0.05 | 0.03 | 0.18 | 0.02 | 0.03 | −0.06 | −0.11 | −0.06 |
| | Switched to 100 mg q.d. at week 12 (N = 15) | 0.00 | 0.07 | −0.23 | 0.01 | −0.06 | −0.19 | −0.14 | 0.05 | −0.14 |
| | Switched to 50 mg b.i.d at week 12 (N = 15) | 0.00 | −0.12 | −0.09 | −0.06 | 0.15 | 0.03 | 0.16 | 0.06 | 0.22 |
| Continued q.d. dosage regimen over 24 weeks | 50 mg q.d. (N = 63) | 0.00 | −0.01 | 0.02 | −0.01 | 0.13 | 0.14 | 0.12 | 0.20 | 0.14 |
| | 100 mg q.d. N = 85 | 0.00 | 0.10 | 0.02 | 0.13 | 0.04 | 0.13 | 0.03 | 0.02 | 0.03 |
| | 200 mg q.d. (N = 86) | 0.00 | 0.16 | 0.13 | 0.09 | 0.18 | 0.14 | 0.07 | 0.14 | 0.17 |
| Continued b.i.d. dosage regimen over 24 weeks | 25 mg b.i.d (N = 69) | 0.00 | 0.08 | 0.09 | 0.03 | 0.06 | 0.13 | 0.06 | 0.14 | 0.13 |
| | 50 mg b.i.d. (N = 85) | 0.00 | 0.17 | 0.10 | 0.04 | 0.10 | −0.02 | 0.09 | 0.17 | 0.21 |
| | 100 mg b.i.d. (N = 84) | 0.00 | 0.18 | 0.08 | 0.12 | 0.22 | 0.26 | 0.21 | 0.11 | 0.24 |
| Increased dosage regimen at 12 weeks | from 50 mg q.d. to 100 mg q.d. (N = 19) | 0.00 | −0.02 | −0.04 | −0.01 | −0.07 | 0.10 | 0.24 | 0.15 | 0.20 |
| | from 25 mg b.i.d. to 50 mg b.i.d (N = 17) | 0.00 | −0.02 | −0.05 | −0.27 | −0.40 | −0.15 | −0.16 | −0.26 | −0.17 |

3.1.2.3.2 Study 2

TABLE XXIII

| | [LDL] Mean CFB (mmol/L) - 12 weeks results | | | |
|---|---|---|---|---|
| Weeks | Placebo (N = 72) | 50 mg q.d. (N = 72) | 100 mg q.d. (N = 70) | 200 mg q.d. (N = 69) |
| 0 | 0.00 | 0.00 | 0.00 | 0.00 |
| 1 | −0.015 | 0.011 | 0.116 | 0.209 |
| 2 | −0.063 | −0.057 | 0.105 | 0.192 |
| 4 | −0.037 | 0.047 | 0.195 | 0.216 |
| 8 | −0.061 | 0.142 | 0.162 | 0.212 |
| 12 | −0.010 | 0.090 | 0.278 | 0.347 |

TABLE XXIV

| | [LDL] Median CFB (mmol/L) - 12 weeks results | | | |
|---|---|---|---|---|
| Weeks | Placebo (N = 72) | 50 mg q.d. (N = 72) | 100 mg q.d. (N = 70) | 200 mg q.d. (N = 69) |
| 0 | 0.00 | 0.00 | 0.00 | 0.00 |
| 1 | −0.015 | 0.005 | 0.070 | 0.180 |
| 2 | −0.060 | −0.040 | −0.050 | 0.130 |
| 4 | −0.095 | 0.025 | 0.140 | 0.290 |
| 8 | −0.070 | 0.130 | 0.140 | 0.230 |
| 12 | −0.060 | 0.040 | 0.180 | 0.315 |

TABLE XXV

| | [LDL] Mean CFB (mmol/L) - 24 weeks results | | | | | | | | |
|---|---|---|---|---|---|---|---|---|---|
| Weeks | 0 | 1 | 2 | 4 | 8 | 12 | 16 | 20 | 24 |
| Placebo switching to 100 mg q.d. (N = 72) | 0.00 | −0.01 | −0.06 | −0.04 | −0.06 | −0.01 | 0.07 | 0.16 | 0.10 |
| 50 mg q.d. responders (N = 57) | 0.00 | −0.01 | −0.07 | 0.01 | 0.16 | 0.09 | 0.18 | 0.00 | 0.00 |
| 50 mg q.d. non responders switching to 100 mg q.d. (N = 15) | 0.00 | 0.08 | 0.00 | 0.17 | 0.10 | 0.11 | 0.22 | 0.03 | 0.14 |
| 100 mg q.d. (N = 70) | 0.00 | 0.12 | 0.10 | 0.19 | 0.16 | 0.28 | 0.28 | 0.25 | 0.31 |
| 200 mg q.d. (N = 69) | 0.00 | 0.21 | 0.19 | 0.22 | 0.21 | 0.35 | 0.30 | 0.29 | 0.38 |

TABLE XXVI

| | [LDL] Median CFB (mmol/L) - 24 weeks results | | | | | | | | |
|---|---|---|---|---|---|---|---|---|---|
| Weeks | 0 | 1 | 2 | 4 | 8 | 12 | 16 | 20 | 24 |
| Placebo switching to 100 mg q.d. (N = 72) | 0.00 | −0.01 | −0.06 | −0.10 | −0.07 | −0.06 | −0.05 | 0.03 | 0.12 |
| 50 mg q.d. responders (N = 57) | 0.00 | −0.01 | −0.06 | −0.05 | 0.14 | 0.03 | 0.16 | 0.12 | −0.01 |
| 50 mg q.d. non responders switching to 100 mg q.d. (N = 15) | 0.00 | 0.07 | −0.02 | 0.05 | 0.10 | 0.09 | 0.20 | −0.04 | 0.15 |
| 100 mg q.d. (N = 70) | 0.00 | 0.07 | −0.05 | 0.14 | 0.14 | 0.18 | 0.20 | 0.23 | 0.31 |
| 200 mg q.d. (N = 69) | 0.00 | 0.18 | 0.13 | 0.29 | 0.23 | 0.32 | 0.23 | 0.25 | 0.34 |

3.1.2.3.3 Study 3

TABLE XXVII

[LDL] levels (mmol/L) measured in Study 3 (dosed at 200 mg q.d.)

| Days | Japanese placebo (mmol/L) | Japanese 200 mg q.d. (mmol/L) | Caucasian placebo (mmol/L) | Caucasian 200 mg q.d. (mmol/L) |
|---|---|---|---|---|
| 0 | 2.6 | 2.7 | 2.4 | 2.6 |
| 5 | 2.5 | 2.5 | 2.5 | 2.6 |
| 10 | 2.6 | 2.5 | 2.4 | 2.4 |
| 17 | 2.7 | 2.7 | 2.7 | 2.5 |

3.1.2.3.4 Study 4

TABLE XXVIII

[LDL] levels (mmol/L) measured in Study 4

| Time point | placebo | 30 mg q.d. | 75 mg q.d. | 150 mg q.d. | 300 mg q.d. |
|---|---|---|---|---|---|
| Baseline | 2.70 | 3.34 | 3.22 | 3.01 | 2.82 |
| week 1 | 2.75 | 3.40 | 3.25 | 3.18 | 3.19 |
| week 2 | 2.77 | 3.35 | 3.17 | 2.95 | 3.11 |
| week 3 | 2.75 | 3.41 | 3.14 | 2.96 | 3.18 |
| week 4 | 2.79 | 3.60 | 3.36 | 3.06 | 3.18 |

3.1.2.3.5 Study 5

TABLE XXIX

[LDL] Mean CFB (mmol/L) - 10 weeks results

| Weeks | Placebo (N = 44) | 200 mg q.d. (N = 130) |
|---|---|---|
| 0 | — | — |
| 2 | 0.215 | 0.025 |
| 4 | 0.074 | −0.030 |
| 6 | 0.075 | −0.012 |
| 10 | 0.227 | 0.150 |

TABLE XXX

[LDL] Median CFB (mmol/L) - 10 weeks results

| Weeks | Placebo (N = 44) | 200 mg q.d. (N = 130) |
|---|---|---|
| 0 | — | — |
| 2 | 0.195 | −0.050 |
| 4 | −0.020 | −0.050 |
| 6 | 0.050 | 0.025 |
| 10 | 0.230 | 0.160 |

TABLE XXXI

[LDL] Mean CFB (mmol/L) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | 0.22 | 0.10 | 0.20 | 0.31 | 0.34 | 0.22 | 0.30 |
|  | To 100 mg q.d. (N = 22) | — | 0.21 | 0.05 | −0.02 | 0.18 | 0.09 | 0.05 | 0.06 |
| 200 mg q.d. | Continued 200 mg q.d. (N = 77) | — | 0.04 | −0.05 | −0.05 | 0.20 | 0.14 | 0.21 | 0.22 |
|  | To 100 mg q.d. (N = 30) | — | −0.02 | 0.00 | 0.00 | 0.10 | 0.10 | 0.01 | 0.01 |
|  | To placebo (N = 23) | — | 0.037 | −0.017 | 0.085 | 0.077 | 0.105 | 0.222 | 0.205 |

TABLE XXXII

[LDL] Median CFB (mmol/L) - 10 weeks results 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | 0.10 | −0.02 | 0.16 | 0.28 | 0.29 | 0.17 | 0.30 |
|  | To 100 mg q.d. (N = 22) | — | 0.23 | −0.02 | −0.11 | 0.22 | 0.07 | −0.06 | 0.03 |
| 200 mg q.d. | Continued 200 mg q.d. (N = 77) | — | −0.05 | −0.05 | −0.02 | 0.18 | 0.15 | 0.19 | 0.18 |
|  | To 100 mg q.d. (N = 30) | — | −0.05 | −0.10 | 0.04 | 0.17 | 0.19 | −0.05 | 0.04 |
|  | To placebo (N = 23) | — | 0.02 | 0.05 | 0.09 | 0.03 | 0.12 | 0.08 | 0.11 |

3.1.3. [HDL] Determination

3.1.3.1. Assay Principle

[HDL] determination is available at Quest Diagnostics, Clinical Trials, Quest House, 125-135 Staines Road, Hounslow, Middlesex, TW3 3JB, United Kingdom. Under Catalogue n#83718.

This assay relies on a homogeneous enzymatic colorimetric test. In the presence of magnesium ions, dextran sulfate selectively forms water-soluble complexes with LDL, VLDL and chylomicrons which are resistant to PEG-modified enzymes.

The cholesterol concentration of [HDL]-cholesterol is determined enzymatically by cholesterol esterase and cholesterol oxidase coupled with PEG to the amino groups (approx. 40%).

Cholesterol esters are broken down quantitatively into free cholesterol and fatty acids by cholesterol esterase.

hydroxy-3-sulfopropyl)-3,5-dimethoxyaniline (HSDA) to form a purple-blue dye. The color intensity of this dye is directly proportional to the cholesterol concentration and is measured photometrically.

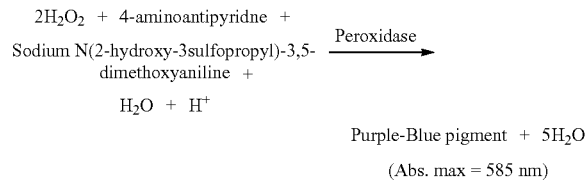

(Abs. max = 585 nm)

3.1.3.2. Assay

Human serum and plasma samples [HDL] determination was done on a Roche/Hitachi Cobas c 701/702 system which automatically calculate the analyte concentration of each sample. Samples containing precipitates are centrifuged before performing the assay.

The machine parameters are listed in Table XXXIII below.

TABLE XXXIII

| Cobas c 701/702 test parameters for [HDL] determination | |
|---|---|
| Assay type | 2 Point End |
| Reaction time/Assay points | 10/18-38 |
| Wavelength (sub/main) | 700/600 nm |
| Reaction direction | Increase |
| Units | mmol/L (mg/dL, g/L) |
| Reagent pipetting | Diluent ($H_2O$) |
| HEPES buffer: 10.07 mmol/L; CHES 96.95 mmol/L, pH 7.4; Dextran sulfate: 1.5 g/L; magnesium nitrate hexahydrate: >11.7 mmol/L; HSDA: 0.96 mmol/L; ascorbate oxidase (Eupenicillium sp., recombinant): >50 μkat/L; peroxidase (horseradish): >16.7 μkat/L; preservative | 150 μL |
| HEPES buffer: 10.07 mmol/L, pH 7.0; PEG-cholesterol esterase (Pseudonomas spec.): >3.33 μkat/L; PEG-cholesterol oxidase (Streptomyces sp., recombinant): >127 μkat/L; peroxidase (horseradish): >333 μkat/L; 4-amino-antipyrine: 2.46 mmol/L; preservative | 50 μL |

| Sample volumes | Sample dilution | Diluent (NaCl) |
|---|---|---|
| Normal (2.5 μL) | — | — |
| Decreased (12.5 μL) | 15 μL | 135 μL |
| Increased (5.0 μL) | — | — |

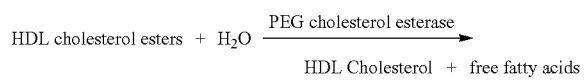

In the presence of oxygen, cholesterol is oxidized by cholesterol oxidase to $\Delta^4$-cholestenone and hydrogen peroxide.

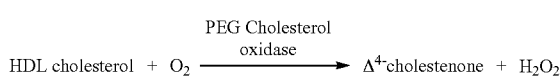

In the presence of peroxidase, the hydrogen peroxide generated reacts with 4-amino-antipyrine and Sodium N-(2-

As disclosed in the respective study protocols for Study 1 or 2, at week 12, depending on the outcome of their treatment, the subjects may be continued in their initial treatment course, or reassigned to another treatment group in a randomized blinded fashion until week 24. Therefore, the number of subjects (N) for the period of either 12 weeks, or 24 weeks is provided to reflect this redistribution at week 12. Namely, in Study 1, at Week 12, the subjects on placebo who did not achieve at least a 20% improvement in swollen joint count (SJC66) and tender joint count (TJC68) were re-randomized automatically to receive Compound 1 (dosed as a [Compound 1:HCl:3$H_2O$]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

In Study 2, at Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.

3.1.3.3. Results

3.1.3.3.1 Study 1

TABLE XXXIV

[HDL] Mean CFB (mmol/L) - 12 weeks results

| | | q.d. groups | | | b.i.d. groups | | |
|---|---|---|---|---|---|---|---|
| Weeks | Placebo (N = 86) | 50 mg (N = 82) | 100 mg (N = 85) | 200 mg (N = 86) | 2 x 25 mg (N = 86) | 2 x 50 mg (N = 85) | 2 x 100 mg (N = 84) |
| 0 | 0.00 | 0.00 | 0.00 | 0.00 | 0.00 | 0.00 | 0.00 |
| 1 | −0.02 | 0.02 | 0.05 | 0.11 | 0.00 | 0.03 | 0.12 |
| 2 | −0.03 | 0.08 | 0.07 | 0.20 | 0.04 | 0.12 | 0.20 |
| 4 | 0.01 | 0.06 | 0.11 | 0.24 | 0.05 | 0.13 | 0.25 |
| 8 | 0.00 | 0.06 | 0.09 | 0.29 | 0.06 | 0.13 | 0.26 |
| 12 | −0.03 | 0.06 | 0.10 | 0.27 | 0.06 | 0.10 | 0.30 |

TABLE XXXV

[HDL] Median CFB (mmol/L) - 12 weeks results

| | | q.d. groups | | | b.i.d. groups | | |
|---|---|---|---|---|---|---|---|
| Weeks | Placebo (N = 86) | 50 mg (N = 82) | 100 mg (N = 85) | 200 mg (N = 86) | 2 x 25 mg (N = 86) | 2 x 50 mg (N = 85) | 2 x 100 mg (N = 84) |
| 0 | 0.00 | 0.00 | 0.00 | 0.00 | 0.00 | 0.00 | 0.00 |
| 1 | 0.00 | 0.01 | 0.06 | 0.13 | 0.00 | 0.05 | 0.10 |
| 2 | 0.00 | 0.08 | 0.07 | 0.20 | 0.05 | 0.10 | 0.18 |
| 4 | 0.00 | 0.05 | 0.13 | 0.25 | 0.05 | 0.13 | 0.25 |
| 8 | 0.00 | 0.10 | 0.11 | 0.30 | 0.10 | 0.14 | 0.25 |
| 12 | −0.03 | 0.05 | 0.10 | 0.26 | 0.05 | 0.10 | 0.25 |

TABLE XXXVI

[HDL] Mean CFB (mmol/L) - 24 weeks results

| Study groups | Dosage | 0 | 1 | 2 | 4 | 8 | 12 | 16 | 20 | 24 |
|---|---|---|---|---|---|---|---|---|---|---|
| Placebo | Continued (N = 56) | 0.00 | 0.02 | 0.00 | 0.04 | 0.01 | 0.01 | 0.01 | −0.01 | 0.03 |
| | Switched to 100 mg q.d. at week 12 (N = 15) | 0.00 | −0.12 | −0.14 | −0.12 | −0.14 | −0.15 | −0.06 | −0.04 | −0.03 |
| | Switched to 50 mg b.i.d at week 12 (N = 15) | 0.00 | −0.07 | −0.03 | 0.02 | 0.11 | −0.02 | 0.08 | 0.10 | 0.10 |
| Continued q.d. dosage regimen over 24 weeks | 50 mg q.d. (N = 63) | 0.00 | 0.02 | 0.07 | 0.06 | 0.06 | 0.08 | 0.08 | 0.10 | 0.17 |
| | 100 mg q.d. (N = 85) | 0.00 | 0.05 | 0.07 | 0.11 | 0.09 | 0.10 | 0.09 | 0.15 | 0.15 |
| | 200 mg q.d. (N = 86) | 0.00 | 0.11 | 0.20 | 0.24 | 0.29 | 0.27 | 0.27 | 0.30 | 0.26 |
| Continued b.i.d. dosage regimen over 24 weeks | 25 mg b.i.d (N = 69) | 0.00 | 0.01 | 0.05 | 0.07 | 0.08 | 0.07 | 0.08 | 0.05 | 0.08 |
| | 50 mg b.i.d. (N = 85) | 0.00 | 0.03 | 0.12 | 0.13 | 0.13 | 0.10 | 0.13 | 0.15 | 0.11 |
| | 100 mg b.i.d. (N = 84) | 0.00 | 0.12 | 0.20 | 0.25 | 0.26 | 0.30 | 0.27 | 0.28 | 0.29 |
| Increased dosage regimen at 12 weeks | from 50 mg q.d. to 100 mg q.d. (N = 19) | 0.00 | 0.02 | 0.10 | 0.07 | 0.05 | −0.02 | 0.18 | 0.13 | 0.11 |
| | from 25 mg b.i.d. to 50 mg b.i.d (N = 17) | 0.00 | −0.05 | 0.03 | −0.01 | −0.02 | 0.04 | 0.05 | −0.02 | 0.10 |

TABLE XXXVII

[HDL] Median CFB (mmol/L) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| Placebo | Continued (N = 56) | 0.00 | 0.03 | 0.04 | 0.01 | 0.00 | 0.01 | 0.00 | 0.00 | 0.00 |
| | Switched to 100 mg q.d. at week 12 (N = 15) | 0.00 | −0.10 | −0.10 | −0.10 | −0.06 | −0.10 | 0.00 | −0.09 | −0.08 |
| | Switched to 50 mg b.i.d at week 12 (N = 15) | 0.00 | −0.03 | 0.00 | −0.05 | 0.11 | −0.05 | 0.18 | 0.21 | 0.10 |
| Continued q.d. dosage regimen over 24 weeks | 50 mg q.d. (N = 63) | 0.00 | 0.01 | 0.08 | 0.05 | 0.10 | 0.06 | 0.10 | 0.10 | 0.15 |
| | 100 mg q.d. (N = 85) | 0.00 | 0.06 | 0.07 | 0.13 | 0.11 | 0.10 | 0.10 | 0.14 | 0.15 |
| | 200 mg q.d. (N = 86) | 0.00 | 0.13 | 0.20 | 0.25 | 0.30 | 0.26 | 0.23 | 0.30 | 0.25 |
| Continued b.i.d. dosage regimen over 24 weeks | 25 mg b.i.d (N = 69) | 0.00 | 0.00 | 0.05 | 0.08 | 0.10 | 0.05 | 0.05 | 0.07 | 0.09 |
| | 50 mg b.i.d. (N = 85) | 0.00 | 0.05 | 0.10 | 0.13 | 0.14 | 0.10 | 0.15 | 0.16 | 0.12 |
| | 100 mg b.i.d. (N = 84) | 0.00 | 0.10 | 0.18 | 0.25 | 0.25 | 0.25 | 0.28 | 0.29 | 0.30 |
| Increased dosage regimen at 12 weeks | from 50 mg q.d. to 100 mg q.d. (N = 19) | 0.00 | 0.00 | 0.07 | 0.06 | 0.09 | −0.05 | 0.15 | 0.20 | 0.11 |
| | from 25 mg b.i.d. to 50 mg b.i.d (N = 17) | 0.00 | −0.01 | 0.05 | 0.00 | 0.05 | 0.00 | 0.15 | −0.02 | 0.17 |

3.1.3.3.2 Study 2

TABLE XXXVIII

[HDL] Mean CFB (mmol/L)

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −0.033 | 0.033 | 0.085 | 0.026 |
| 2 | −0.022 | 0.055 | 0.131 | 0.163 |
| 4 | 0.002 | 0.102 | 0.194 | 0.220 |
| 8 | 0.041 | 0.120 | 0.171 | 0.219 |
| 12 | 0.028 | 0.078 | 0.190 | 0.194 |

TABLE XXXIX

[HDL] Median CFB (mmol/L)

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −0.035 | 0.050 | 0.050 | 0.030 |
| 2 | −0.005 | 0.000 | 0.100 | 0.150 |
| 4 | 0.000 | 0.100 | 0.175 | 0.210 |
| 8 | 0.000 | 0.110 | 0.140 | 0.200 |
| 12 | 0.035 | 0.065 | 0.150 | 0.150 |

TABLE XL

[HDL] Mean CFB (mmol/L) - 24 weeks results

| Weeks | 0 | 1 | 2 | 4 | 8 | 12 | 16 | 20 | 24 |
|---|---|---|---|---|---|---|---|---|---|
| Placebo switching to 100 mg q.d. (N = 72) | 0.00 | −0.03 | −0.02 | 0.00 | 0.04 | 0.03 | 0.19 | 0.19 | 0.16 |
| 50 mg q.d. responders (N = 57) | 0.00 | 0.02 | 0.05 | 0.09 | 0.13 | 0.06 | 0.08 | 0.11 | 0.17 |
| 50 mg q.d. non responders switching to 100 mg q.d. (N = 15) | 0.00 | 0.08 | 0.05 | 0.14 | 0.09 | 0.15 | 0.20 | 0.21 | 0.30 |
| 100 mg q.d. (N = 70) | 0.00 | 0.09 | 0.13 | 0.19 | 0.17 | 0.19 | 0.23 | 0.19 | 0.18 |
| 200 mg q.d. (N = 69) | 0.00 | 0.03 | 0.16 | 0.22 | 0.22 | 0.19 | 0.19 | 0.21 | 0.19 |

TABLE XLI

[HDL] Median CFB (mmol/L) - 24 weeks results

| Weeks | 0 | 1 | 2 | 4 | 8 | 12 | 16 | 20 | 24 |
|---|---|---|---|---|---|---|---|---|---|
| Placebo switching to 100 mg q.d. (N = 72) | 0.00 | −0.03 | −0.01 | 0.00 | 0.00 | 0.03 | 0.16 | 0.18 | 0.15 |
| 50 mg q.d. responders (N = 57) | 0.00 | 0.04 | 0.00 | 0.10 | 0.14 | 0.05 | 0.03 | 0.08 | 0.10 |
| 50 mg q.d. non responders switching to 100 mg q.d. (N = 15) | 0.00 | 0.05 | 0.04 | 0.11 | 0.10 | 0.14 | 0.21 | 0.25 | 0.31 |
| 100 mg q.d. (N = 70) | 0.00 | 0.05 | 0.10 | 0.18 | 0.14 | 0.15 | 0.20 | 0.17 | 0.18 |
| 200 mg q.d. (N = 69) | 0.00 | 0.03 | 0.15 | 0.21 | 0.20 | 0.15 | 0.16 | 0.16 | 0.16 |

3.1.3.3.3 Study 3

TABLE XLII

[HDL] levels (mmol/L) measured in Study 3 (dosed at 200 mg q.d.)

| Days | Japanese placebo (mmol/L) | Japanese 200 mg q.d. (mmol/L) | Caucasian placebo (mmol/L) | Caucasian 200 mg q.d. (mmol/L) |
|---|---|---|---|---|
| 0 | 1.5 | 1.3 | 1.4 | 1.5 |
| 5 | 1.3 | 1.3 | 1.4 | 1.5 |
| 10 | 1.4 | 1.5 | 1.3 | 1.6 |
| 17 | 1.4 | 1.4 | 1.3 | 1.6 |

3.1.3.3.4 Study 4

TABLE XLIII

[HDL] levels (mmol/L) measured in Study 4

| Time point | placebo | 30 mg q.d. | 75 mg q.d. | 150 mg q.d. | 300 mg q.d. |
|---|---|---|---|---|---|
| Baseline | 1.41 | 1.40 | 1.46 | 1.46 | 1.36 |
| week 1 | 1.38 | 1.44 | 1.46 | 1.45 | 1.55 |
| week 2 | 1.43 | 1.43 | 1.50 | 1.47 | 1.73 |
| week 3 | 1.41 | 1.38 | 1.56 | 1.55 | 1.75 |
| week 4 | 1.42 | 1.43 | 1.57 | 1.53 | 1.84 |

3.1.3.3.5 Study 5

TABLE XLIV

[HDL] Mean CFB (mmol/L) - 10 weeks results

| Weeks | Placebo (N = 44) | 200 mg q.d. (N = 130) |
|---|---|---|
| 0 | — | — |
| 2 | 0.064 | 0.222 |
| 4 | 0.050 | 0.237 |
| 6 | 0.038 | 0.243 |
| 10 | 0.014 | 0.239 |

TABLE XLV

[HDL] Median CFB (mmol/L) - 10 weeks results

| Weeks | Placebo (N = 44) | 200 mg q.d. (N = 130) |
|---|---|---|
| 0 | — | — |
| 2 | 0.060 | 0.210 |
| 4 | 0.040 | 0.210 |
| 6 | 0.030 | 0.250 |
| 10 | 0.030 | 0.260 |

TABLE XLVI

[HDL] Mean CFB (mmol/L) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | 0.0 | 0.11 | 0.06 | 0.13 | 0.14 | 0.13 | 0.10 | 0.05 |
|  | To 100 mg q.d. (N = 22) | 0.0 | 0.02 | 0.04 | −0.03 | −0.07 | 0.03 | 0.09 | 0.00 |
| 200 mg q.d. | Continued 200 mg q.d. (N = 77) | 0.0 | 0.23 | 0.18 | 0.24 | 0.22 | 0.20 | 0.17 | 0.10 |
|  | To 100 mg q.d. (N = 30) | 0.0 | 0.24 | 0.31 | 0.33 | 0.33 | 0.17 | 0.11 | 0.18 |
|  | To placebo (N = 23) | 0.0 | 0.18 | 0.30 | 0.15 | 0.16 | −0.12 | −0.18 | −0.21 |

TABLE XLVII

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | 0.0 | 0.12 | 0.04 | 0.16 | 0.18 | 0.08 | 0.08 | 0.07 |
|  | To 100 mg q.d. (N = 22) | 0.0 | −0.02 | 0.06 | 0.01 | −0.03 | 0.12 | 0.12 | 0.10 |
| 200 mg q.d. | Continued 200 mg q.d. (N = 77) | 0.0 | 0.21 | 0.16 | 0.21 | 0.25 | 0.15 | 0.20 | 0.15 |
|  | To 100 mg q.d. (N = 30) | 0.0 | 0.22 | 0.22 | 0.31 | 0.26 | 0.15 | 0.03 | 0.16 |
|  | To placebo (N = 23) | 0.0 | 0.18 | 0.39 | 0.16 | 0.24 | −0.03 | −0.05 | −0.08 |

3.1.4. [Total Cholesterol]-[HDL]-[LDL] Percentage Change Vs Baseline

Further to the determination of the absolute values of [Total cholesterol], [HDL], and [LDL], the percentage changes are calculated.

3.1.4.1. Study 1

Figure 3:
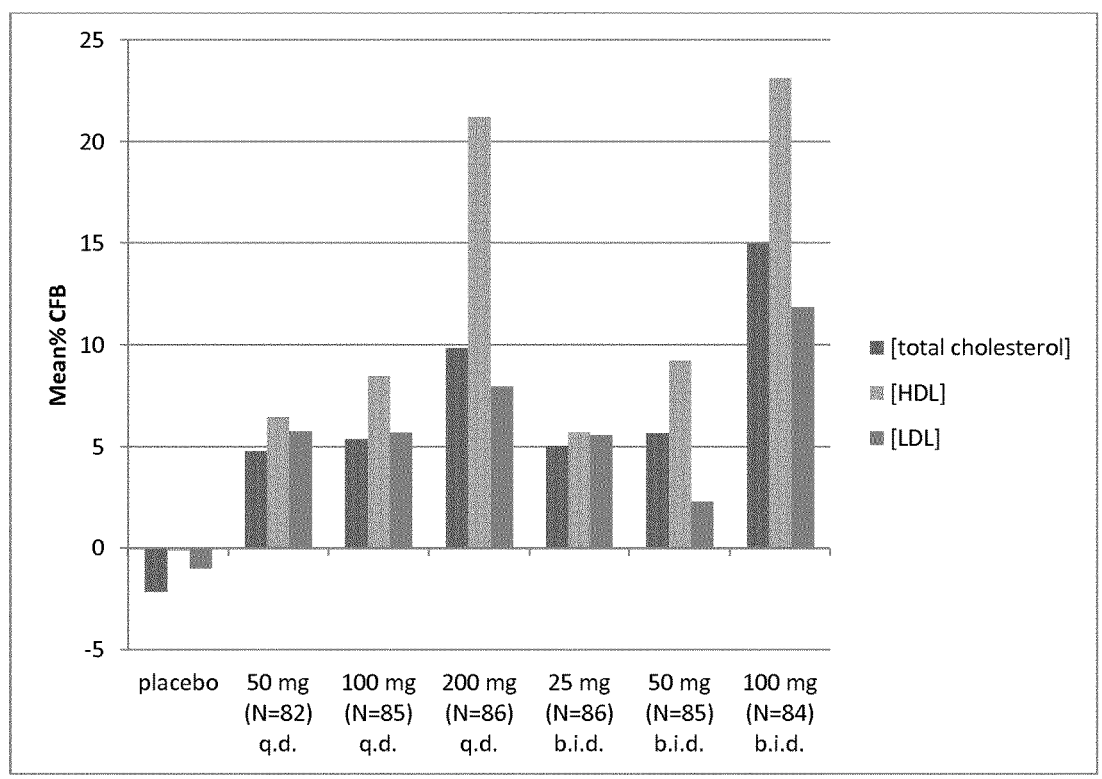
FIG. 3. Shows the mean percentage change in [Total Cholesterol], [HDL] and [LDL] vs baseline in Study 1 in RA patients upon administration of Compound 1 (dosed as [Compound 1:HCl:3H$_2$O] after 12 weeks treatment of varying doses 25 mg b.i.d., 50 mg b.i.d., 50 mg q.d. 100 mg b.i.d., 100 mg q.d., 200 mg q.d. vs placebo.

The mean percentage changes CFB with Compound 1 dosed as the [Compound 1:HCl:3H$_2$O] are reported in below. The mean percentage changes CFB after 12 weeks are presented on FIG. 3.

As disclosed in the respective study protocols for Study 1 or 2, at week 12, depending on the outcome of their treatment, the subjects may be continued in their initial treatment course, or reassigned to another treatment group in a randomized blinded fashion until week 24. Therefore, the number of subjects (N) for the period of either 12 weeks, or 24 weeks is provided to reflect this redistribution at week 12.

Namely, in Study 1, at Week 12, the subjects on placebo who did not achieve at least a 20% improvement in swollen joint count (SJC66) and tender joint count (TJC68) were re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

In Study 2, at Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.

TABLE XLVIII

[total cholesterol] Mean percentage CFB (%) (FIG. 3) -12 weeks results

| | q.d. groups | | | | b.i.d. groups | | |
|---|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0 | 0 | 0 | 0 | 0 | 0 | 0 |
| 1 | −1 | 1 | 4 | 6 | 2 | 3 | 7 |
| 2 | −2 | 1 | 2 | 7 | 3 | 4 | 8 |
| 4 | 1 | 1 | 5 | 8 | 3 | 7 | 10 |
| 8 | 0 | 3 | 4 | 10 | 3 | 6 | 15 |
| 12 | −2 | 5 | 5 | 10 | 5 | 6 | 15 |

TABLE XLIX

[HDL] Mean percentage CFB (%) (FIG. 3) -12 weeks results

| | q.d. groups | | | | b.i.d. groups | | |
|---|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0 | 0 | 0 | 0 | 0 | 0 | 0 |
| 1 | 0 | 2 | 5 | 9 | 0 | 4 | 9 |
| 2 | −1 | 5 | 7 | 17 | 4 | 10 | 15 |
| 4 | 2 | 5 | 9 | 20 | 4 | 12 | 20 |
| 8 | 1 | 6 | 8 | 22 | 5 | 11 | 21 |
| 12 | 0 | 7 | 8 | 21 | 6 | 9 | 23 |

TABLE L

[LDL] Mean percentage CFB (%) (FIG. 3) -12 weeks results

| | | q.d. groups | | | b.i.d. groups | | |
|---|---|---|---|---|---|---|---|
| Weeks | Placebo (N = 86) | 50 mg (N = 82) | 100 mg (N = 85) | 200 mg (N = 86) | 2 x 25 mg (N = 86) | 2 x 50 mg (N = 85) | 2 x 100 mg (N = 84) |
| 0 | 0 | 0 | 0 | 0 | 0 | 0 | 0 |
| 1 | 2 | 0 | 5 | 6 | 3 | 4 | 8 |
| 2 | 1 | 1 | 2 | 6 | 4 | 3 | 6 |
| 4 | 4 | 0 | 5 | 6 | 3 | 7 | 8 |
| 8 | 4 | 3 | 4 | 8 | 2 | 5 | 13 |
| 12 | −1 | 6 | 6 | 8 | 6 | 2 | 12 |

TABLE LI

[total cholesterol] Mean percentage CFB (%) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| Placebo | Continued N = 56 | 0.00 | 1.02 | 0.95 | 3.61 | 2.15 | −0.98 | −2.33 | −1.28 | −2.13 |
| | Switched to 100 mg q.d. at week 12 N = 15 | 0.00 | −6.62 | −7.69 | −5.06 | −6.18 | −8.96 | −3.17 | −3.11 | −4.73 |
| | Switched to 50 mg b.i.d at week 12 N = 15 | 0.00 | −4.60 | −5.05 | −2.87 | 0.76 | 0.46 | 3.97 | 5.80 | 3.22 |
| Continued q.d. dosage regimen over 24 weeks | 50 mg q.d. N = 63 | 0.00 | 0.77 | −0.22 | 1.08 | 3.49 | 5.58 | 5.15 | 4.68 | 6.75 |
| | 100 mg q.d. N = 85 | 0.00 | 3.65 | 2.32 | 4.86 | 3.79 | 5.39 | 1.87 | 3.28 | 5.05 |
| | 200 mg q.d. N = 86 | 0.00 | 5.53 | 9.86 | 8.99 | 6.72 | 10.16 | 9.19 | 8.00 | 9.94 |
| Continued b.i.d. dosage regimen over 24 weeks | 25 mg b.i.d N = 69 | 0.00 | 2.56 | 3.22 | 4.05 | 4.25 | 6.38 | 5.51 | 6.95 | 6.53 |
| | 50 mg b.i.d. N = 85 | 0.00 | 3.39 | 3.87 | 7.04 | 5.63 | 5.67 | 6.23 | 7.91 | 7.97 |
| | 100 mg b.i.d. N = 84 | 0.00 | 6.85 | 8.38 | 9.86 | 14.79 | 14.98 | 12.82 | 12.71 | 15.39 |
| Increased dosage regimen at 12 weeks | from 50 mg q.d. to 100 mg q.d. N = 19 | 0.00 | 1.24 | 4.36 | 1.67 | 2.29 | 2.39 | 7.55 | 6.69 | 5.15 |
| | from 25 mg b.i.d. to 50 mg b.i.d N = 17 | 0.00 | 0.55 | 2.37 | −2.60 | −2.81 | 0.30 | 4.23 | −5.02 | 2.66 |

TABLE LII

[HDL] Mean percentage CFB (%) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| Placebo | Continued N = 56 | 0.00 | 2.53 | 0.69 | 3.60 | 1.62 | 2.30 | 2.28 | 0.38 | 2.45 |
| | Switched to 100 mg q.d. at week 12 N = 15 | 0.00 | −6.43 | −8.33 | −8.23 | −8.63 | −9.85 | −0.14 | 0.95 | 0.14 |
| | Switched to 50 mg b.i.d at week 12 N = 15 | 0.00 | −1.38 | 2.81 | 6.10 | 10.98 | 1.08 | 10.96 | 12.63 | 10.63 |
| Continued q.d. dosage regimen over 24 weeks | 50 mg q.d. N = 63 | 0.00 | 1.75 | 4.74 | 4.87 | 5.57 | 7.86 | 6.63 | 8.81 | 14.22 |
| | 100 mg q.d. N = 85 | 0.00 | 5.43 | 7.02 | 9.40 | 8.18 | 8.49 | 7.94 | 12.24 | 12.17 |
| | 200 mg q.d. N = 86 | 0.00 | 9.42 | 16.66 | 19.85 | 21.85 | 21.24 | 21.14 | 24.27 | 20.78 |
| Continued b.i.d. | 25 mg b.i.d N = 69 | 0.00 | 0.74 | 3.77 | 5.04 | 6.08 | 5.78 | 6.74 | 5.08 | 6.59 |

TABLE LII-continued

[HDL] Mean percentage CFB (%) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| dosage regimen over 24 weeks | 50 mg b.i.d. N = 85 | 0.00 | 4.29 | 9.99 | 11.50 | 11.21 | 9.27 | 11.13 | 12.24 | 10.05 |
| | 100 mg b.i.d. N = 84 | 0.00 | 9.40 | 15.20 | 19.54 | 21.15 | 23.14 | 21.09 | 21.88 | 22.68 |
| Increased dosage regimen at 12 weeks | from 50 mg q.d. to 100 mg q.d. N = 19 | 0.00 | 2.29 | 6.63 | 5.26 | 5.77 | 2.41 | 11.43 | 8.89 | 8.29 |
| | from 25 mg b.i.d. to 50 mg b.i.d N = 17 | 0.00 | −1.35 | 4.08 | 1.09 | 0.59 | 5.55 | 7.37 | 1.50 | 8.10 |

TABLE LIII

[LDL] Mean percentage CFB (%) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| Placebo | Continued N = 56 | 0.00 | 4.77 | 5.00 | 7.39 | 5.90 | −0.72 | −1.26 | 0.20 | −1.79 |
| | Switched to 100 mg q.d. at week 12 N = 15 | 0.00 | −3.28 | −6.69 | −1.44 | −2.00 | −5.97 | −2.85 | −1.07 | −8.19 |
| | Switched to 50 mg b.i.d at week 12 N = 15 | 0.00 | −4.22 | −5.61 | −3.90 | 1.62 | 3.04 | 4.13 | 6.69 | 2.68 |
| Continued q.d. dosage regimen over 24 weeks | 50 mg q.d. N = 63 | 0.00 | 0.26 | −0.24 | 0.35 | 3.58 | 6.67 | 6.70 | 6.29 | 6.05 |
| | 100 mg q.d. N = 85 | 0.00 | 5.08 | 1.97 | 5.31 | 3.51 | 5.69 | 0.89 | 1.19 | 2.66 |
| | 200 mg q.d. N = 86 | 0.00 | 6.34 | 5.81 | 5.97 | 7.93 | 7.96 | 7.99 | 8.85 | 7.78 |
| Continued b.i.d. dosage regimen over 24 weeks | 25 mg b.i.d N = 69 | 0.00 | 2.79 | 3.88 | 4.15 | 3.83 | 7.21 | 6.54 | 7.42 | 8.14 |
| | 50 mg b.i.d. N = 85 | 0.00 | 4.19 | 3.43 | 7.11 | 4.75 | 2.33 | 5.78 | 7.08 | 8.29 |
| | 100 mg b.i.d. N = 84 | 0.00 | 8.14 | 6.19 | 7.69 | 13.14 | 11.86 | 9.44 | 7.71 | 12.88 |
| Increased dosage regimen at 12 weeks | from 50 mg q.d. to 100 mg q.d. N = 19 | 0.00 | 0.31 | 4.52 | −1.68 | 1.20 | 2.96 | 4.69 | 3.51 | 4.92 |
| | from 25 mg b.i.d. to 50 mg b.i.d N = 17 | 0.00 | 2.10 | 4.27 | −3.29 | −5.79 | −0.19 | 3.55 | −8.82 | 2.65 |

3.1.4.1.1 Study 2

TABLE LIV

[total cholesterol] Mean percentage CFB (%) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −1.80 | 0.96 | 4.15 | 5.77 |
| 2 | −1.96 | −0.18 | 4.96 | 7.74 |
| 4 | −1.22 | 2.91 | 8.28 | 9.35 |
| 8 | −0.93 | 5.45 | 7.75 | 9.62 |
| 12 | 0.07 | 4.08 | 12.45 | 13.12 |

TABLE LV

[total cholesterol] Median percentage CFB (%) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −3.01 | 2.12 | 2.38 | 5.37 |
| 2 | −1.13 | 0.00 | 2.65 | 6.90 |
| 4 | −2.51 | 0.00 | 5.40 | 7.39 |
| 8 | −1.41 | 4.90 | 6.08 | 9.01 |
| 12 | −2.67 | 3.43 | 6.41 | 11.96 |

TABLE LVI

[HDL] Mean percentage CFB (%) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −1.31 | 2.27 | 7.49 | 2.04 |
| 2 | −0.03 | 4.26 | 11.30 | 11.20 |
| 4 | 1.49 | 7.96 | 15.65 | 15.68 |
| 8 | 4.61 | 8.60 | 13.77 | 15.24 |
| 12 | 4.23 | 5.77 | 15.23 | 14.60 |

TABLE LVII

[HDL] Median percentage CFB (%) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −2.79 | 3.23 | 3.27 | 2.50 |
| 2 | −0.66 | 0.00 | 8.75 | 9.92 |
| 4 | 0.00 | 8.70 | 12.66 | 14.18 |
| 8 | 0.00 | 7.00 | 9.33 | 16.35 |
| 12 | 3.00 | 4.67 | 11.86 | 12.00 |

TABLE LVIII

[LDL] Mean percentage CFB (%) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −0.14 | −0.40 | 6.36 | 8.06 |
| 2 | −1.33 | −1.59 | 6.15 | 8.39 |
| 4 | −1.34 | 2.97 | 10.29 | 9.99 |
| 8 | −1.64 | 5.80 | 7.39 | 9.80 |
| 12 | −0.60 | 4.19 | 14.31 | 16.80 |

TABLE LIX

[LDL] Median percentage CFB (%) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −0.91 | 0.18 | 1.97 | 6.59 |
| 2 | −2.27 | −1.23 | −1.82 | 5.81 |
| 4 | −3.55 | 0.76 | 5.08 | 10.14 |
| 8 | −2.90 | 4.49 | 5.34 | 8.13 |
| 12 | −2.74 | 1.14 | 5.78 | 11.50 |

TABLE LX

[total cholesterol] Mean percentage CFB (%) - 24 weeks results

| Weeks | 0 | 1 | 2 | 4 | 8 | 12 | 16 | 20 | 24 |
|---|---|---|---|---|---|---|---|---|---|
| Placebo switching to 100 mg q.d. (N = 72) | 0.00 | −1.80 | −1.96 | −1.22 | −0.93 | 0.07 | 5.14 | 7.27 | 6.98 |
| 50 mg q.d. responders (N = 57) | 0.00 | 0.02 | −1.17 | 1.68 | 5.55 | 3.59 | 5.85 | 2.09 | 3.49 |
| 50 mg q.d. non responders switching to 100 mg q.d. (N = 15) | 0.00 | 4.56 | 3.50 | 7.51 | 5.10 | 5.83 | 9.72 | 9.75 | 10.66 |
| 100 mg q.d. (N = 70) | 0.00 | 4.15 | 4.96 | 8.28 | 7.75 | 12.45 | 10.96 | 10.06 | 11.75 |
| 200 mg q.d. (N = 69) | 0.00 | 5.77 | 7.74 | 9.35 | 9.62 | 13.12 | 11.40 | 11.67 | 12.83 |

TABLE LXI

[total cholesterol] Median percentage CFB (%) - 24 weeks results

| Weeks | 0 | 1 | 2 | 4 | 8 | 12 | 16 | 20 | 24 |
|---|---|---|---|---|---|---|---|---|---|
| Placebo switching to 100 mg q.d. (N = 72) | 0.00 | −3.01 | −1.13 | −2.51 | −1.41 | −2.67 | 3.87 | 5.09 | 5.57 |
| 50 mg q.d. responders (N = 57) | 0.00 | 0.35 | −0.82 | −0.51 | 5.74 | 1.01 | 2.92 | 3.75 | 5.44 |
| 50 mg q.d. non responders switching to 100 mg q.d. (N = 15) | 0.00 | 2.94 | 2.00 | 6.58 | 2.88 | 6.79 | 11.41 | 7.07 | 10.65 |
| 100 mg q.d. (N = 70) | 0.00 | 2.38 | 2.65 | 5.40 | 6.08 | 6.41 | 8.91 | 9.85 | 10.29 |
| 200 mg q.d. (N = 69) | 0.00 | 5.37 | 6.90 | 7.39 | 9.01 | 11.96 | 8.36 | 11.04 | 9.81 |

TABLE LXII

[HDL] Mean percentage CFB (%) - 24 weeks results

| Weeks | 0 | 1 | 2 | 4 | 8 | 12 | 16 | 20 | 24 |
|---|---|---|---|---|---|---|---|---|---|
| Placebo switching to 100 mg q.d. (N = 72) | 0.00 | −1.31 | −0.30 | 1.49 | 4.61 | 4.23 | 16.36 | 16.02 | 13.47 |
| 50 mg q.d. responders (N = 57) | 0.00 | 1.48 | 4.14 | 7.26 | 9.33 | 4.45 | 6.26 | 7.61 | 11.90 |
| 50 mg q.d. non responders switching to 100 mg q.d. (N = 15) | 0.00 | 5.25 | 4.69 | 10.56 | 5.96 | 10.42 | 14.57 | 16.39 | 20.96 |

TABLE LXII-continued

| | [HDL] Mean percentage CFB (%) - 24 weeks results | | | | | | | | |
|---|---|---|---|---|---|---|---|---|---|
| Weeks | 0 | 1 | 2 | 4 | 8 | 12 | 16 | 20 | 24 |
| 100 mg q.d. (N = 70) | 0.00 | 7.49 | 11.30 | 15.65 | 13.77 | 15.23 | 18.30 | 14.51 | 15.18 |
| 200 mg q.d. (N = 69) | 0.00 | 2.04 | 11.20 | 15.68 | 15.24 | 14.60 | 13.07 | 15.18 | 13.79 |

TABLE LXIII

| | [HDL] Median percentage CFB (%) - 24 weeks results | | | | | | | | |
|---|---|---|---|---|---|---|---|---|---|
| Weeks | 0 | 1 | 2 | 4 | 8 | 12 | 16 | 20 | 24 |
| Placebo switching to 100 mg q.d. (N = 72) | 0.00 | −2.79 | −0.66 | 0.00 | 0.00 | 3.00 | 10.82 | 13.11 | 11.36 |
| 50 mg q.d. responders (N = 57) | 0.00 | 2.78 | 0.00 | 8.30 | 8.81 | 4.00 | 2.82 | 5.63 | 8.70 |
| 50 mg q.d. non responders switching to 100 mg q.d. (N = 15) | 0.00 | 3.68 | 4.17 | 10.14 | 7.00 | 7.95 | 14.34 | 16.22 | 19.84 |
| 100 mg q.d. (N = 70) | 0.00 | 3.27 | 8.75 | 12.66 | 9.33 | 11.86 | 14.81 | 13.29 | 12.54 |
| 200 mg q.d. (N = 69) | 0.00 | 2.50 | 9.92 | 14.18 | 16.35 | 12.00 | 10.70 | 11.54 | 11.96 |

TABLE LXIV

| | [LDL] Mean percentage CFB (%) - 24 weeks results | | | | | | | | |
|---|---|---|---|---|---|---|---|---|---|
| Weeks | 0 | 1 | 2 | 4 | 8 | 12 | 16 | 20 | 24 |
| Placebo switching to 100 mg q.d. (N = 72) | 0.00 | −0.14 | −1.33 | −1.34 | −1.64 | −0.60 | 2.82 | 5.77 | 4.50 |
| 50 mg q.d. responders (N = 57) | 0.00 | −0.43 | −2.56 | 2.09 | 6.10 | 3.64 | 7.12 | 1.20 | 1.97 |
| 50 mg q.d. non responders switching to 100 mg q.d. (N = 15) | 0.00 | −0.30 | 1.96 | 6.21 | 4.76 | 6.13 | 6.76 | 3.33 | 3.17 |
| 100 mg q.d. (N = 70) | 0.00 | 6.36 | 6.15 | 10.29 | 7.39 | 14.31 | 12.10 | 12.84 | 14.01 |
| 200 mg q.d. (N = 69) | 0.00 | 8.06 | 8.39 | 9.99 | 9.80 | 16.80 | 12.24 | 14.33 | 17.10 |

TABLE LXV

| | [LDL] Median percentage CFB (%) - 24 weeks results | | | | | | | | |
|---|---|---|---|---|---|---|---|---|---|
| Weeks | 0 | 1 | 2 | 4 | 8 | 12 | 16 | 20 | 24 |
| Placebo switching to 100 mg q.d. (N = 72) | 0.00 | −0.91 | −2.27 | −3.55 | −2.90 | −2.74 | −1.52 | 1.00 | 4.13 |
| 50 mg q.d. responders (N = 57) | 0.00 | −0.29 | −2.27 | −1.14 | 5.33 | 0.69 | 7.71 | 3.91 | −0.19 |
| 50 mg q.d. non responders switching to 100 mg q.d. (N = 15) | 0.00 | 2.72 | −0.66 | 1.36 | 2.69 | 3.06 | 7.11 | −0.80 | 5.60 |
| 100 mg q.d. (N = 70) | 0.00 | 1.97 | −1.82 | 5.08 | 5.34 | 5.78 | 7.81 | 7.74 | 9.61 |
| 200 mg q.d. (N = 69) | 0.00 | 6.59 | 5.81 | 10.14 | 8.13 | 11.50 | 9.19 | 10.33 | 13.81 |

3.1.4.2. Study 3

The percentage changes at the end of the treatment (i.e. 10 days) with Compound 1 dosed as the [Compound 1:HCl:3H$_2$O] adduct are calculated vs baseline, and are reported in Table LXVI below.

TABLE LXVI

Figure 1:
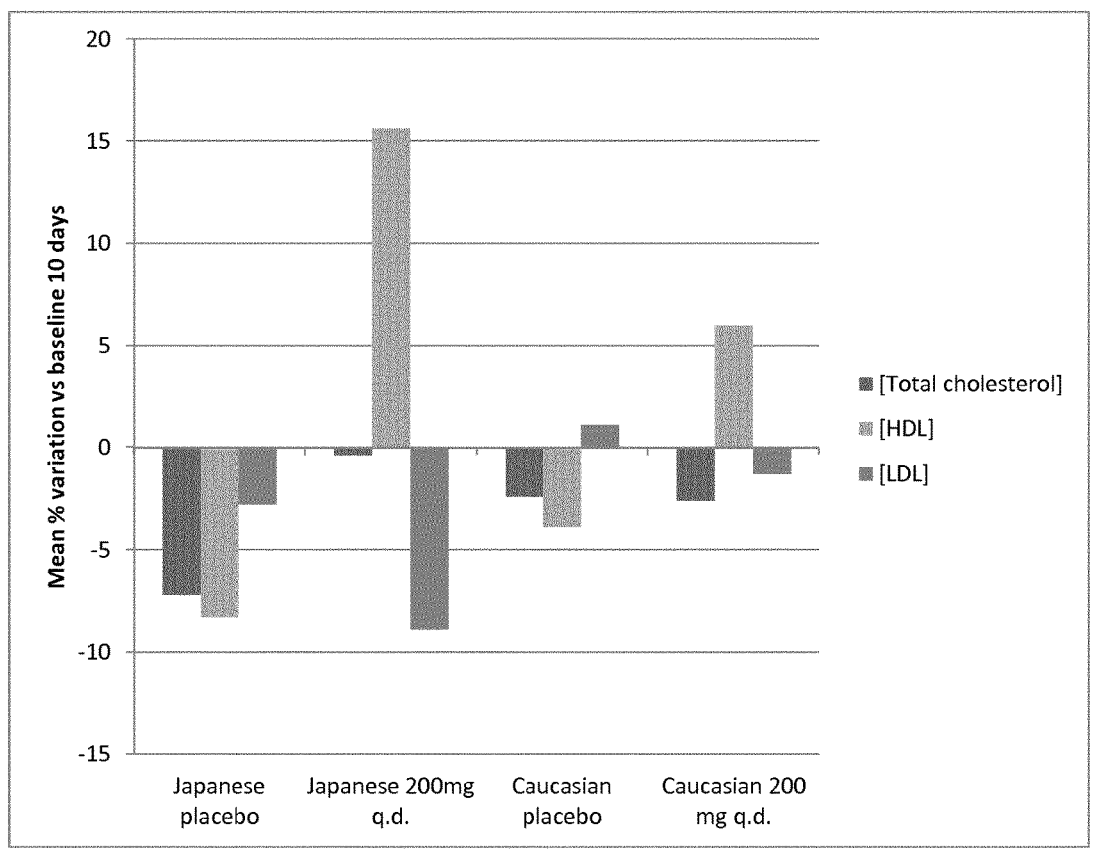
FIG. 1. Shows the mean percentage change in [Total Cholesterol], [HDL] and [LDL] vs baseline in Study 3 in Japanese and Caucasian healthy volunteers after 10 days treatment with Compound 1 (dosed as [Compound 1:HCl:3H$_2$O] at 200 mg/day.

Mean % variation vs baseline 10 days (FIG. 1)

| Dose | [Total cholesterol] % | [HDL] % | [LDL] % |
|---|---|---|---|
| Japanese placebo | −7.2 | −8.3 | −2.8 |
| Japanese 200 mg q.d. | −0.4 | 15.6 | −8.9 |
| Caucasian placebo | −2.4 | −3.9 | 1.1 |
| Caucasian 200 mg q.d. | −2.6 | 6 | −1.3 |

3.1.4.2.1 Study 4

The percentage changes at the end of the treatment (i.e. 4 weeks) with Compound 1 dosed as the [Compound 1:HCl:3H$_2$O] adduct are calculated vs baseline, and are reported in the table below.

TABLE LXVII

Figure 2:
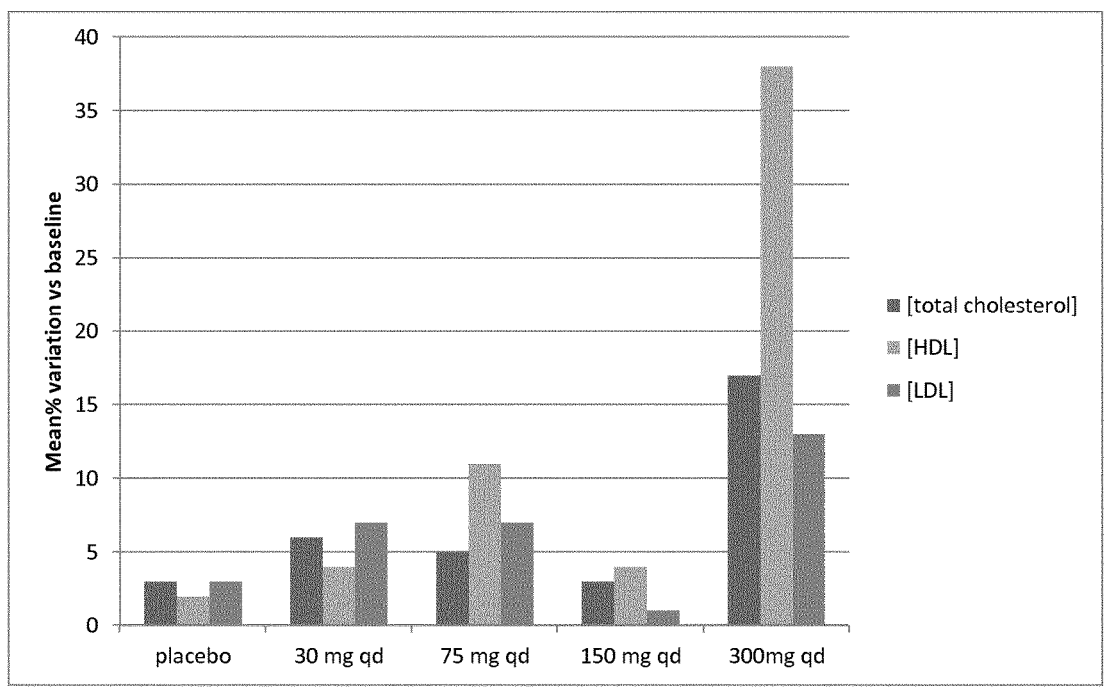
FIG. 2. Shows the mean percentage change in [Total Cholesterol], [HDL] and [LDL] vs baseline in Study 4 in RA patients upon administration of Compound 1 (dosed as [Compound 1:HCl:3H$_2$O] after 4 weeks treatment of varying doses (30 mg, 75 mg, 150 mg and 300 mg) once a day.

Mean % variation vs baseline after 4 weeks (FIG. 2)

| Dose | [Total cholesterol] % | [HDL] % | [LDL] % |
|---|---|---|---|
| placebo | 3 | 2 | 3 |
| 30 mg qd | 6 | 4 | 7 |
| 75 mg qd | 5 | 11 | 7 |
| 150 mg qd | 3 | 4 | 1 |
| 300 mg qd | 17 | 38 | 13 |

3.1.4.2.2 Study 5

TABLE LXVIII

[Total cholesterol] Mean CFB (%) - 10 weeks results

| Weeks | Placebo (N = 44) | 200 mg q.d. (N = 130) |
|---|---|---|
| 0 | — | — |
| 2 | 5.703 | 6.066 |
| 4 | 2.439 | 5.803 |
| 6 | 2.313 | 6.458 |
| 10 | 5.830 | 9.976 |

TABLE LXIX

[Total cholesterol] Median CFB (%) - 10 weeks results

| Weeks | Placebo (N = 44) | 200 mg q.d. (N = 130) |
|---|---|---|
| 0 | — | — |
| 2 | 5.369 | 4.148 |
| 4 | 1.370 | 3.803 |
| 6 | 0.000 | 7.187 |
| 10 | 4.710 | 7.456 |

TABLE LXX

[LDL] Mean CFB (%) - 10 weeks results

| Weeks | Placebo (N = 44) | 200 mg q.d. (N = 130) |
|---|---|---|
| 0 | — | — |
| 2 | 10.367 | 2.833 |
| 4 | 3.879 | 1.997 |
| 6 | 4.850 | 1.743 |
| 10 | 11.691 | 10.126 |

TABLE LXXI

[LDL] Median CFB (%) - 10 weeks results

| Weeks | Placebo (N = 44) | 200 mg q.d. (N = 130) |
|---|---|---|
| 0 | — | — |
| 2 | 7.482 | −1.469 |
| 4 | −0.840 | −1.986 |
| 6 | 2.796 | 0.992 |
| 10 | 10.127 | 6.299 |

TABLE LXXII

[HDL] Mean CFB (%) - 10 weeks results

| Weeks | Placebo (N = 44) | 200 mg q.d. (N = 130) |
|---|---|---|
| 0 | — | — |
| 2 | 5.557 | 17.940 |
| 4 | 5.112 | 19.414 |
| 6 | 3.645 | 20.199 |
| 10 | 3.073 | 19.734 |

TABLE LXXIII

[HDL] Median CFB (%) - 10 weeks results

| Weeks | Placebo (N = 44) | 200 mg q.d. (N = 130) |
|---|---|---|
| 0 | — | — |
| 2 | 4.125 | 16.867 |
| 4 | 3.399 | 15.333 |
| 6 | 2.419 | 16.867 |
| 10 | 1.587 | 15.789 |

TABLE LXXIV

[Total cholesterol] Mean CFB (%) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | 7.08 | 4.06 | 6.72 | 11.41 | 9.45 | 6.65 | 5.88 |
|  | To 100 mg q.d. (N = 22) | — | 4.32 | 1.11 | −1.09 | 2.03 | 2.49 | 2.84 | 1.90 |

TABLE LXXIV-continued

| | [Total cholesterol] Mean CFB (%) - 20 weeks results | | | | | | | | |
|---|---|---|---|---|---|---|---|---|---|
| Week 0 to week 10 | Week 10 to week 20 | Week 0 | Week 2 | Week 4 | Week 6 | Week 10 | Week 12 | Week 16 | Week 20 |
| 200 mg q.d. | Continued 200 mg q.d. (N = 77) | — | 7.30 | 5.06 | 6.70 | 11.58 | 11.06 | 11.13 | 11.03 |
| | To 100 mg q.d. (N = 30) | — | 4.54 | 6.72 | 6.47 | 9.72 | 5.38 | 2.89 | 3.80 |
| | To placebo (N = 23) | — | 3.98 | 6.98 | 5.72 | 5.28 | 1.82 | 5.24 | 3.92 |

TABLE LXXV

| | [Total cholesterol] Median CFB (%) - 20 weeks results | | | | | | | | |
|---|---|---|---|---|---|---|---|---|---|
| Week 0 to week 10 | Week 10 to week 20 | Week 0 | Week 2 | Week 4 | Week 6 | Week 10 | Week 12 | Week 16 | Week 20 |
| Placebo | Continued placebo (N = 22) | — | 5.44 | 4.58 | 7.69 | 8.37 | 4.43 | 5.94 | 8.97 |
| | To 100 mg q.d. (N = 22) | — | 5.30 | 0.46 | −1.04 | 0.32 | 0.41 | 0.19 | 2.81 |
| 200 mg q.d. | Continued 200 mg q.d. (N = 77) | — | 5.15 | 2.70 | 7.88 | 9.98 | 6.99 | 6.91 | 5.31 |
| | To 100 mg q.d. (N = 30) | — | 4.08 | 1.92 | 5.89 | 7.10 | 7.04 | 2.83 | 2.28 |
| | To placebo (N = 23) | — | 3.93 | 6.38 | 7.32 | 3.89 | 3.93 | 1.36 | 2.50 |

TABLE LXXVI

| | [LDL] Mean CFB (%) - 20 weeks results | | | | | | | | |
|---|---|---|---|---|---|---|---|---|---|
| Week 0 to week 10 | Week 10 to week 20 | Week 0 | Week 2 | Week 4 | Week 6 | Week 10 | Week 12 | Week 16 | Week 20 |
| Placebo | Continued placebo (N = 22) | — | 10.63 | 7.17 | 12.04 | 15.78 | 14.19 | 9.36 | 13.44 |
| | To 100 mg q.d. (N = 22) | — | 10.10 | 1.37 | −0.38 | 9.27 | 4.07 | 5.28 | 7.29 |
| 200 mg q.d. | Continued 200 mg q.d. (N = 77) | — | 3.14 | 1.21 | 0.73 | 14.77 | 9.98 | 12.35 | 11.56 |
| | To 100 mg q.d. (N = 30) | — | 2.17 | 4.07 | 2.59 | 5.40 | 5.91 | 2.18 | 2.73 |
| | To placebo (N = 23) | — | 2.69 | 1.85 | 3.72 | 4.43 | 4.55 | 10.32 | 6.12 |

TABLE LXXVII

| | [LDL] Median CFB (%) - 20 weeks results | | | | | | | | |
|---|---|---|---|---|---|---|---|---|---|
| Week 0 to week 10 | Week 10 to week 20 | Week 0 | Week 2 | Week 4 | Week 6 | Week 10 | Week 12 | Week 16 | Week 20 |
| Placebo | Continued placebo (N = 22) | — | 5.59 | −0.96 | 6.34 | 15.59 | 16.43 | 8.54 | 10.49 |
| | To 100 mg q.d. (N = 22) | — | 8.73 | −0.76 | −4.10 | 7.81 | 2.14 | −2.00 | 1.90 |
| 200 mg q.d. | Continued 200 mg q.d. (N = 77) | — | −2.51 | −2.16 | −0.61 | 8.26 | 5.42 | 7.42 | 6.93 |
| | To 100 mg q.d. (N = 30) | — | −1.37 | −1.98 | 1.25 | 7.46 | 6.39 | −1.36 | 1.65 |
| | To placebo (N = 23) | — | 0.71 | 2.44 | 3.51 | 1.84 | 6.33 | 6.34 | 5.24 |

TABLE LXXVIII

| | | \[HDL\] Mean CFB (%) - 20 weeks results | | | | | | | |
|---|---|---|---|---|---|---|---|---|---|
| Week 0 to week 10 | Week 10 to week 20 | Week 0 | Week 2 | Week 4 | Week 6 | Week 10 | Week 12 | Week 16 | Week 20 |
| Placebo | Continued placebo (N = 22) | — | 10.25 | 6.20 | 8.34 | 12.19 | 12.20 | 8.55 | 3.62 |
| | To 100 mg q.d. (N = 22) | — | 0.86 | 4.22 | 0.02 | −3.15 | 5.75 | 10.06 | 3.77 |
| 200 mg q.d. | Continued 200 mg q.d. (N = 77) | — | 18.29 | 15.66 | 19.93 | 17.97 | 16.97 | 13.90 | 11.15 |
| | To 100 mg q.d. (N = 30) | — | 20.28 | 25.33 | 25.93 | 26.29 | 14.27 | 11.19 | 15.54 |
| | To placebo (N = 23) | — | 13.75 | 23.62 | 13.52 | 14.87 | −3.87 | −7.46 | −8.40 |

TABLE LXXIX

| | | \[HDL\] Median CFB (%) - 10 weeks results | | | | | | | |
|---|---|---|---|---|---|---|---|---|---|
| Week 0 to week 10 | Week 10 to week 20 | Week 0 | Week 2 | Week 4 | Week 6 | Week 10 | Week 12 | Week 16 | Week 20 |
| Placebo | Continued placebo (N = 22) | — | 7.06 | 2.64 | 12.94 | 9.52 | 6.55 | 7.14 | 4.95 |
| | To 100 mg q.d. (N = 22) | — | −1.28 | 4.14 | 0.65 | −2.02 | 8.64 | 8.63 | 11.27 |
| 200 mg q.d. | Continued 200 mg q.d. (N = 77) | — | 17.33 | 9.91 | 13.98 | 12.50 | 9.94 | 12.22 | 10.66 |
| | To 100 mg q.d. (N = 30) | — | 17.11 | 16.75 | 23.04 | 19.61 | 10.66 | 2.24 | 10.18 |
| | To placebo (N = 23) | — | 13.54 | 27.96 | 13.45 | 15.66 | −1.75 | −3.07 | −4.82 |

3.1.5. Atherogenic Index

3.1.5.1. Principle

The atherogenic index has been identified to be a good predictor of cardiovascular disorders risks and is calculated as follows:

$$\frac{[total\ cholesterol]}{[HDL]}$$

As disclosed in the respective study protocols for Study 1 or 2, at week 12, depending on the outcome of their treatment, the subjects may be continued in their initial treatment course, or reassigned to another treatment group in a randomized blinded fashion until week 24. Therefore, the number of subjects (N) for the period of either 12 weeks, or 24 weeks is provided to reflect this redistribution at week 12.

Namely, in Study 1, at Week 12, the subjects on placebo who did not achieve at least a 20% improvement in swollen joint count (SJC66) and tender joint count (TJC68) were re-randomized automatically to receive Compound 1 (dosed as a [Compound 1:HCl:3H$_2$O]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d.

In Study 2, at Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.

3.1.5.2. Results

3.1.5.2.1 Study 1

After 12 weeks treatment, an atherogenic index variation of 0.2 fold decrease compared to pre-treatment baseline for the 100 mg/bid dose, and 0.35 fold decrease for the 200 mg q.d. was obtained, thus reducing the cardiovascular risk.

TABLE LXXX

| | Atherogenic index Mean CFB (mmol/L) (FIG. 6) | | | | | | |
|---|---|---|---|---|---|---|---|
| | | q.d. groups | | | b.i.d. groups | | |
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0.00 | 0.00 | 0.00 | 0.00 | 0.00 | 0.00 | 0.00 |
| 1 | −0.04 | −0.02 | −0.06 | −0.17 | 0.07 | −0.06 | −0.05 |
| 2 | −0.01 | −0.13 | −0.17 | −0.35 | −0.03 | −0.21 | −0.19 |

TABLE LXXX-continued

Figure 6:
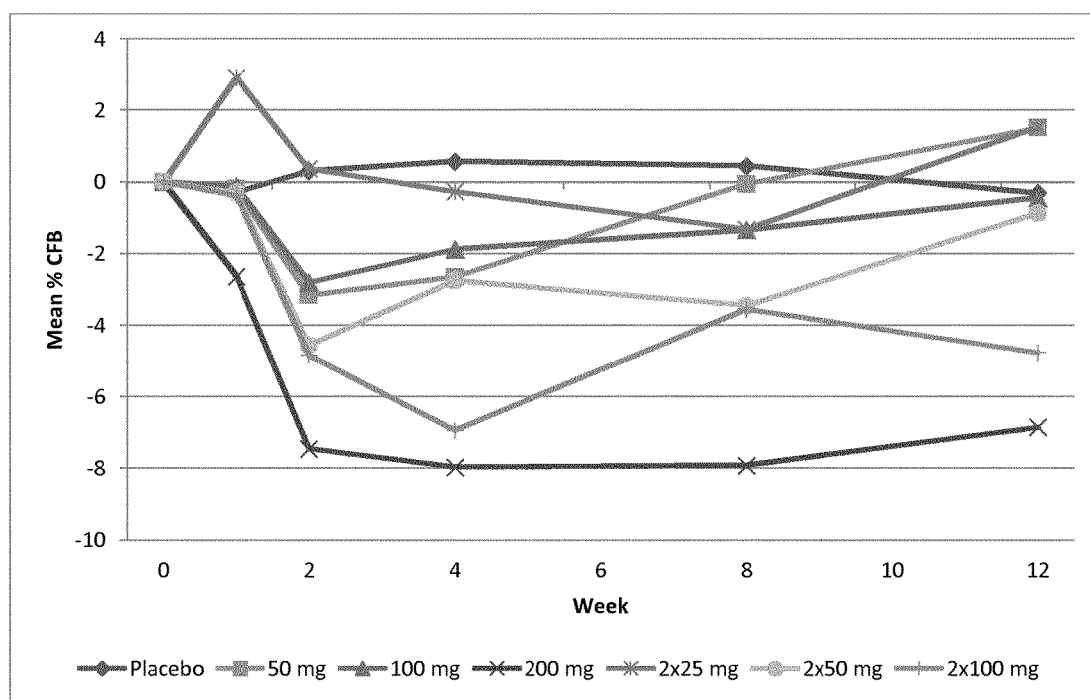
FIG. 6. Shows the mean percentage change vs baseline in atherogenic index in Study 1 in RA patients upon administration of Compound 1 (dosed as [Compound 1:HCl:3H$_2$O] after 12 weeks treatment of varying doses 25 mg b.i.d. (2×25 mg, asterisk), 50 mg b.i.d. (2×50 mg, filled circles), 50 mg q.d. (50 mg, filled squares), 100 mg b.i.d. (2×100 mg, upward crosses), 100 mg q.d. (100 mg, filled triangles), 200 mg q.d. (200 mg, tilted crosses), vs placebo (filled diamonds).
Figure 7A:
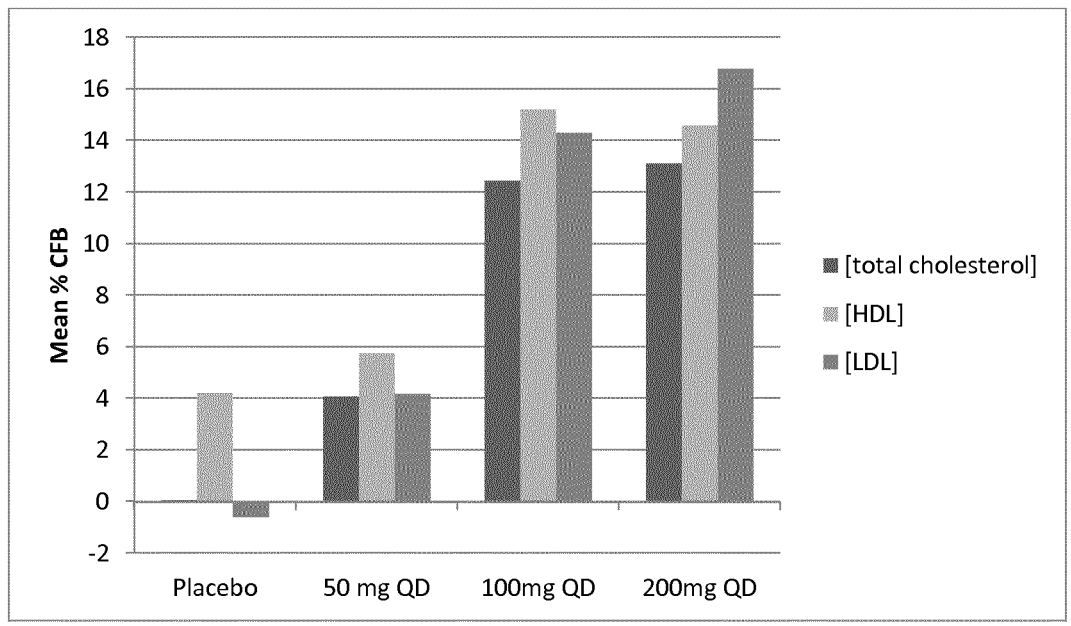
FIG. 7A shows the mean % variation, and FIG. 7B shows the median % variation.
Figure 7B:
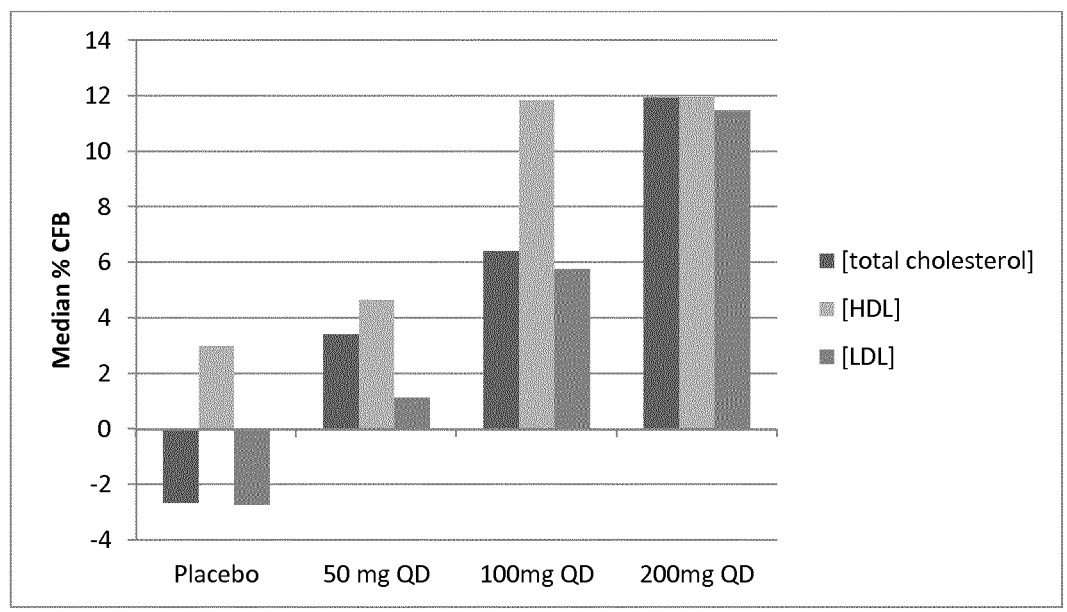
FIG. 7. Shows the percentage change in [Total Cholesterol], [HDL] and [LDL] vs baseline in Study 2 in RA patients upon administration of Compound 1 (dosed as [Compound 1:HCl:3H$_2$O] after 12 weeks treatment of varying doses 50 mg q.d., 100 mg q.d., and 200 mg q.d. vs placebo.
Figure 8A:
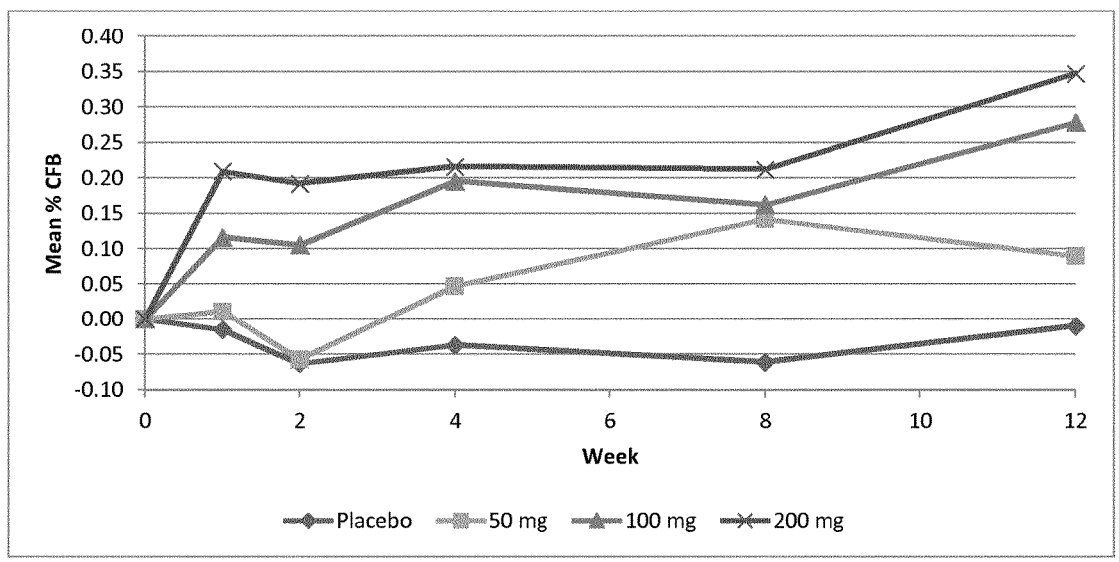
FIG. 8A shows the mean % variation, FIG. 8B shows the median % variation.
Figure 8B:
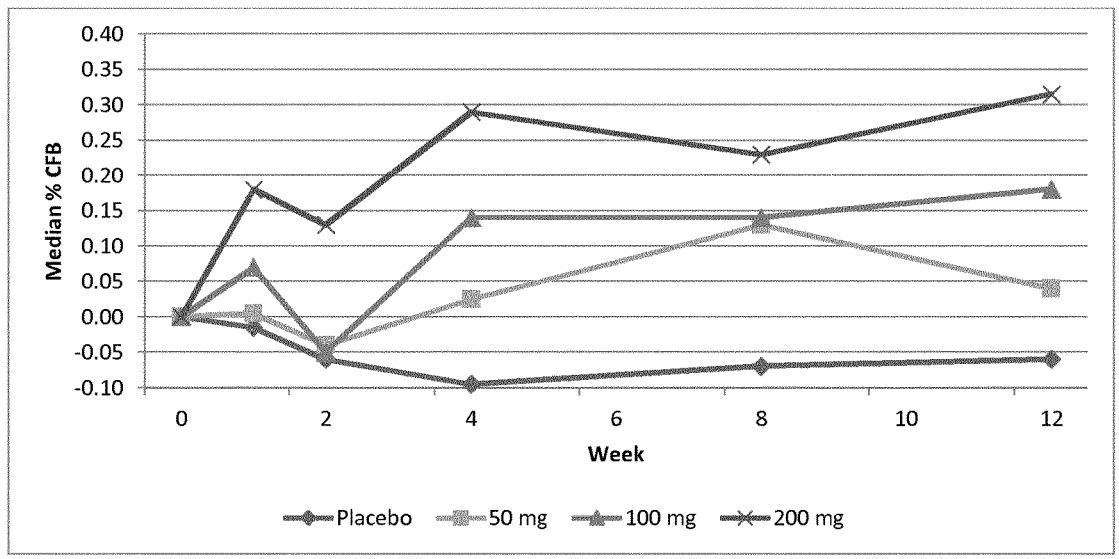
FIG. 8. Shows the percentage change vs baseline in [LDL] level in Study 2 in RA patients upon administration of Compound 1 (dosed as [Compound 1:HCl:3H$_2$O] after 12 weeks treatment of varying doses 50 mg q.d. (50 mg, filled squares), 100 mg q.d. (100 mg, filled triangles), 200 mg q.d. (200 mg, crosses), vs placebo (filled diamonds).
Figure 9A:
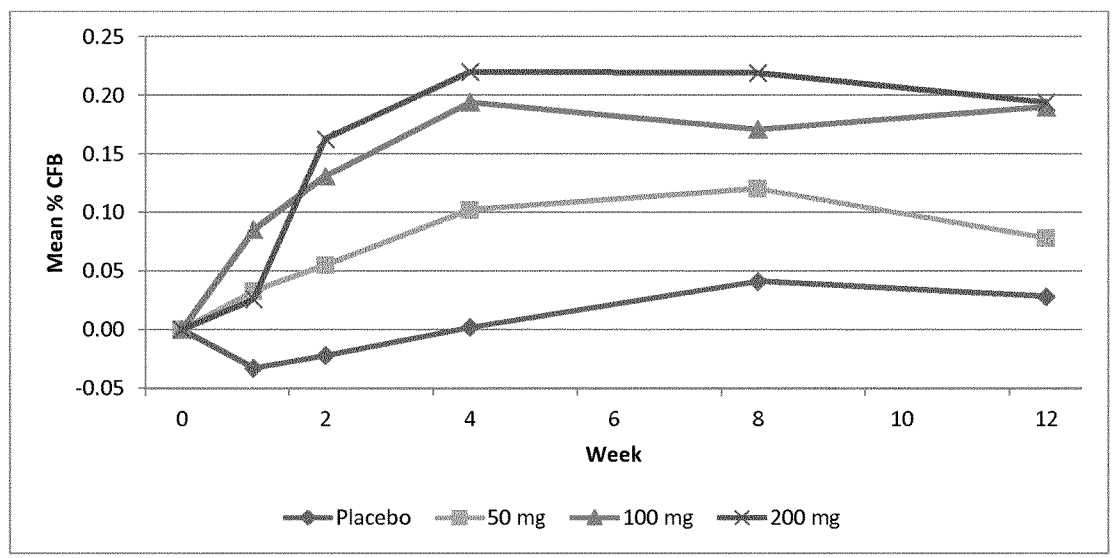
FIG. 9A shows the mean % variation, FIG. 9B shows the median % variation FIG. 10. Shows the mean percentage change vs baseline in atherogenic index in Study 2 in RA patients upon administration of Compound 1 (dosed as [Compound 1:HCl:3H$_2$O] after 12 weeks treatment of varying doses 50 mg q.d. (50 mg, filled squares), 100 mg q.d. (100 mg, filled triangles), 200 mg q.d. (200 mg, crosses), vs placebo (filled diamonds).
Figure 9B:
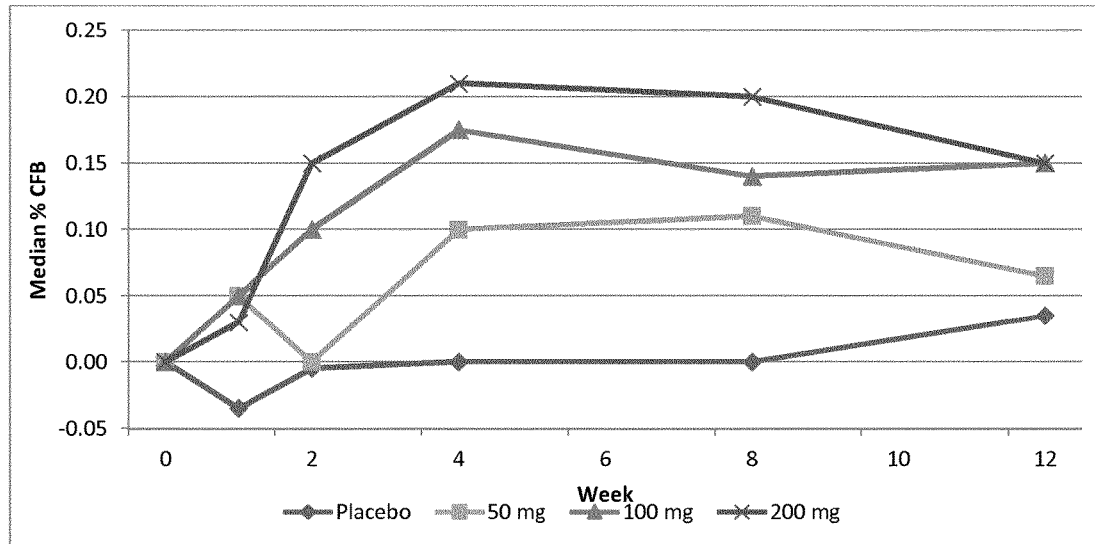
FIG. 9. Shows the mean percentage change vs baseline in [HDL] level in Study 2 in RA patients upon administration of Compound 1 (dosed as [Compound 1:HCl:3H$_2$O] after 12 weeks treatment of varying doses 50 mg q.d. (50 mg, filled squares), 100 mg q.d. (100 mg, filled triangles), 200 mg q.d. (200 mg, crosses), vs placebo (filled diamonds).
Figure 10:
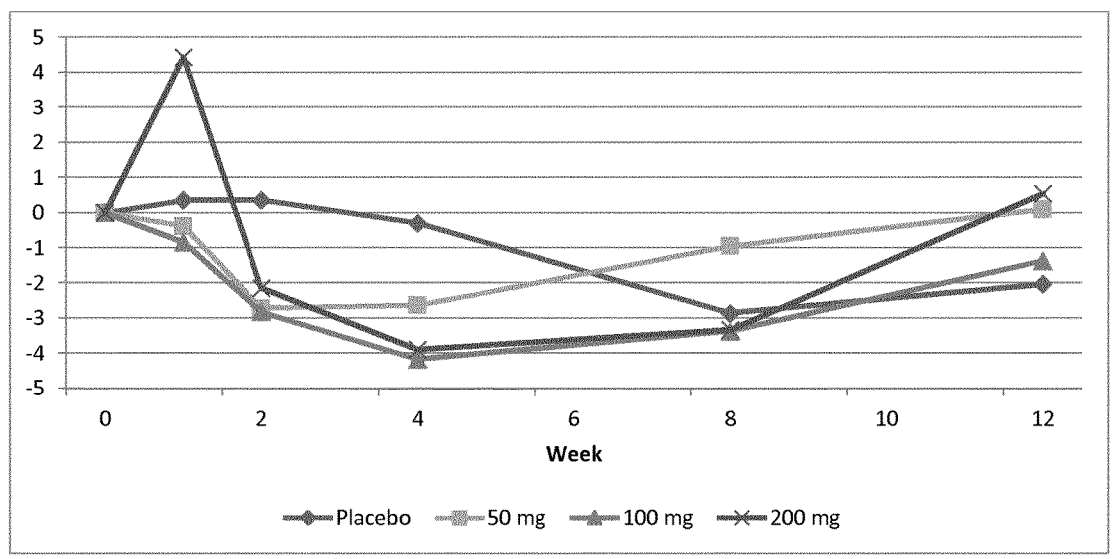
Figure 11A:
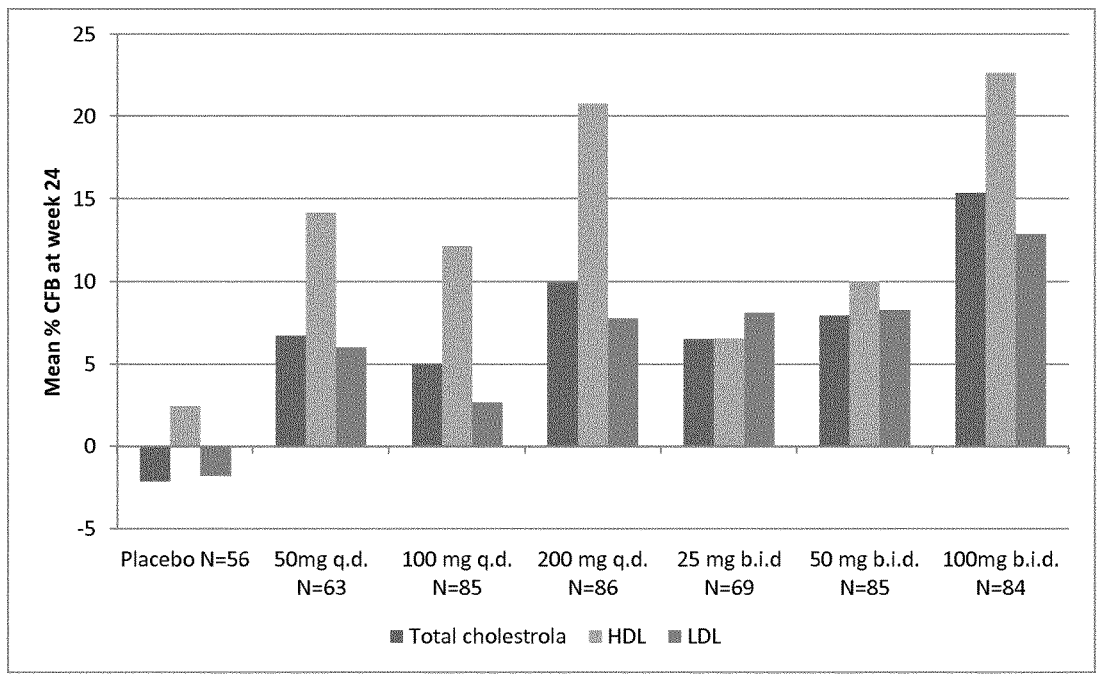
FIG. 11A shows the mean % change for continued groups at varying doses of 25 mg b.i.d. (2×25 mg in resp, asterisk), 50 mg b.i.d. (2×50 mg, filled circles), 50 mg q.d. (50 mg in resp, filled diamonds), 100 mg b.i.d. (2×100 mg, upward crosses), 100 mg q.d. (100 mg, filled triangles), 200 mg q.d. (200 mg, tilted crosses), vs placebo (Placebo in resp, filled squares).
Figure 11B:
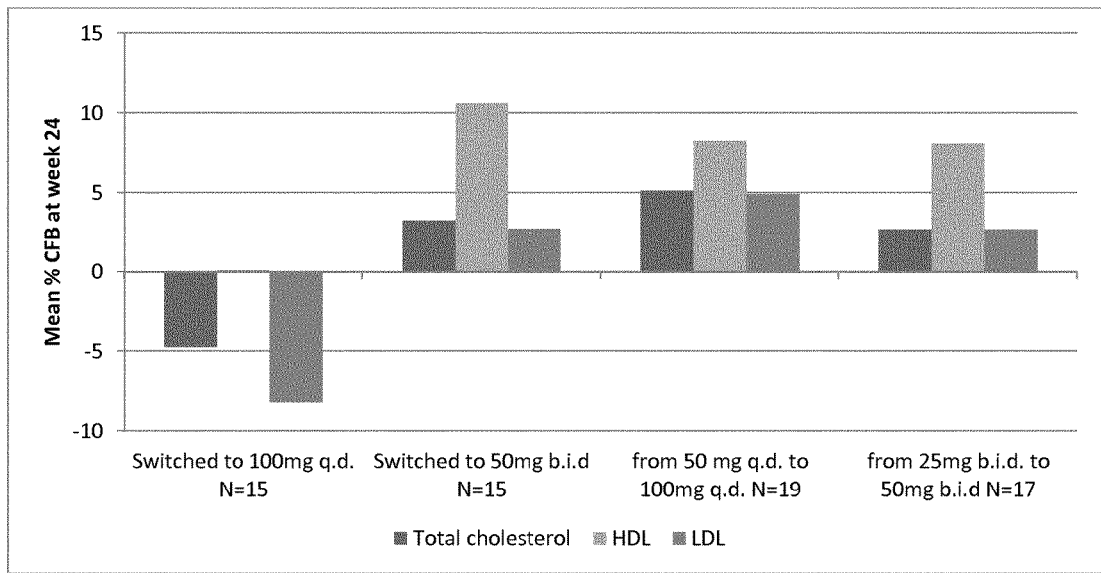
FIG. 11B shows the mean percentage change for switched groups from placebo to 100 mg q.d. (filled triangles), from placebo to 50 mg b.i.d. (filled circles), from 50 mg q.d to 100 mg q.d. (filled diamonds), from 25 mg b.i.d. to 50 mg b.i.d. (2×25 mg to 2×50 mg, filled squares).
Figure 12A:
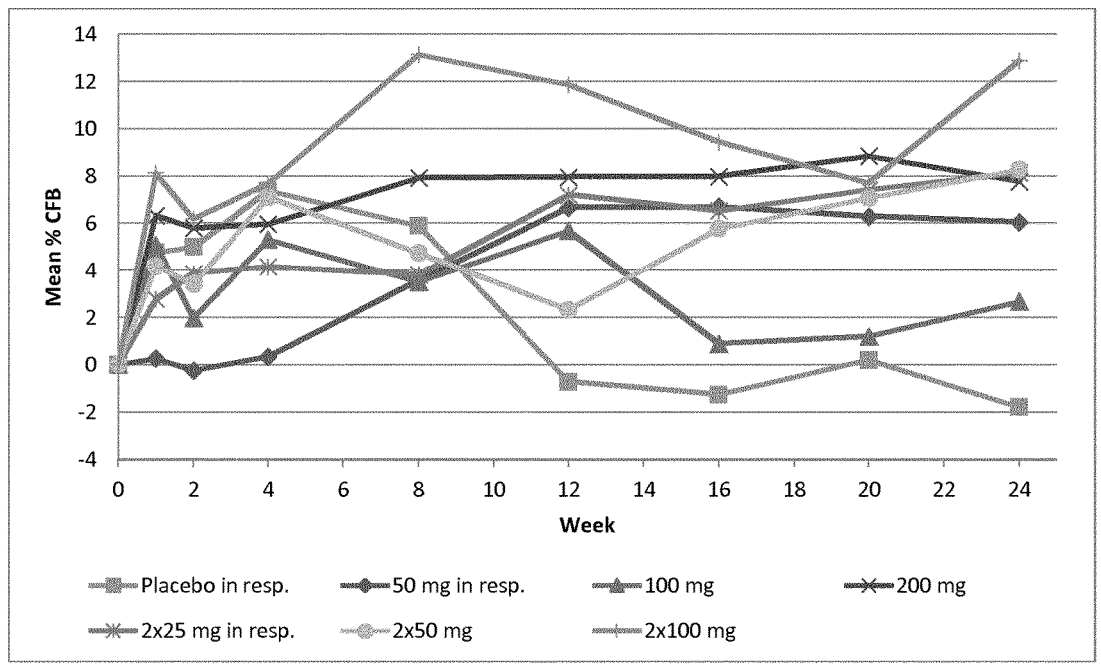
FIG. 12A shows the mean % change for continued groups at varying doses 25 mg b.i.d. (2×25 mg in resp, asterisk), 50 mg b.i.d. (2×50 mg, filled circles), 50 mg q.d. (50 mg in resp, filled diamonds), 100 mg b.i.d. (2×100 mg, upward crosses), 100 mg q.d. (100 mg, filled triangles), 200 mg q.d. (200 mg, tilted crosses), vs placebo (Placebo in resp, filled squares).
Figure 12B:
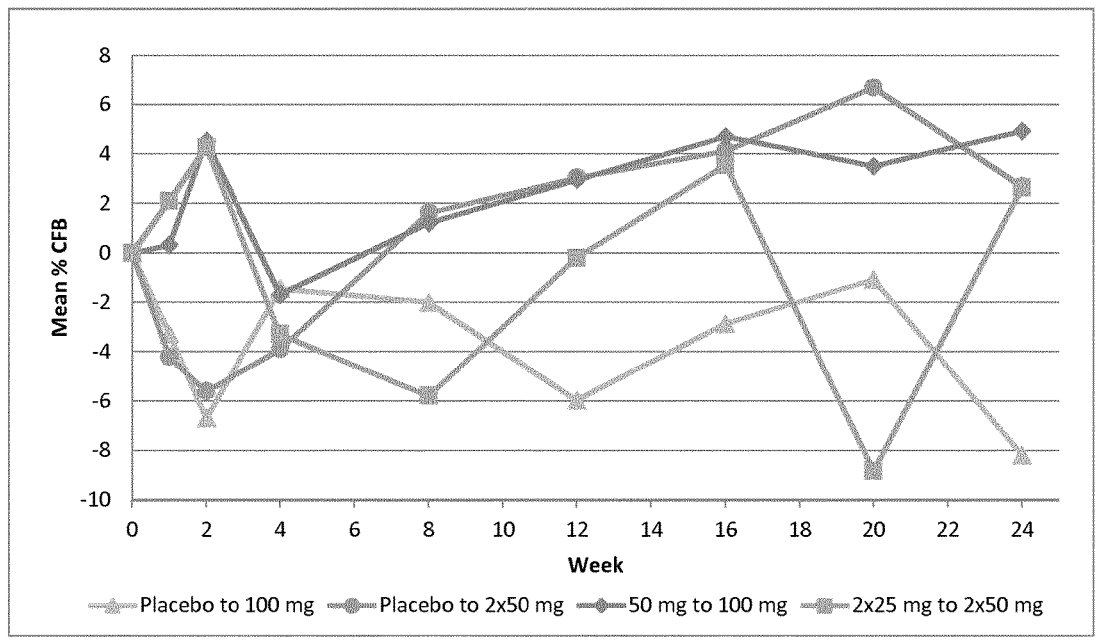
FIG. 12B shows the mean % change for switched groups from placebo to 100 mg q.d. (filled triangles), from placebo to 50 mg b.i.d. (filled circles), from 50 mg q.d to 100 mg q.d. (filled diamonds), from 25 mg b.i.d. to 50 mg b.i.d. (2×25 mg to 2×50 mg, filled squares).
Figure 13A:
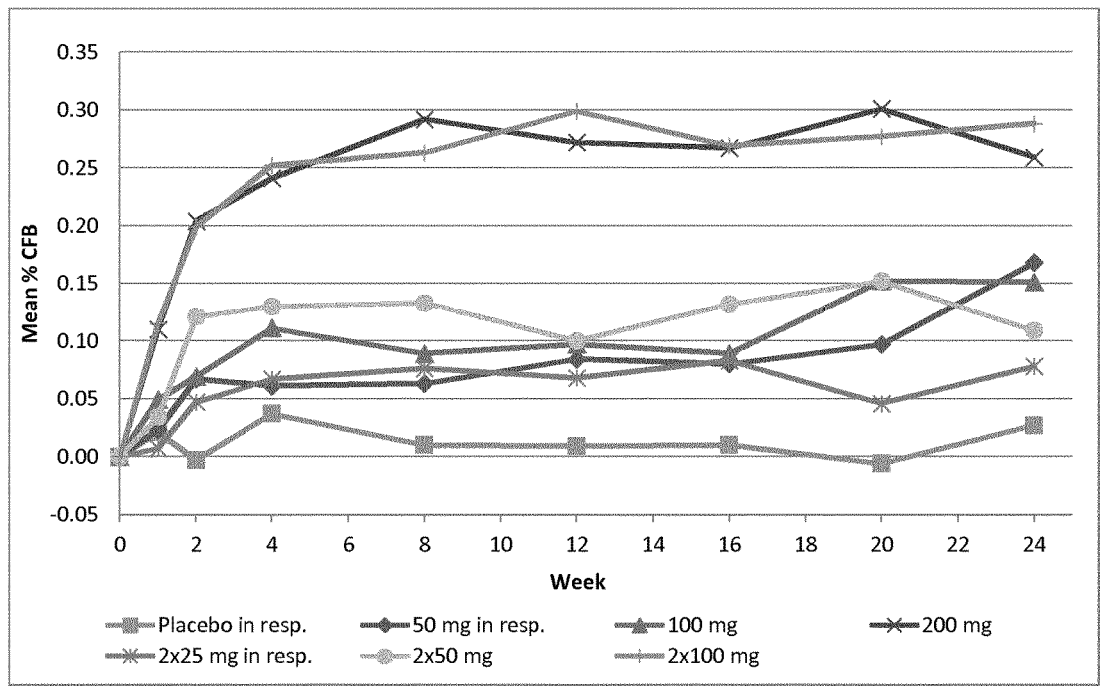
FIG. 13A shows the mean % change for continued groups at varying doses 25 mg b.i.d. (2×25 mg in resp, asterisk), 50 mg b.i.d. (2×50 mg, filled circles), 50 mg q.d. (50 mg in resp, filled diamonds), 100 mg b.i.d. (2×100 mg, upward crosses), 100 mg q.d. (100 mg, filled triangles), 200 mg q.d. (200 mg, tilted crosses), vs placebo (Placebo in resp, filled squares).
Figure 13B:
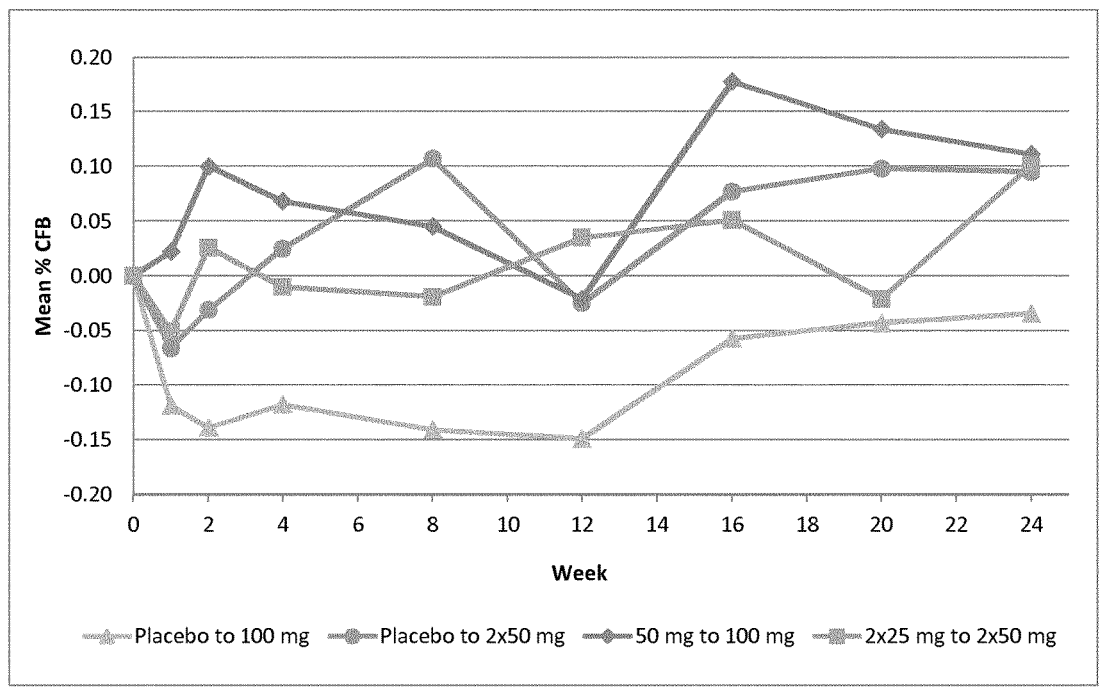
FIG. 13B shows the mean % change for switched groups from placebo to 100 mg q.d. (filled triangles), from placebo to 50 mg b.i.d. (filled circles), from 50 mg q.d to 100 mg q.d. (filled diamonds), from 25 mg b.i.d. to 50 mg b.i.d. (2×25 mg to 2×50 mg, filled squares).
Figure 14A:
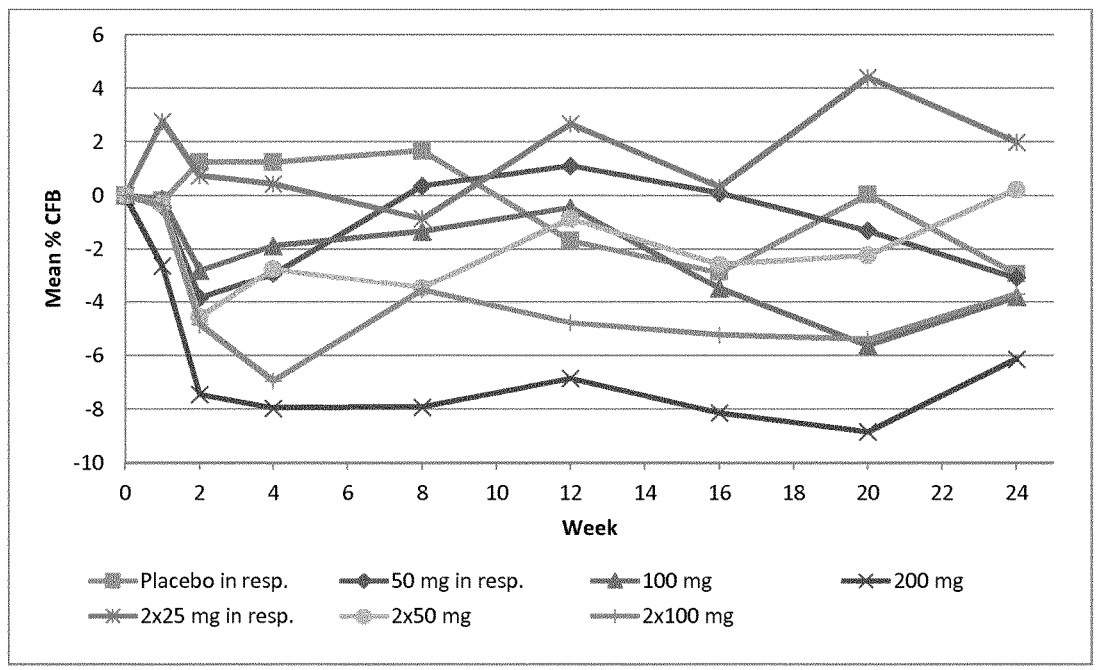
FIG. 14A shows the mean % change for continued groups at varying doses 25 mg b.i.d. (2×25 mg in resp, asterisk), 50 mg b.i.d. (2×50 mg, filled circles), 50 mg q.d. (50 mg in resp, filled diamonds), 100 mg b.i.d. (2×100 mg, upward crosses), 100 mg q.d. (100 mg, filled triangles), 200 mg q.d. (200 mg, tilted crosses), vs placebo (Placebo in resp, filled squares).
Figure 14B:
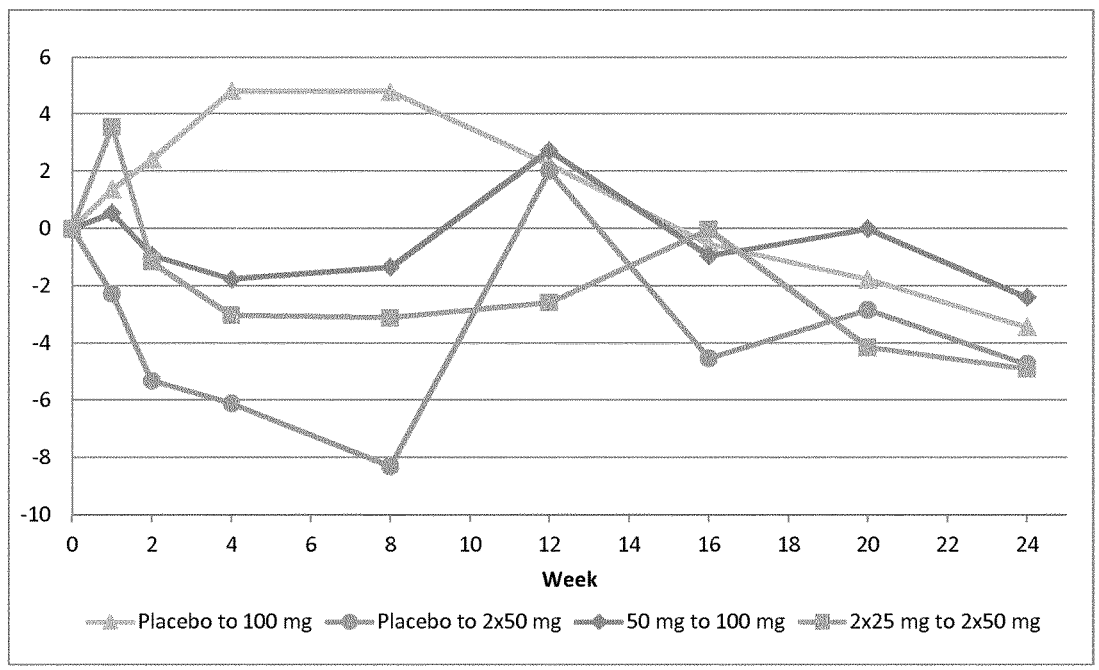
FIG. 14B shows the mean % change for switched groups from placebo to 100 mg q.d. (filled triangles), from placebo to 50 mg b.i.d. (filled circles), from 50 mg q.d to 100 mg q.d. (filled diamonds), from 25 mg b.i.d. to 50 mg b.i.d. (2×25 mg to 2×50 mg, filled squares).
Figure 15A:
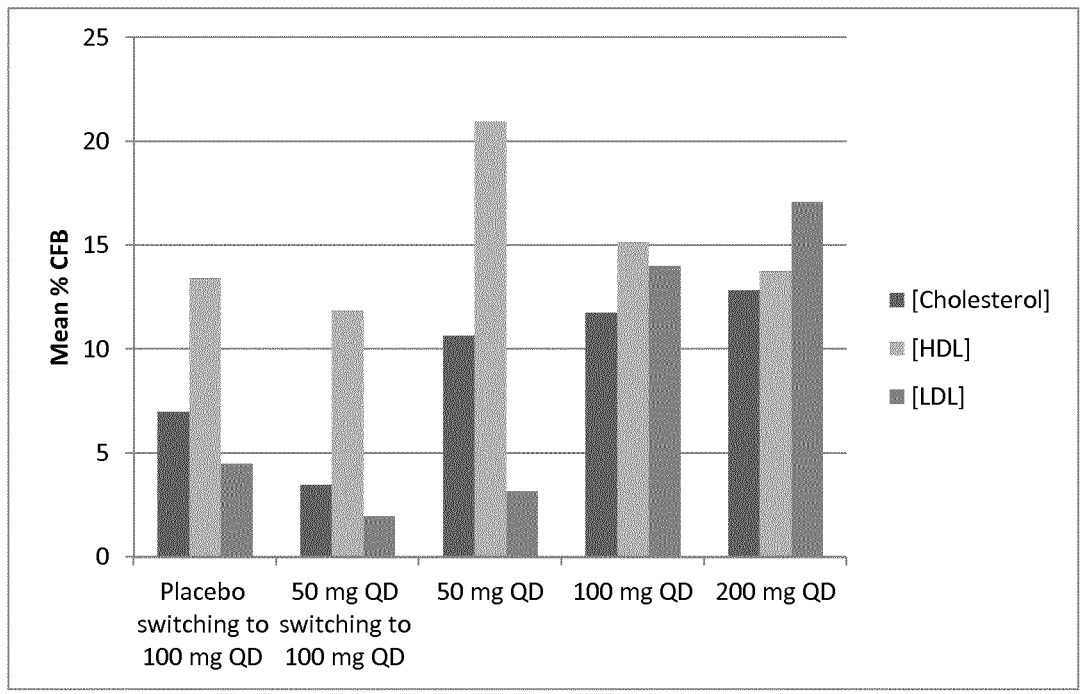
FIG. 15A shows the mean % variation and FIG. 15B shows the median % variation in the following groups: a) placebo switching to 100 mg q.d. at week 12, b) non-responders switching from 50 mg q.d. to 100 mg q.d. at week 12, c) continued 50 mg q.d., d) continued 100 mg q.d., and e) continued 200 mg q.d.
Figure 15B:
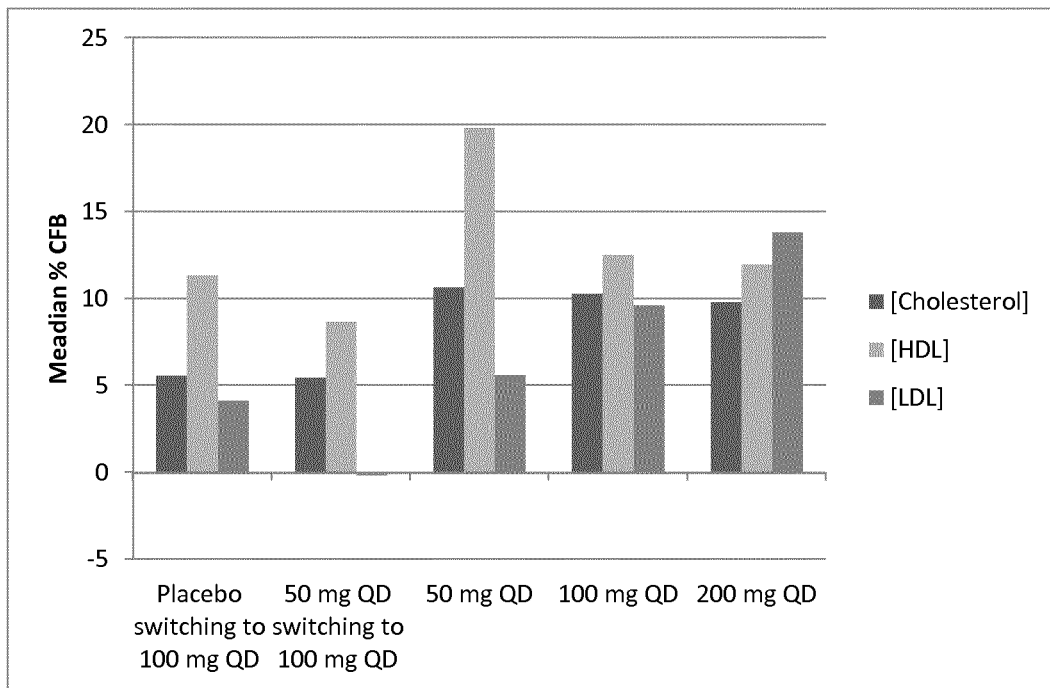
FIG. 15. Shows the mean percentage change in [Total Cholesterol], [HDL] and [LDL] vs baseline in the patient population upon administration of Compound 1 (dosed as [Compound 1:HCl:$3H_2O$] at 24 week time point for each dose in Study 2. At Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.
Figure 16A:
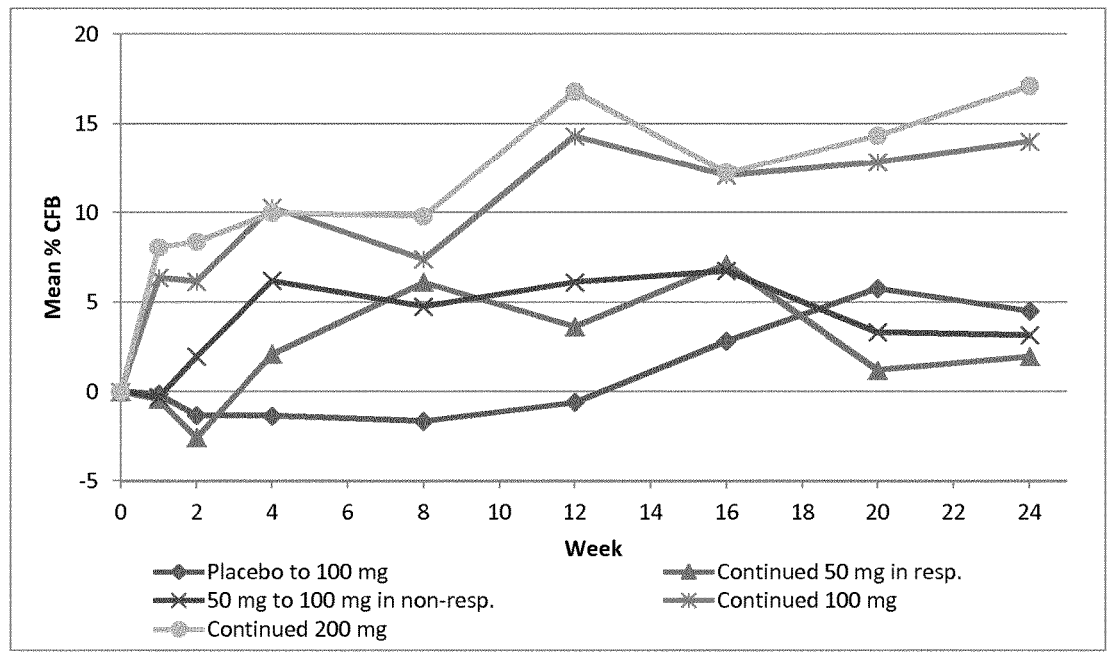
FIG. 16A shows the mean % variation, and FIG. 16B shows the median % variation in the following groups: a) placebo switching to 100 mg q.d. at week 12 (filled diamonds), b) non-responders switching from 50 mg q.d. to 100 mg q.d. at week 12 (tilted crosses), c) continued 50 mg q.d. (filled triangles), d) continued 100 mg q.d. (asterisks), and e) continued 200 mg q.d. (filled circles).
Figure 16B:
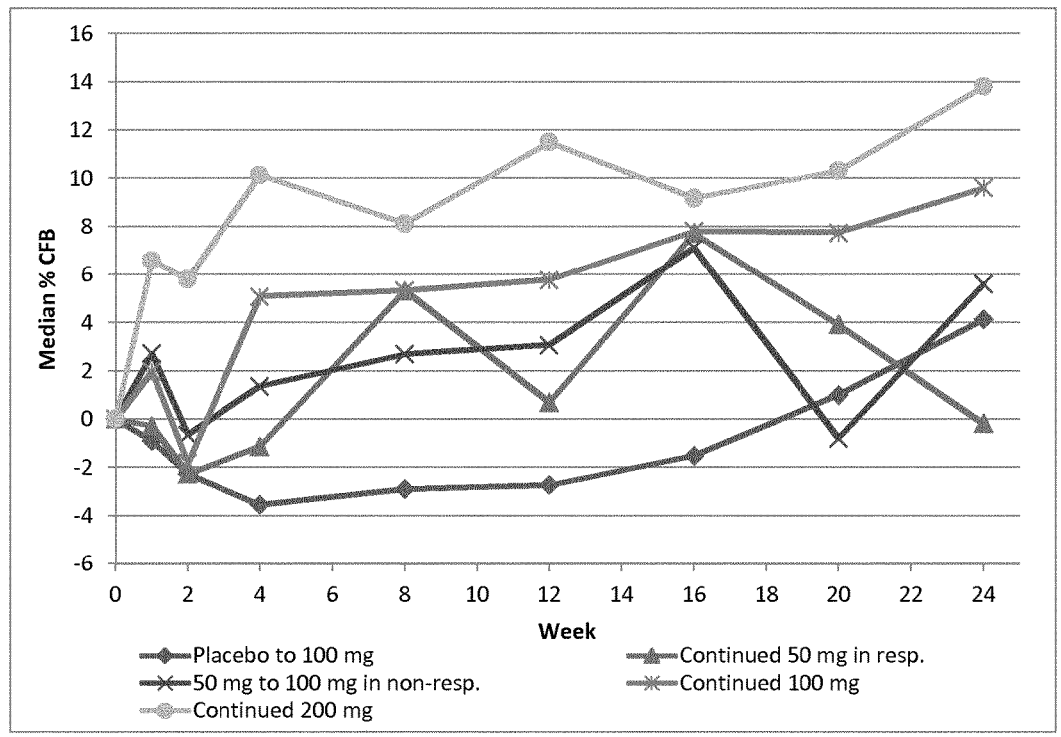
FIG. 16. Shows the percentage change vs baseline in [LDL] level in the patient population upon administration of Compound 1 (dosed as [Compound 1:HCl:$3H_2O$] at the 1, 2, 4, 8, 12, 16, 20 and 24 week time points for each dose in Study 2. At Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.
Figure 17A:
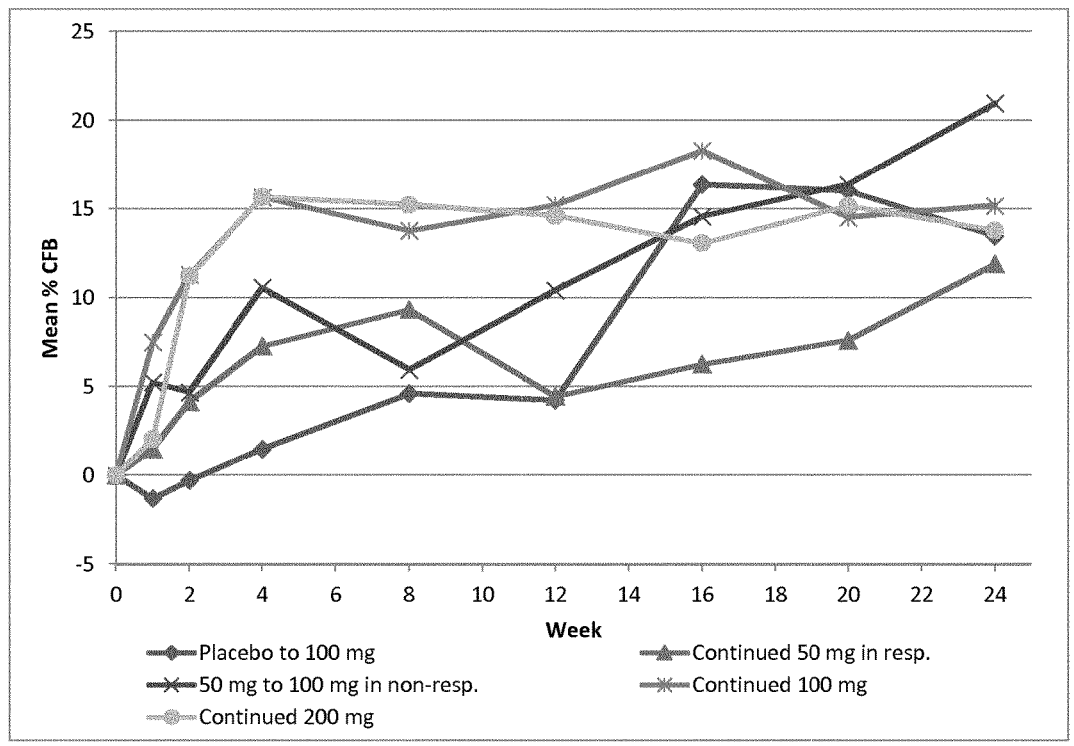
FIG. 17A shows the mean % variation, and FIG. 17B shows the median % variation in the following groups: a) placebo switching to 100 mg q.d. at week 12 (filled diamonds), b) non-responders switching from 50 mg q.d. to 100 mg q.d. at week 12 (tilted crosses), c) continued 50 mg q.d. (filled triangles), d) continued 100 mg q.d. (asterisks), and e) continued 200 mg q.d. (filled circles).
Figure 17B:
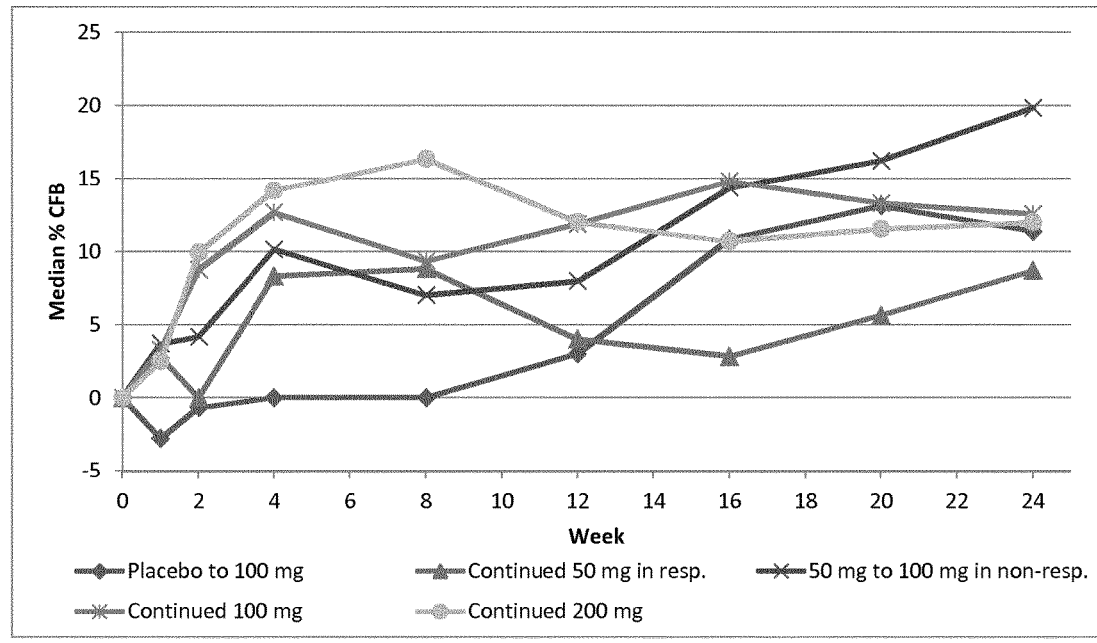
FIG. 17. Shows the mean percentage change vs baseline in [HDL] level in the patient population upon administration of Compound 1 (dosed as [Compound 1:HCl:$3H_2O$] at the 1, 2, 4, 8, 12, 16, 20 and 24 week time points for each dose in Study 2. At Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24. Subjects in the other groups maintained their randomized treatment until Week 24.
Figure 18:
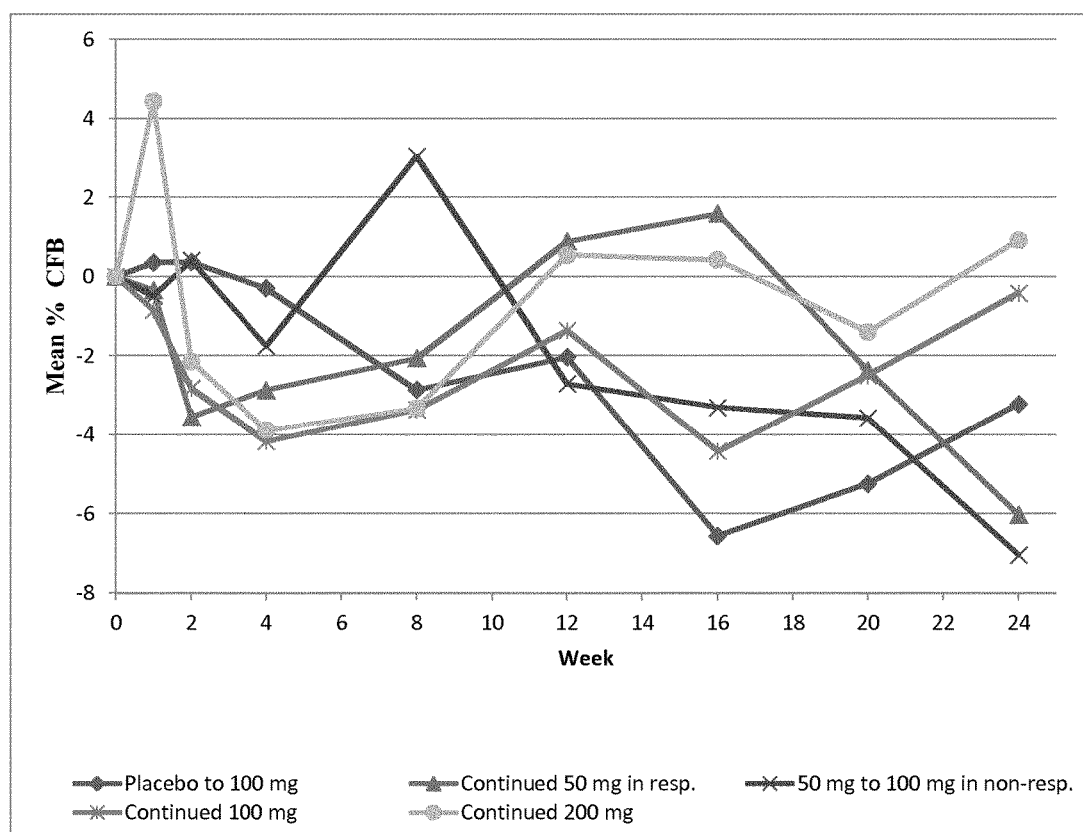
FIG. 18. Shows the mean percentage change vs baseline in atherogenic index in the patient population upon administration of Compound 1 (dosed as [Compound 1:HCl:$3H_2O$] at the 1, 2, 4, 8, 12, 16, 20 and 24 week time points for each dose in Study 2. At Week 12, all subjects on placebo and the subjects on the 50 mg dose who did not achieve at least 20% improvement in swollen joint count (SJC66) and tender joint count (TJC68) were assigned to 100 mg q.d. in a blinded fashion and continued treatment until Week 24.
Figure 19A:
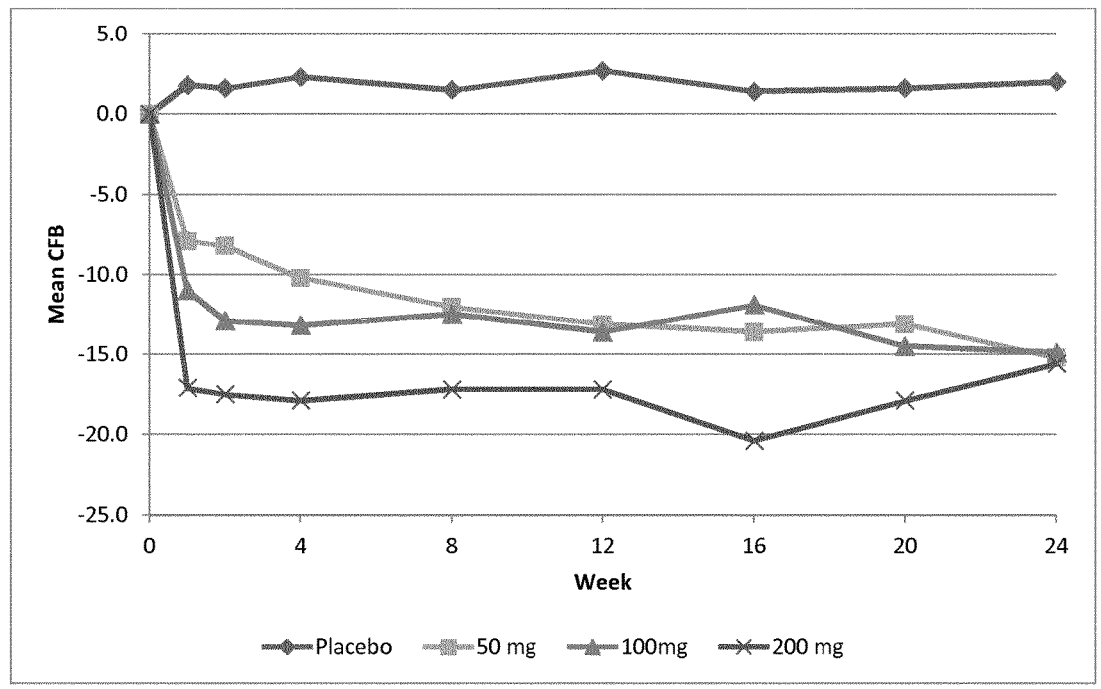
FIG. 19A shows the following groups: a) placebo (filled diamonds), b) 50 mg q.d. (filled squares), c) 100 mg q.d. (filled triangles) and d) 200 mg q.d. (tilted crosses).
Figure 19B:
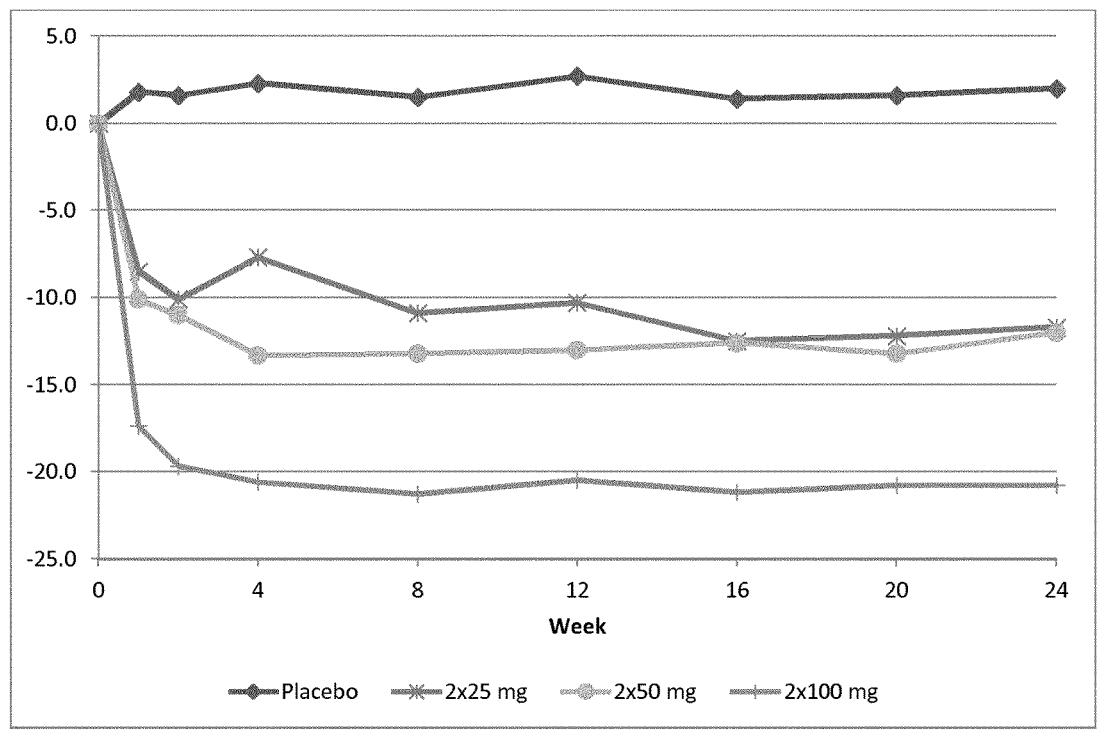
FIG. 19B shows the following groups: a) placebo (filled diamonds), b) 25 mg b.i.d. (asterisks), c) 50 mg b.i.d. (filled circles) and d) 100 mg b.i.d. (crosses). The results shown in the figures are calculated using Last-Observation-Carried-Forward (LOCF), which handles missing data by assigning the value recorded at the patient's last visit to all subsequent missed visits.
Figure 20:
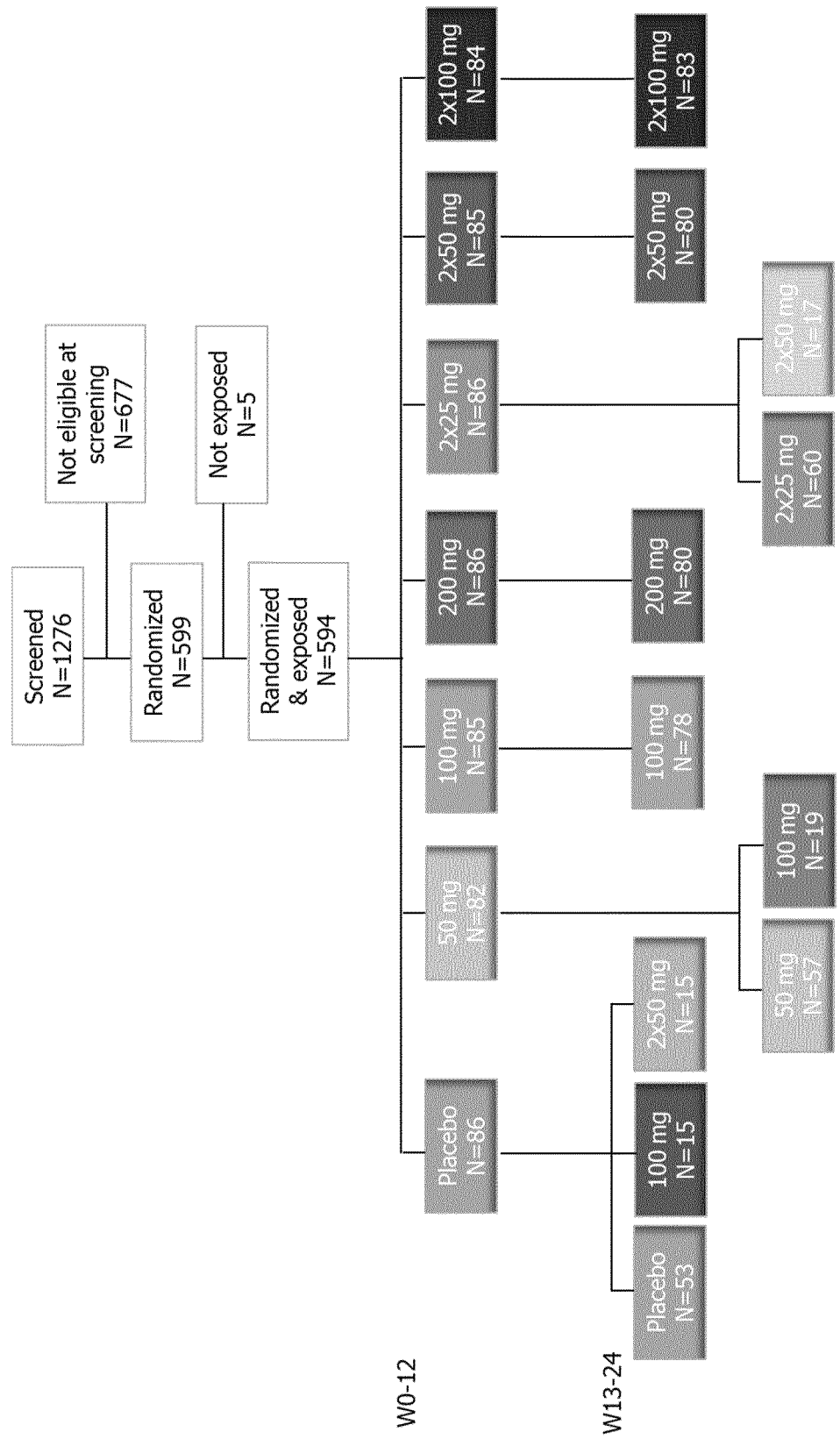
FIG. 20. Shows the patient distribution throughout Study 1 over the 24 weeks. From week 0 to 12, the patients were randomized and distributed within the following groups: a) placebo, b) 50 mg q.d., c) 100 mg q.d., d) 200 mg q.d., e) 25 mg b.i.d., f) 50 mg b.i.d., and 100 mg b.i.d. At Week 12, the subjects on placebo who did not achieve at least a 20% improvement in swollen joint count (SJC66) and tender joint count (TJC68) were re-randomized automatically to receive Compound 1 (dosed as a [Compound 1:HCl:$3H_2O$]) either at 100 mg q.d. or 50 mg b.i.d. doses in a blinded fashion; subjects on 50 mg q.d. who did not achieve at least a 20% improvement in SJC66 and TJC68 were assigned to 100 mg q.d. and subjects on 25 mg b.i.d. who did not achieve a 20% improvement in SJC66 and TJC68 were assigned to 50 mg b.i.d. Subjects who switched treatment at week 12 were handled as if they discontinued at week 12 for the purpose of statistical analysis, whereas subjects in the other groups maintained their randomized treatment until Week 24.

Atherogenic index Mean CFB (mmol/L) (FIG. 6)

| | q.d. groups | | | | b.i.d. groups | | |
|---|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 4 | −0.01 | −0.11 | −0.11 | −0.37 | −0.04 | −0.14 | −0.30 |
| 8 | −0.06 | −0.03 | −0.11 | −0.36 | −0.08 | −0.18 | −0.18 |
| 12 | −0.08 | 0.01 | −0.06 | −0.35 | 0.00 | −0.07 | −0.24 |

TABLE LXXXI

Atherogenic index Median CFB (mmol/L) (FIG. 6) -12 weeks results

| | q.d. groups | | | | b.i.d. groups | | |
|---|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0.00 | 0.00 | 0.00 | 0.00 | 0.00 | 0.00 | 0.00 |
| 1 | 0.00 | −0.10 | −0.10 | −0.10 | 0.10 | 0.00 | 0.00 |
| 2 | −0.10 | −0.20 | −0.10 | −0.25 | −0.10 | −0.10 | −0.20 |
| 4 | 0.00 | −0.10 | −0.10 | −0.30 | 0.00 | −0.10 | −0.30 |
| 8 | −0.10 | −0.10 | −0.10 | −0.30 | −0.10 | −0.10 | −0.20 |
| 12 | 0.00 | 0.00 | −0.10 | −0.30 | −0.10 | 0.00 | −0.10 |

TABLE LXXXII

Atherogenic index Mean percentage CFB (%) - 12 weeks results

| | q.d. groups | | | | b.i.d. groups | | |
|---|---|---|---|---|---|---|---|
| Weeks | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| 0 | 0 | 0 | 0 | 0 | 0 | 0 | 0 |
| 1 | 0 | 0 | 0 | −3 | 3 | 0 | 0 |
| 2 | 0 | −3 | −3 | −7 | 0 | −5 | −5 |
| 4 | 1 | −3 | −2 | −8 | 0 | −3 | −7 |
| 8 | 0 | 0 | −1 | −8 | −1 | −3 | −4 |
| 12 | 0 | 2 | 0 | −7 | 2 | −1 | −5 |

TABLE LXXXIII

Atherogenic index Mean CFB (mmol/L) - 24 weeks results

| Study groups | Dosage | Time points (weeks) | | | | | | | | |
|---|---|---|---|---|---|---|---|---|---|---|
| | | 0 | 1 | 2 | 4 | 8 | 12 | 16 | 20 | 24 |
| Placebo | Continued N = 56 | 0.00 | −0.04 | 0.02 | 0.01 | 0.01 | −0.10 | −0.15 | −0.02 | −0.10 |
| | Switched to 100 mg q.d. at week 12 N = 15 | 0.00 | 0.12 | 0.17 | 0.31 | 0.05 | 0.03 | −0.07 | −0.12 | −0.12 |
| | Switched to 50 mg b.i.d at week 12 N = 15 | 0.00 | −0.18 | −0.13 | −0.35 | −0.29 | −0.29 | −0.47 | −0.39 | −0.45 |
| Continued q.d. dosage regimen over 24 weeks | 50 mg q.d. N = 63 | 0.00 | −0.02 | −0.15 | −0.11 | 0.00 | 0.01 | −0.01 | −0.08 | −0.12 |
| | 100 mg q.d. N = 85 | 0.00 | −0.06 | −0.17 | −0.11 | −0.11 | −0.06 | −0.18 | −0.27 | −0.17 |
| | 200 mg q.d. N = 86 | 0.00 | −0.17 | −0.35 | −0.37 | −0.36 | −0.35 | −0.40 | −0.48 | −0.34 |
| Continued b.i.d. dosage regimen over 24 weeks | 25 mg b.i.d N = 69 | 0.00 | 0.08 | −0.01 | −0.02 | −0.05 | 0.05 | −0.03 | 0.09 | 0.02 |
| | 50 mg b.i.d. N = 85 | 0.00 | −0.06 | −0.21 | −0.14 | −0.18 | −0.07 | −0.13 | −0.11 | −0.04 |
| | 100 mg b.i.d. N = 84 | 0.00 | −0.05 | −0.19 | −0.30 | −0.18 | −0.24 | −0.25 | −0.24 | −0.18 |

TABLE LXXXIII-continued

Atherogenic index Mean CFB (mmol/L) - 24 weeks results

| Study groups | Dosage | \multicolumn{9}{c}{Time points (weeks)} |
|---|---|---|---|---|---|---|---|---|---|---|

| Study groups | Dosage | 0 | 1 | 2 | 4 | 8 | 12 | 16 | 20 | 24 |
|---|---|---|---|---|---|---|---|---|---|---|
| Increased dosage regimen at 12 weeks | from 50 mg q.d. to 100 mg q.d. N = 19 | 0.00 | −0.03 | −0.06 | −0.11 | −0.13 | 0.02 | −0.05 | 0.02 | −0.12 |
| | from 25 mg b.i.d. to 50 mg b.i.d N = 17 | 0.00 | 0.05 | −0.11 | −0.15 | −0.17 | −0.19 | −0.10 | −0.26 | −0.24 |

TABLE LXXXIV

Atherogenic index Median CFB (mmol/L) - 24 weeks results

| Study groups | Dosage | 0 | 1 | 2 | 4 | 8 | 12 | 16 | 20 | 24 |
|---|---|---|---|---|---|---|---|---|---|---|
| Placebo | Continued N = 56 | 0.00 | 0.00 | −0.10 | 0.00 | 0.00 | 0.00 | −0.20 | −0.10 | −0.10 |
| | Switched to 100 mg q.d. at week 12 N = 15 | 0.00 | −0.10 | 0.10 | 0.10 | 0.10 | 0.00 | 0.00 | −0.10 | −0.20 |
| | Switched to 50 mg b.i.d at week 12 N = 15 | 0.00 | −0.10 | −0.10 | −0.10 | 0.00 | −0.20 | −0.10 | −0.20 | −0.30 |
| Continued q.d. dosage regimen over 24 weeks | 50 mg q.d. N = 63 | 0.00 | −0.10 | −0.20 | −0.10 | −0.10 | 0.00 | 0.00 | −0.10 | −0.10 |
| | 100 mg q.d. N = 85 | 0.00 | −0.10 | −0.10 | −0.10 | −0.10 | −0.10 | −0.20 | −0.35 | −0.30 |
| | 200 mg q.d. N = 86 | 0.00 | −0.10 | −0.25 | −0.30 | −0.30 | −0.30 | −0.40 | −0.40 | −0.30 |
| Continued b.i.d. dosage regimen over 24 weeks | 25 mg b.i.d N = 69 | 0.00 | 0.10 | 0.00 | 0.00 | −0.10 | 0.00 | 0.00 | 0.00 | 0.00 |
| | 50 mg b.i.d. N = 85 | 0.00 | 0.00 | −0.10 | −0.10 | 0.00 | −0.10 | −0.10 | 0.00 | |
| | 100 mg b.i.d. N = 84 | 0.00 | 0.00 | −0.20 | −0.30 | −0.20 | −0.20 | −0.30 | −0.20 | −0.20 |
| Increased dosage regimen at 12 weeks | from 50 mg q.d. to 100 mg q.d. N = 19 | 0.00 | 0.00 | 0.10 | −0.10 | −0.10 | 0.20 | −0.10 | 0.00 | 0.00 |
| | from 25 mg b.i.d. to 50 mg b.i.d N = 17 | 0.00 | −0.10 | −0.20 | −0.10 | −0.10 | −0.30 | −0.30 | −0.30 | −0.30 |

TABLE LXXXV

Atherogenic index Mean percentage CFB (%) - 24 weeks results

| Study groups | Dosage | 0 | 1 | 2 | 4 | 8 | 12 | 16 | 20 | 24 |
|---|---|---|---|---|---|---|---|---|---|---|
| Placebo | Continued N = 56 | 0.00 | −0.19 | 1.25 | 1.24 | 1.68 | −1.69 | −2.87 | 0.04 | −2.92 |
| | Switched to 100 mg q.d. at week 12 N = 15 | 0.00 | 1.36 | 2.41 | 4.81 | 4.78 | 2.24 | −0.54 | −1.77 | −3.43 |
| | Switched to 50 mg b.i.d at week 12 N = 15 | 0.00 | −2.27 | 2.01 | −4.53 | −5.33 | −2.85 | −4.74 | −6.13 | −8.32 |
| Continued q.d. dosage regimen over 24 weeks | 50 mg q.d. N = 63 | 0.00 | −0.40 | −3.84 | −2.94 | 0.36 | 1.11 | 0.09 | −1.32 | −3.08 |
| | 100 mg q.d. N = 85 | 0.00 | −0.13 | −2.80 | −1.88 | −1.34 | −0.45 | −3.49 | −5.64 | −3.81 |
| | 200 mg q.d. N = 86 | 0.00 | −2.63 | −7.45 | −7.97 | −7.92 | −6.85 | −8.14 | −8.84 | −6.14 |
| Continued b.i.d. dosage regimen | 25 mg b.i.d N = 69 | 0.00 | 2.78 | 0.75 | 0.43 | −0.86 | 2.68 | 0.32 | 4.42 | 2.01 |
| | 50 mg b.i.d. N = 85 | 0.00 | −0.30 | −4.55 | −2.75 | −3.44 | −0.87 | −2.57 | −2.23 | 0.23 |

TABLE LXXXV-continued

Atherogenic index Mean percentage CFB (%) - 24 weeks results

| Study groups | Dosage | 0 | 1 | 2 | 4 | 8 | 12 | 16 | 20 | 24 |
|---|---|---|---|---|---|---|---|---|---|---|
| over 24 weeks | 100 mg b.i.d. N = 84 | 0.00 | −0.38 | −4.84 | −6.94 | −3.54 | −4.76 | −5.23 | −5.40 | −3.70 |
| Increased dosage regimen at 12 weeks | from 50 mg q.d. to 100 mg q.d. N = 19 | 0.00 | 0.53 | −0.94 | −1.77 | −1.35 | 2.72 | −0.95 | −0.01 | −2.40 |
|  | from 25 mg b.i.d. to 50 mg b.i.d N = 17 | 0.00 | 3.56 | −1.15 | −3.02 | −3.11 | −2.58 | −0.03 | −4.14 | −4.89 |

3.1.5.2.2 Study 2

The atherogenic index variation compared to pretreatment is presented in Table LXXXVI and Table LXXXVII below

TABLE LXXXVI

Atherogenic index Mean CFB (mmol/L) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | −0.04 | 0.00 | −0.05 | 0.15 |
| 2 | −0.06 | −0.10 | −0.11 | −0.09 |
| 4 | −0.07 | −0.13 | −0.19 | −0.18 |
| 8 | −0.14 | −0.03 | −0.13 | −0.16 |
| 12 | −0.12 | 0.01 | −0.07 | −0.04 |

TABLE LXXXVII

Atherogenic index Mean percentage CFB (%) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | 0.35 | −0.38 | −0.84 | 4.43 |
| 2 | 0.36 | −2.72 | −2.82 | −2.14 |
| 4 | −0.30 | −2.63 | −4.17 | −3.89 |
| 8 | −2.86 | −0.95 | −3.37 | −3.33 |
| 12 | −2.04 | 0.09 | −1.37 | 0.54 |

TABLE LXXXVIII

Atherogenic index Median CFB (mmol/L) - 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | 0.00 | 0.00 | 0.00 | 0.10 |
| 2 | 0.00 | −0.10 | −0.20 | 0.00 |
| 4 | 0.00 | −0.20 | −0.10 | −0.10 |
| 8 | 0.00 | −0.10 | −0.10 | −0.10 |
| 12 | −0.10 | −0.10 | −0.10 | 0.00 |

TABLE LXXXIX

Atherogenic index Median percentage CFB (%)- 12 weeks results

| Weeks | Placebo (N = 72) | 50 mg q.d. (N = 72) | 100 mg q.d. (N = 70) | 200 mg q.d. (N = 69) |
|---|---|---|---|---|
| 0 | 0.00 | 0.00 | 0.00 | 0.00 |
| 1 | 0.00 | 0.00 | 0.00 | 1.96 |
| 2 | 0.00 | −2.38 | −6.25 | 0.00 |
| 4 | 0.00 | −7.69 | −3.65 | −3.65 |
| 8 | 0.00 | −2.70 | −1.45 | −3.33 |
| 12 | −2.41 | −3.85 | −2.78 | 0.00 |

TABLE XC

Atherogenic index Mean CFB (mmol/L) - 24 weeks results

| | Weeks | | | | | | | | |
|---|---|---|---|---|---|---|---|---|---|
| | 0 | 1 | 2 | 4 | 8 | 12 | 16 | 20 | 24 |
| Placebo switching to 100 mg q.d. (N = 72) | 0.00 | −0.04 | −0.06 | −0.07 | −0.14 | −0.12 | −0.31 | −0.23 | −0.17 |
| 50 mg q.d. responders (N = 57) | 0.00 | −0.01 | −0.13 | −0.17 | −0.11 | 0.03 | 0.03 | −0.13 | −0.26 |
| 50 mg q.d. non responders switching to 100 mg q.d. (N = 15) | 0.00 | 0.03 | 0.04 | −0.01 | 0.23 | −0.05 | −0.11 | −0.09 | −0.23 |
| 100 mg q.d. (N = 70) | 0.00 | −0.05 | −0.11 | −0.19 | −0.13 | −0.07 | −0.18 | −0.08 | −0.06 |
| 200 mg q.d. (N = 69) | 0.00 | 0.15 | −0.09 | −0.18 | −0.16 | −0.04 | 0.01 | −0.10 | −0.02 |

TABLE XCI

Atherogenic index Mean percentage CFB (%) - 24 weeks results

| | Weeks | | | | | | | | |
|---|---|---|---|---|---|---|---|---|---|
| | 0 | 1 | 2 | 4 | 8 | 12 | 16 | 20 | 24 |
| Placebo switching to 100 mg q.d. (N = 72) | 0.00 | 0.35 | 0.36 | −0.30 | −2.86 | −2.04 | −6.56 | −5.24 | −3.22 |
| 50 mg q.d. responders (N = 57) | 0.00 | −0.34 | −3.56 | −2.87 | −2.06 | 0.89 | 1.59 | −2.38 | −6.03 |
| 50 mg q.d. non responders switching to 100 mg q.d. (N = 15) | 0.00 | −0.49 | 0.40 | −1.75 | 3.03 | −2.71 | −3.31 | −3.58 | −7.04 |
| 100 mg q.d. (N = 70) | 0.00 | −0.84 | −2.82 | −4.17 | −3.37 | −1.37 | −4.43 | −2.50 | −0.41 |
| 200 mg q.d. (N = 69) | 0.00 | 4.43 | −2.14 | −3.89 | −3.33 | 0.54 | 0.42 | −1.40 | 0.92 |

TABLE XCII

Atherogenic index Median CFB (mmol/L) - 24 weeks results

| | Weeks | | | | | | | | |
|---|---|---|---|---|---|---|---|---|---|
| | 0 | 1 | 2 | 4 | 8 | 12 | 16 | 20 | 24 |
| Placebo switching to 100 mg q.d. (N = 72) | 0.00 | 0.00 | 0.00 | 0.00 | 0.00 | −0.10 | −0.20 | −0.30 | −0.10 |
| 50 mg q.d. responders (N = 57) | 0.00 | −0.10 | −0.05 | −0.25 | −0.10 | −0.10 | 0.00 | −0.20 | −0.20 |
| 50 mg q.d. non responders switching to 100 mg q.d. (N = 15) | 0.00 | 0.00 | −0.10 | −0.20 | −0.20 | −0.20 | −0.20 | −0.20 | −0.30 |
| 100 mg q.d. (N = 70) | 0.00 | 0.00 | −0.20 | −0.10 | −0.10 | −0.10 | −0.20 | 0.00 | 0.00 |
| 200 mg q.d. (N = 69) | 0.00 | 0.10 | 0.00 | −0.10 | −0.10 | 0.00 | 0.00 | −0.20 | −0.10 |

TABLE XCIII

Atherogenic index Median percentage CFB (%) - 24 weeks results

| | Weeks | | | | | | | | |
|---|---|---|---|---|---|---|---|---|---|
| | 0 | 1 | 2 | 4 | 8 | 12 | 16 | 20 | 24 |
| Placebo switching to 100 mg q.d. (N = 72) | 0.00 | 0.00 | 0.00 | 0.00 | 0.00 | −2.41 | −5.40 | −7.87 | −3.57 |
| 50 mg q.d. responders (N = 57) | 0.00 | −2.04 | −1.28 | −7.69 | −2.39 | −2.56 | 0.00 | −4.04 | −5.77 |
| 50 mg q.d. non responders switching to 100 mg q.d. (N = 15) | 0.00 | 0.00 | −2.38 | −6.67 | −6.82 | −5.88 | −5.00 | −5.88 | −9.97 |
| 100 mg q.d. (N = 70) | 0.00 | 0.00 | −6.25 | −3.65 | −1.45 | −2.78 | −4.76 | 0.00 | 0.00 |
| 200 mg q.d. (N = 69) | 0.00 | 1.96 | 0.00 | −3.65 | −3.33 | 0.00 | 0.00 | −3.77 | −2.58 |

3.1.5.2.3 Study 5

TABLE XCIV

Atherogenic index Mean CFB (mmol/L) - 10 weeks results

| Weeks | Placebo (N = 44) | 200 mg q.d. (N = 130) |
|---|---|---|
| 0 | — | — |
| 2 | 0.02 | −0.31 |
| 4 | −0.11 | −0.33 |
| 6 | −0.01 | −0.32 |
| 10 | 0.14 | −0.25 |

TABLE XCV

Atherogenic index Median CFB (mmol/L) - 10 weeks results

| Weeks | Placebo (N = 44) | 200 mg q.d. (N = 130) |
|---|---|---|
| 0 | — | — |
| 2 | 0.04 | −0.31 |
| 4 | −0.16 | −0.28 |
| 6 | −0.08 | −0.29 |
| 10 | 0.10 | −0.21 |

TABLE XCVI

Atherogenic index Mean percentage CFB (%) - 10 weeks results

| Weeks | Placebo (N = 44) | 200 mg q.d. (N = 130) |
|---|---|---|
| 0 | — | — |
| 2 | 1.28 | −8.20 |
| 4 | −1.21 | −8.79 |
| 6 | 1.33 | −8.69 |
| 10 | 6.46 | −5.98 |

TABLE XCVII

Atherogenic index Mean CFB (mmol/L) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | −0.10 | −0.08 | 0.04 | 0.09 | −0.06 | −0.07 | 0.09 |
|  | To 100 mg q.d. (N = 22) | — | 0.14 | −0.13 | −0.05 | 0.18 | −0.08 | −0.17 | −0.01 |
| 200 mg q.d. | Continued 200 mg q.d. (N = 77) | — | −0.26 | −0.24 | −0.30 | −0.15 | −0.10 | −0.06 | 0.05 |
|  | To 100 mg q.d. (N = 30) | — | −0.48 | −0.54 | −0.51 | −0.45 | −0.21 | −0.21 | −0.32 |
|  | To placebo (N = 23) | — | −0.27 | −0.37 | −0.15 | −0.23 | 0.23 | 0.50 | 0.48 |

TABLE XCVIII

Atherogenic index Median CFB (mmol/L) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | −0.07 | −0.17 | −0.16 | −0.05 | −0.07 | −0.16 | 0.14 |
|  | To 100 mg q.d. (N = 22) | — | 0.06 | −0.15 | −0.02 | 0.11 | −0.10 | −0.25 | −0.10 |
| 200 mg q.d. | Continued 200 mg q.d. (N = 77) | — | −0.25 | −0.21 | −0.22 | −0.13 | −0.13 | −0.06 | 0.01 |
|  | To 100 mg q.d. (N = 30) | — | −0.37 | −0.38 | −0.48 | −0.48 | −0.25 | −0.15 | −0.39 |
|  | To placebo (N = 23) | — | −0.31 | −0.29 | −0.14 | −0.19 | 0.14 | 0.35 | 0.38 |

TABLE XCIX

Atherogenic index Mean percentage CFB (%) - 20 weeks results

| Week 0 to week 10 | Week 10 to week 20 | Week 0 | Week 2 | Week 4 | Week 6 | Week 10 | Week 12 | Week 16 | Week 20 |
|---|---|---|---|---|---|---|---|---|---|
| Placebo | Continued placebo (N = 22) | — | −1.47 | −0.01 | 1.82 | 2.72 | 0.03 | −0.53 | 3.16 |
|  | To 100 mg q.d. (N = 22) | — | 4.03 | −2.20 | 0.96 | 9.00 | 0.84 | −0.97 | 3.17 |
| 200 mg q.d. | Continued 200 mg q.d. (N = 77) | — | −6.93 | −6.67 | −8.51 | −3.49 | −1.27 | −0.22 | 3.38 |
|  | To 100 mg q.d. (N = 30) | — | −12.02 | −12.95 | −13.82 | −11.54 | −5.12 | −4.54 | −8.14 |
|  | To placebo (N = 23) | — | −7.38 | −10.10 | −2.55 | −5.14 | 9.34 | 19.14 | 19.82 |

3.2. Disease Activity Score 28 (DAS28)

The (DAS28(CRP)) is a system developed and validated by the European League Against Rheumatism (EULAR) to measure the progress and improvement of rheumatoid arthritis and has been extensively validated (Wells et al., 2008). The DAS28(CRP) scoring includes a 28 tender and swollen joint count, CRP measurement from blood analysis, and a general health assessment on a visual analog scale (Fransen et al., 2003).

DAS28(CRP) values range from 2.0 to 10.0, and more particularly reflect the following status:
Remission: DAS28(CRP)≤2.6
Low Disease activity: 2.6<DAS28(CRP)≤3.2
Moderate Disease Activity: 3.2<DAS28(CRP)≤5.1
High Disease Activity: DAS28(CRP)>5.1

In practice, the DAS28(CRP) measurement involves the evaluation 28 different joints including in the measurement (proximal interphalangeal joints (10 joints), metacarpophalangeal joints (10), wrists (2), elbows (2), shoulders (2), and knees (2)). When looking at these joints, both the number of joints with tenderness upon touching and swelling are counted.

Secondly, the C-reactive protein level (CRP) is measured.

Finally, the patient makes a subjective assessment of disease activity during the preceding 7 days on a scale between 0 and 100, where 0 is "no activity" and 100 is "highest activity possible".

The DAS28(CRP) score is then calculated as follows:

Firstly, the patient is asked to make a vertical mark on a 100 mm Visual Analog Scale (VAS) corresponding to their general health or global disease activity. Using an electronic touchscreen, the mark is measured from the left-hand side in mm to obtain the VAS value, which is used in the formula below.

Secondly, a swollen and tender joint examination is then performed on the patient. The swollen and tender joints are recorded. From this examination are obtained the total amount of swollen joints (SJC) and the total amount of tender joints (TJC), which are used in the formula below.

Thirdly, C-reactive protein (CRP) levels (in mg/dL) are measured.

Finally, the values obtained above (VAS, JTC28, SJC28, and CRP) are computed into the following Formula to obtain the DAS28(CRP) score.

$$DAS28(CRP) = 0.56 * \sqrt{TJC28} + 0.28\sqrt{SJC28} + 0.25\ln(CRP+1) + 0.014 * VAS$$

The number of subjects (N) provided in each groups corresponds to the number of patients starting the study in each group, and the DAS28 (CRP) data reported below corresponds to the responding patients continuing for the entire 24 weeks on their initial treatment course.

3.2.1.1. Results

3.2.1.1.1 Study 1

The DAS28(CRP) variation after 12 weeks treatment is presented in Table C below

TABLE C

| | | q.d. groups | | | b.i.d. groups | | |
|---|---|---|---|---|---|---|---|
| | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| Week 1 DAS28(CRP) mean CFB (LOCF) (p-value vs placebo) | −0.56 | −0.65 (0.6456) | −1.01 (0.0139) | −1.17 (0.0003) | −0.68 (0.6456) | −0.84 (0.2320) | −1.33 (<0.0001) |
| Week 2 DAS28(CRP) mean CFB (LOCF) (p-value vs placebo) | −0.80 | −0.94 (0.4820) | −1.50 (0.0002) | −1.52 (0.0002) | −1.06 (0.3074) | −1.22 (0.0535) | −1.84 (<0.0001) |
| Week 4 DAS28(CRP) mean CFB (LOCF) (p-value vs placebo) | −0.97 | −1.28 (0.1226) | −1.88 (<0.0001) | −1.92 (<0.0001) | −1.45 (0.0275) | −1.65 (0.0012) | −2.28 (<0.0001) |
| Week 8 DAS28(CRP) mean CFB (LOCF) (p-value vs placebo) | −1.15 | −1.66 (0.0129) | −2.12 (<0.0001) | −2.30 (<0.0001) | −1.82 (0.0018) | −1.93 (0.0003) | −2.72 (<0.0001) |
| Week 12 DAS28(CRP) mean CFB (LOCF) (p-value vs placebo) | −1.20 | −1.75 (0.0105) | −2.21 (<0.0001) | −2.49 (<0.0001) | −1.88 (0.0026) | −2.10 (<0.0001) | −2.84 (<0.0001) |
| % patients reaching low disease activity at week 12 (LOCF) | 7% | 12% | 13% | 15% | 13% | 11% | 14% |
| % patients reaching remission at week 12 (LOCF) | 7% | 12% | 21% | 22% | 15% | 18% | 36% |
| % patients reaching low disease activity and/or remission at week 12 (LOCF) | 14% | 24% | 34% | 37% | 28% | 29% | 50% |

TABLE CI

Study 1 - DAS28(CRP) scores - 24 weeks results

| | | q.d. groups | | | b.i.d. groups | | |
|---|---|---|---|---|---|---|---|
| | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| Week 1 DAS28(CRP) mean CFB (LOCF) (p-value vs placebo) | −0.57 | −0.65 (0.6483) | −1.00 (0.0179) | −1.17 (0.0003) | −0.68 (0.6483) | −0.84 (0.2424) | −1.33 (<0.0001) |
| Week 2 DAS28(CRP) mean CFB (LOCF) (p-value vs placebo) | −0.80 | −0.94 (0.4843) | −1.51 (0.0002) | −1.52 (0.0002) | −1.06 (0.3098) | −1.22 (0.0600) | −1.84 (<0.0001) |
| Week 4 DAS28(CRP) mean CFB (LOCF) (p-value vs placebo) | −0.97 | −1.28 (0.1236) | −1.89 (<0.0001) | −1.92 (<0.0001) | −1.45 (0.0280) | −1.63 (0.0018) | −2.24 (<0.0001) |
| Week 8 DAS28(CRP) mean CFB (LOCF) (p-value vs placebo) | −1.15 | −1.66 (0.0131) | −2.13 (<0.0001) | −2.31 (<0.0001) | −1.82 (0.0018) | −1.93 (0.0003) | −2.72 (<0.0001) |
| Week 12 DAS28(CRP) mean CFB (LOCF) (p-value vs placebo) | −1.19 | −1.75 (0.0092) | −2.23 (<0.0001) | −2.47 (<0.0001) | −1.88 (<0.0001) | −2.10 (<0.0001) | −2.84 (<0.0001) |
| Week 16 DAS28(CRP) mean CFB (LOCF) (p-value vs placebo) | −1.35 | −1.91 (0.0117) | −2.51 (<0.0001) | −2.70 (<0.0001) | −2.02 (<0.0001) | −2.37 (<0.0001) | −3.06 (<0.0001) |
| Week 20 DAS28(CRP) mean CFB (LOCF) (p-value vs placebo) | −1.26 | −1.99 (0.0009) | −2.65 (<0.0001) | −2.86 (<0.0001) | −2.07 (<0.0001) | −2.40 (<0.0001) | −3.02 (<0.0001) |
| Week 24 DAS28(CRP) mean CFB (LOCF) (p-value vs placebo) | −1.18 | −1.98 (0.0004) | −2.70 (<0.0001) | −2.80 (<0.0001) | −2.19 (<0.0001) | −2.40 (<0.0001) | −3.23 (<0.0001) |
| % patients reaching low disease activity at week 24 (LOCF) | 9 | 12 | 14 | 26 | 16 | 14 | 24 |
| % patients reaching remission at week 24 (LOCF) | 9 | 21 | 36 | 26 | 23 | 24 | 40 |
| % patients reaching low disease activity and/or remission at week 24 (LOCF) | 18 | 33 | 50 | 52 | 49 | 38 | 64 |

3.2.1.1.1 Study 2

The DAS28(CRP) variation after 12 weeks and 24 weeks treatment is presented in Table CII and below

TABLE CII

Study 2 DAS28 variation over 12 weeks

| | Placebo (N = 72) | 50 mg q.d. (N = 72) | 100 mg q.d. (N = 70) | 200 mg q.d. (N = 69) |
|---|---|---|---|---|
| Week 1 | | | | |
| DAS28(CRP) mean CFB (LOCF) (p-value vs placebo) | −0.51 | −0.70 (0.0992) | −0.88 (0.0269) | −1.15 (<0.0001) |
| Week 2 | | | | |
| DAS28(CRP) mean CFB (LOCF) (p-value vs placebo) | −0.74 | −0.97 (0.0925) | −1.04 (0.0925) | −1.54 (<0.0001) |
| Week 4 | | | | |
| DAS28(CRP) mean CFB (LOCF) (p-value vs placebo) | −0.84 | −1.37 (0.0021) | −1.50 (0.0010) | −1.87 (<0.0001) |
| Week 8 | | | | |
| DAS28(CRP) mean CFB (LOCF) (p-value vs placebo) | −0.94 | −1.65 (0.0001) | −1.91 (<0.0001) | −2.24 (<0.0001) |
| Week 12 | | | | |
| DAS28(CRP) mean CFB (LOCF) (p-value vs placebo) | −0.99 | −1.69 (0.0006) | −2.04 (<0.0001) | −2.33 (<0.0001) |
| % patients reaching low disease activity at week 12 (LOCF) | 7% | 13% | 13% | 28% |

TABLE CII-continued

Study 2 DAS28 variation over 12 weeks

|  | Placebo (N = 72) | 50 mg q.d. (N = 72) | 100 mg q.d. (N = 70) | 200 mg q.d. (N = 69) |
|---|---|---|---|---|
| % patients reaching remission at week 12 (LOCF) | 7% | 11% | 14% | 17% |
| % patients reaching low disease activity and/or remission at week 12 (LOCF) | 14% | 24% | 28% | 45% |

TABLE CIII

Study 2 DAS28 variation over 24 weeks

|  | Placebo (N = 72) | 50 mg q.d. (N = 72) | 100 mg q.d. (N = 70) | 200 mg q.d. (N = 69) |
|---|---|---|---|---|
| Week 1 |  |  |  |  |
| DAS28(CRP) mean CFB (LOCF) (p-value vs placebo) | −0.51 | −0.75 (0.0585) | −0.87 (0.0247) | −1.16 (<0.0001) |
| Week 2 |  |  |  |  |
| DAS28(CRP) mean CFB (LOCF) (p-value vs placebo) | −0.74 | −1.03 (0.0608) | −1.04 (0.0608) | −1.55 (<0.0001) |
| Week 4 |  |  |  |  |
| DAS28(CRP) mean CFB (LOCF) (p-value vs placebo) | −0.84 | −1.43 (0.0012) | −1.48 (0.0012) | −1.87 (<0.0001) |
| Week 8 |  |  |  |  |
| DAS28(CRP) mean CFB (LOCF) (p-value vs placebo) | −0.94 | −1.71 (<0.0001) | −1.89 (<0.0001) | −2.23 (<0.0001) |
| Week 12 |  |  |  |  |
| DAS28(CRP) mean CFB (LOCF) (p-value vs placebo) | −0.99 | −1.75 (0.0002) | −2.04 (<0.0001) | −2.32 (<0.0001) |
| Week 16 |  |  |  |  |
| DAS28(CRP) mean CFB (LOCF) Week 20 | — | −1.88 | −2.39 | −2.53 |
| DAS28(CRP) mean CFB (LOCF) Week 24 | — | −1.83 | −2.48 | −2.55 |
| DAS28(CRP) mean CFB (LOCF) | — | −1.95 | −2.61 | −2.62 |
| % patients reaching low disease activity at week 24 (LOCF) | — | 17 | 29 | 19 |
| % patients reaching remission at week 24 (LOCF) | — | 19% | 21% | 28% |
| % patients reaching low disease activity and/or remission at week 24 (LOCF) | — | 36% | 50% | 46% |

3.3. CRP Analysis

3.3.1.1. Principle of the Assay

[CRP] determination is available at Quest Diagnostics, Clinical Trials, Quest House, 125-135 Staines Road, Hounslow, Middlesex, TW3 3JB, United Kingdom under Catalogue n#86140.

The determination of CRP is made using Immunoturbidimetric assay for the in vitro quantitative determination of CRP in human serum and plasma on Roche/Hitachi cobas c systems, wherein human CRP agglutinates with latex particles coated with monoclonal anti-CRP antibodies. The aggregates are determined turbidimetrically (Eda et al., 1998; Price et al., 1987).

3.3.1.2. Assay

Human serum and plasma samples [CRP] determination was done on a Roche/Hitachi Cobas c 301 c 501/502 system which automatically calculate the analyte concentration of each sample. Samples containing precipitates are centrifuged before performing the assay.

The machine parameters are listed in Table CIV and Table CV below. The results using either LOCF are shown in below. The Hommel-corrected p-value for the pairwise comparisons of each group with placebo is shown.

The number of subjects (N) provided in each groups corresponds to the number of patients starting the study in each group, and the ACR data reported below corresponds to the responding patients continuing for the entire 24 weeks on their initial treatment course.

TABLE CIV

Cobas c 311 test parameters for [CRP] determination

| Assay type | 2 Point End |
|---|---|
| Reaction time/Assay points | 10/18-38 |
| Wavelength (sub/main) | 800/570 nm |
| Reaction direction | Increase |
| Units | mg/L (nmol/L, mg/dL) |
| Reagent pipetting | Diluent ($H_2O$) |
| Tris(hydroxymethyl)-aminomethane (TRIS) buffer with bovine serum albumin; preservatives | 150 μL |
| Latex particles coated with anti-CRP (mouse) in glycine buffer; immunoglobulins (mouse); preservative | 48 μL + $H_2O$ (24 μL) |
| Sample volumes | Sample dilution | Diluent (NaCl) |
| Normal (2 μL) | — | — |
| Decreased (4 μL) | 25 μL | 75 μL |
| Increased (4 μL) | — | — |

TABLE CV

Cobas c 501/502 test parameters for CRP determination

| Assay type | 2 Point End |
|---|---|
| Reaction time/Assay points | 10/13-29 |
| Wavelength (sub/main) | 800/570 nm |
| Reaction direction | Increase |
| Units | mg/L (nmol/L, mg/dL) |
| Reagent pipetting | Diluent ($H_2O$) |
| Tris(hydroxymethyl)-aminomethane (TRIS) buffer with bovine serum albumin; preservatives | 150 μL |
| Latex particles coated with anti-CRP (mouse) in glycine buffer; immunoglobulins (mouse); preservative | 48 μL + $H_2O$ (24 μL) |
| Sample volumes | Sample dilution | Diluent (NaCl) |
| Normal (2 μL) | — | — |
| Decreased (4 μL) | 25 μL | 75 μL |
| Increased (4 μL) | — | — |

3.3.1.1. Results 3.3.1.1.1 Study 1

The CRP variation after treatment is presented in Table CVI below

TABLE CVI

Study 1 - CRP variation

| | | q.d. groups | | | b.i.d. groups | | |
|---|---|---|---|---|---|---|---|
| | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| Week 1 CRP mean CFB mg/L (LOCF) (p-value vs placebo) | 1.78 | −7.95 (0.1495) | −11.02 (0.0035) | −17.06 (<0.0001) | −8.47 (0.0980) | −10.08 (0.0099) | −17.39 (<0.0001) |
| Week 2 CRP mean CFB mg/L (LOCF) (p-value vs placebo) | 1.57 | −8.23 (0.2029) | −12.94 (<0.0001) | −17.51 (<0.0001) | −10.06 (0.0133) | −11.03 (0.0009) | −19.69 (<0.0001) |
| Week 4 CRP mean CFB mg/L (LOCF) (p-value vs placebo) | 2.26 | −10.18 (0.0932) | −13.18 (0.0001) | −17.94 (<0.0001) | −7.72 (0.1478) | −13.28 (0.0001) | −20.64 (<0.0001) |
| Week 8 CRP mean CFB mg/L (LOCF) (p-value vs placebo) | 1.47 | −12.02 (0.0433) | −12.48 (0.0052) | −17.22 (0.0001) | −10.94 (0.0433) | −13.25 (0.0029) | −21.32 (<0.0001) |
| Week 12 CRP mean CFB mg/L (LOCF) (p-value vs placebo) | 2.67 | −13.15 (0.0103) | −13.57 (0.0005) | −17.24 (<0.0001) | −10.26 (0.0273) | −12.97 (0.0010) | −20.54 (<0.0001) |

TABLE I

Study 1 - CRP values - 24 weeks results

| | | q.d. groups | | | b.i.d. groups | | |
|---|---|---|---|---|---|---|---|
| | Placebo (N = 86) | 50 mg (N = 82) | 100 mg (N = 85) | 200 mg (N = 86) | 2 × 25 mg (N = 86) | 2 × 50 mg (N = 85) | 2 × 100 mg (N = 84) |
| Week 1 CRP mean CFB mg/L (LOCF) (p-value vs placebo) | 1.78 | −7.95 (0.1495) | −11.02 (0.0035) | −17.06 (<0.0001) | −8.47 (0.0980) | −10.08 (0.0099) | −17.39 (<0.0001) |
| Week 2 CRP mean CFB mg/L (LOCF) (p-value vs placebo) | 1.57 | −8.23 (0.2029) | −12.94 (<0.0001) | −17.51 (<0.0001) | −10.06 (0.0133) | −11.03 (0.0009) | −19.69 (<0.0001) |
| Week 4 CRP mean CFB mg/L (LOCF) (p-value vs placebo) | 2.26 | −10.18 (0.0932) | −13.18 (0.0001) | −17.94 (<0.0001) | −7.72 (0.1478) | −13.28 (0.0001) | −20.64 (<0.0001) |
| Week 8 CRP mean CFB mg/L (LOCF) (p-value vs placebo) | 1.47 | −12.02 (0.0433) | −12.48 (0.0052) | −17.22 (0.0001) | −10.94 (0.0433) | −13.25 (0.0029) | −21.32 (<0.0001) |
| Week 12 CRP mean CFB mg/L (LOCF) (p-value vs placebo) | 2.67 | −13.15 (0.0103) | −13.57 (0.0005) | −17.24 (<0.0001) | −10.26 (0.0273) | −12.97 (0.0010) | −20.54 (<0.0001) |
| Week 16 CRP mean CFB mg/L (LOCF) (p-value vs placebo) | 1.39 | −13.55 (0.0046) | −11.66 (0.0044) | −20.38 (<0.0001) | −12.55 (0.0046) | −12.57 (0.0025) | −21.34 (<0.0001 |
| Week 20 CRP mean CFB mg/L (LOCF) (p-value vs placebo) | 1.63 | −13.12 (0.0094) | −14.50 (<0.0001) | −17.89 (<0.0001) | −12.20 (0.0094) | −13.16 (0.0007) | −20.80 (<0.0001) |
| Week 24 CRP mean CFB mg/L (LOCF) (p-value vs placebo) | 2.00 | −15.22 (0.0094) | −14.89 (0.0008) | −15.57 (0.0039) | −11.68 (0.0280) | −11.96 (0.0142) | −20.82 (<0.0001) |

3.3.1.1.2 Study 2

The CRP variation after treatment is presented in the table below

TABLE II

Study 2 - CRP values

| | Placebo (N = 72) | 50 mg q.d. (N = 72) | 100 mg q.d. (N = 70) | 200 mg q.d. (N = 69) |
|---|---|---|---|---|
| Week 1 | | | | |
| CRP mean CFB mg/L (LOCF) (p-value vs placebo) | −5.65 | −3.70 (0.3187) | −10.33 (0.0286) | −12.58 (0.0020) |
| Week 2 | | | | |
| CRP mean CFB mg/L (LOCF) (p-value vs placebo) | −1.57 | −4.16 (0.0613) | −8.67 (0.0146) | −13.28 (0.0002) |
| Week 4 | | | | |
| CRP mean CFB mg/L (LOCF) (p-value vs placebo) | −1.68 | −9.46 (<0.0001) | −12.08 (<0.0001) | −13.04 (<0.0001) |
| Week 8 | | | | |
| CRP mean CFB mg/L (LOCF) (p-value vs placebo) | −3.66 | −11.16 (<0.0001) | −14.17 (<0.0001) | −13.86 (<0.0001) |
| Week 12 | | | | |
| CRP mean CFB mg/L (LOCF) (p-value vs placebo) | −8.71 | −4.43 (0.4200) | −12.25 (0.0338) | −14.85 (0.0021) |

3.3.2. Dyslipidemia Associated Biomarkers

3.3.2.1. Cholesteryl Ester Transfer Protein (CETP)

Plasma CETP concentration was determined using a commercial available ELISA kit from Alpco (26-G Keewaydin Drive, Salem, N.H. 03079 USA) according to manufacturer's instruction. Catalogue number 47-CETH-E01, lot number used: 812RCL.

Plasma endogenous CETP activity was determined by a fluorescent method using donor liposomes enriched with nitrobenzoxadiazole-labeled cholesteryl esters (NBD-CE) from Roar Biomedical (Roar Biomedical, Inc., Audubon Biomedical Center, 3960 Broadway, New York, N.Y. 10032 USA). In short, incubation media contained 4 μL of donor liposomes and 10 μL plasma in a final volume of 200 μl PBS. Incubations were performed for 3 h at 37° C. in a microplate Fluorescence Reader. The CETP-mediated transfer of nitrobenzoxadiazole-labeled cholesteryl esters from self-quenched donors to acceptor endogenous plasma lipoproteins was monitored by the increase in fluorescence intensity (excitation, 465 nm; emission, 535 nm). The amounts of NBD-CE transferred (in pmol) were calculated by using a standard curve, which plotted fluorescence intensity and the concentration of NBD-CEs dispersed in propan-2-ol. Results were expressed as the initial transfer rate of NBD-CEs after deduction of blank values. CETP activity was calculated as pmol cholesteryl ester transfer/μL plasma/h. Catalogue number RB-CETP, Lot number used 10117067.

TABLE III

Study 4 CETP level variation

| | Placebo | 30 mg q.d. | 75 mg q.d. | 150 mg q.d. | 300 mg q.d. |
|---|---|---|---|---|---|
| Baseline (ng/mL) | 3.0 | 3.2 | 2.8 | 2.8 | 2.5 |
| week 4 (ng/mL) | 3.1 | 3.2 | 2.7 | 2.3 | 2.2 |
| 4 weeks CFB (%) | 4.4 | 2.4 | −2.8 | −11.4 | −10.2 |
| t-test | 0.5 | 0.6 | 0.4 | <0.05 | <0.005 |

3.3.2.2. Proprotein Convertase Subtilisin/Kexin Type-9 (PCSK9)

Plasma PCSK9 concentration was determined using a commercial available ELISA kit from R&D systems (614 McKinley Place NE, Minneapolis, Minn. 55413, USA) according to manufacturer's instruction. Catalogue number DPC900, lot number used: 321050.

TABLE IV

Study 4 - PCSK9 level variation

| | Placebo | 30 mg q.d. | 75 mg q.d. | 150 mg q.d. | 300 mg q.d. |
|---|---|---|---|---|---|
| Baseline (ng/mL) | 293 | 282.1 | 277.0 | 264.4 | 261.7 |
| week 4 (ng/mL) | 346 | 296.9 | 292.4 | 294.6 | 291.2 |
| 4 weeks CFB (%) | 15.1% | 6.8% | 11.4% | 11.6% | 10.4% |
| t-test | 0.0008 | 0.4 | 0.04 | 0.2 | 0.046 |

3.3.2.3. Apolipoproteins (ApoA-I, ApoB, ApoC-II and ApoC-III)

ApoAI, and ApoB were measured on the Selectra autoanalyzer (Sopachem BV, 44-RI Straat 33, 4051 AP Ochten, The Netherlands). All assays were commercially available from DiaSys Diagnostic Systems GmbH, Alte Strasse 9, 65558 Holzheim, Germany.

Plasma ApoC-II and ApoC-III concentrations are determined using commercial available ELISA kits from Abnova (9th Floor, No. 108, Jhouzih St., Neihu District. Taipei City, 114, Taiwan) according to manufacturer's instruction. apoC2: catalogue number KA0464, lot number used: 08871403. apoC3: catalogue number KA0465, lot number used: 02961525.

TABLE V

Study 4 - ApoA-I level variation

| | Placebo | 30 mg q.d. | 75 mg q.d. | 150 mg q.d. | 300 mg q.d. |
|---|---|---|---|---|---|
| Baseline (ng/mL) | 137.8 | 148.3 | 141.8 | 139.9 | 142.6 |
| week 4 (ng/mL) | 154.1 | 154.9 | 155.6 | 147.4 | 179.2 |
| 4 weeks CFB (%) | 14.3% | 5.2% | 9.8% | 5.5% | 27.9% |
| t-test | 0.06 | 0.2 | 0.008 | 0.2 | <0.0001 |

TABLE VI

Study 4 - ApoB level variation

| | Placebo | 30 mg q.d. | 75 mg q.d. | 150 mg q.d. | 300 mg q.d. |
|---|---|---|---|---|---|
| Baseline (ng/mL) | 79.3 | 98.8 | 98.5 | 93.8 | 89.4 |
| week 4 (ng/mL) | 88.6 | 110.8 | 94.7 | 90.7 | 95.6 |

TABLE VI-continued

Study 4 - ApoB level variation

|  | Placebo | 30 mg q.d. | 75 mg q.d. | 150 mg q.d. | 300 mg q.d. |
|---|---|---|---|---|---|
| 4 weeks CFB (%) | 12.6% | 19.5% | −1.1% | −1.8% | 6.8% |
| t-test | 0.13 | 0.3 | 0.8 | 0.8 | 0.06 |

TABLE VII

Study 4 - ApoC-II level variation

|  | Placebo | 30 mg q.d. | 75 mg q.d. | 150 mg q.d. | 300 mg q.d. |
|---|---|---|---|---|---|
| Baseline (ng/mL) | 57.3 | 96.3 | 64.7 | 77.1 | 80.5 |
| week 4 (ng/mL) | 80.6 | 98.4 | 87.7 | 67.4 | 87.0 |
| 4 weeks CFB (%) | 128.2% | 11.2% | 23.3% | 8.6% | 37.0% |
| t-test | 0.1 | 0.4 | 0.1 | 0.5 | 0.016 |

TABLE VIII

Study 4 - ApoC-III level variation

|  | Placebo | 30 mg q.d. | 75 mg q.d. | 150 mg q.d. | 300 mg q.d. |
|---|---|---|---|---|---|
| Baseline (ng/mL) | 60.3 | 80.3 | 68.4 | 89.7 | 80.0 |
| week 4 (ng/mL) | 74.3 | 78.6 | 79.6 | 82.7 | 88.2 |
| 4 weeks CFB (%) | 85.2 | 4.6 | 17.6 | 9.6 | 27.9 |
| t-test | 0.13 | 0.6 | 0.015 | 0.5 | 0.019 |

3.3.2.4. Plasma Cholesterol, [HDL] Cholesterol and Triglycerides

Triglycerides, [HDL] cholesterol, and plasma cholesterol were measured on the Selectra autoanalyzer (Sopachem BV, 44-RI Straat 33, 4051 AP Ochten, The Netherlands). All assays were commercially available from DiaSys Diagnostic Systems GmbH, Alte Strasse 9, 65558 Holzheim, Germany.

Plasma free cholesterol are analysed using a commercial available assay from Instruchemie (Zwet 26, 9932 AB Delfzijl, Netherlands).

TABLE IX

Study 4 - Triglycerides level variation

|  | Placebo | 30 mg q.d. | 75 mg q.d. | 150 mg q.d. | 300 mg q.d. |
|---|---|---|---|---|---|
| Baseline (ng/mL) | 1.0 | 1.2 | 1.0 | 1.4 | 1.3 |
| week 4 (ng/mL) | 1.3 | 1.7 | 1.1 | 2.1 | 1.4 |
| 4 weeks CFB (%) | 39.3 | 51.7 | 6.6 | 93.6 | 23.3 |
| t-test | 0.1 | 0.2 | 0.4 | 0.048 | 0.22 |

TABLE X

Study 4 - Total cholesterol level variation

|  | Placebo | 30 mg q.d. | 75 mg q.d. | 150 mg q.d. | 300 mg q.d. |
|---|---|---|---|---|---|
| Baseline (ng/mL) | 4.4 | 4.9 | 4.9 | 5.0 | 4.7 |
| week 4 (ng/mL) | 4.8 | 5.8 | 5.1 | 5.0 | 5.7 |
| 4 weeks CFB (%) | 9.8% | 25.9% | 5.2% | −1.2% | 19.4% |
| t-test | 0.2 | 0.11 | 0.3 | 0.8 | 0.0001 |

TABLE XI

Study 4 - HDL level variation

|  | Placebo | 30 mg q.d. | 75 mg q.d. | 150 mg q.d. | 300 mg q.d. |
|---|---|---|---|---|---|
| Baseline (ng/mL) | 0.9 | 0.9 | 1.0 | 1.0 | 1.0 |
| week 4 (ng/mL) | 1.0 | 1.0 | 1.1 | 1.1 | 1.4 |
| 4 weeks CFB (%) | 16.2% | 6.7% | 13.7% | 10.7% | 46.0% |
| t-test | 0.1 | 0.22 | 0.0005 | 0.035 | 0.0001 |

3.3.2.5. Plasma Serum Amyloid A (SAA)

Plasma SAA concentration was determined using a commercial available Novex ELISA kit from Life technologies (Bleiswijk, The Netherlands) according to manufacturer's instruction. Catalogue number KHA0011, lot number used: 1433688A.

TABLE XII

Study 4 - SAA level variation

|  | Placebo | 30 mg q.d. | 75 mg q.d. | 150 mg q.d. | 300 mg q.d. |
|---|---|---|---|---|---|
| Baseline (ng/mL) | 801.5 | 935.4 | 883.7 | 621.3 | 555.6 |
| week 4 (ng/mL) | 453.1 | 436.2 | 201.3 | 388.5 | 43.2 |
| 4 weeks CFB (%) | −12.3% | −15.4% | −13.5% | −56.7% | −62.0% |
| t-test | 0.4 | 0.3 | 0.5 | <0.005 | <0.005 |

3.3.2.6. Plasma Lecithin-Cholesterol Acyltransferase (LCAT)

LCAT activity was determined using a commercial available assay from Roar Biomedical. In short; incubation media contained 0.5 μL substrate reagent, 4 μL plasma in a final volume of 100 μL assay buffer. Incubations were performed for 1 h at 37° C. in a microtiter plate. Hereafter 200 μL READ reagent was added to the wells and after mixing, 200 μL was transferred to a black fluorescence compatible microplate. The plate was read at 340 nm excitation, 390 nm and 450 nm emission. LCAT activity was expressed as a ratio of the emission at 390 nm and 450 nm. These two wavelengths represent the LCAT substrate hydrolysed and not hydrolysed. An increase in the ratio indicates increased LCAT activity. Catalogue number RB-LCAT, Lot number used 13581392.

TABLE XIII

Study 4 - LCAT level variation

|  | Placebo | 30 mg q.d. | 75 mg q.d. | 150 mg q.d. | 300 mg q.d. |
|---|---|---|---|---|---|
| Baseline (ng/mL) | 1.9 | 1.9 | 2.0 | 1.9 | 2.0 |
| week 4 (ng/mL) | 2.0 | 2.0 | 2.1 | 1.9 | 2.1 |
| 4 weeks CFB (%) | 2.4 | 0.4 | 4.2 | 2.9 | 4.4 |
| t-test | 0.1 | 0.8 | 0.0003 | 0.011 | 0.007 |

3.3.2.7. Lipoprotein A (Lp(a))

Lipoprotein A (Lp(a)) were measured on the Selectra autoanalyzer (Sopachem BV, 44-RI Straat 33, 4051 AP Ochten, The Netherlands). All assays were commercially available from DiaSys Diagnostic Systems GmbH, Alte Strasse 9, 65558 Holzheim, Germany.

TABLE XIV

Study 4 - LpA level variation

|  | Placebo | 30 mg q.d. | 75 mg q.d. | 150 mg q.d. | 300 mg q.d. |
|---|---|---|---|---|---|
| Baseline (ng/mL) | 20.3 | 22.5 | 28.5 | 29.5 | 13.4 |
| week 4 (ng/mL) | 28.4 | 25.9 | 23.6 | 35.0 | 10.1 |
| 4 weeks CFB (%) | 9.1 | 3.9 | −3.7 | 7.0 | 4.4 |
| t-test | 0.5 | 0.5 | 0.7 | 0.3 | 0.7 |

3.3.2.8. Paraoxonase Assay (PON)

Paraoxanases are involved, in particular PON1 have a role in preventing atherosclerosis.

The PON assay is performed according to published protocol by Mackness et al. (Mackness et al., 2003).

TABLE XV

Study 4 - PON1 level variation

|  | Placebo | 30 mg q.d. | 75 mg q.d. | 150 mg q.d. | 300 mg q.d. |
|---|---|---|---|---|---|
| Baseline (ng/mL) | 47.7 | 39.1 | 69.3 | 52.5 | 59.8 |
| week 4 (ng/mL) | 49.0 | 40.6 | 73.7 | 70.6 | 77.5 |
| 4 weeks CFB (%) | 3.3% | 4.2% | 11.2% | 43.4% | 31.0% |
| t-test | 0.7 | 0.2 | 0.004 | 0.066 | <0.0001 |

3.4. Crohn's Disease Activity Index (CDAI) %

The Crohn's disease activity index (CDAI) is a numerical calculation derived from the sum of products from a list of 8 items (see Table XVI below), and multiplied by weighting factors for each item to define the severity of "disease activity" in patients with Crohn's disease $(CD)_{[1]}$. Essentially, the CDAI represents a numerical estimation of a physician's interpretation of patient symptoms. Index values of 150 and below are associated with quiescent or non-active disease (i.e. "remission"). Values over 150 are indicative of active disease, and over 450, extremely severe disease. %

In the present study, clinical remission is defined as a CDAI score of <150 points, and a clinical response is defined as a decrease in CDAI score of at least 100 points.

TABLE XVI.

CDAI calculation components

| Category | Count | Factor |
|---|---|---|
| Number of liquid or very soft stools | 7-day total number of liquid or very soft stools (reported on the 7 days immediately prior to the study visit) | x2 |
| Abdominal pain | 7-day total of daily abdominal pain scores on a 3-point scale:<br>0 = none,<br>1 = mild,<br>2 = moderate,<br>3 = severe,<br>(reported on the 7 days immediately prior to the study visit) | x5 |
| General well being. | 7-day total of daily general well-being scores on a 4-point scale:<br>0 = well, 1 = slightly below par, 2 = poor, 3 = very poor, 4 = terrible<br>(reported on the 7 days immediately prior to the study visit) | x7 |
| Extra-intestinal manifestations of Crohn's Disease | Total number of checked boxes (check all that apply):<br>Arthritis/arthralgia<br>Iritis/uveitis<br>Erythema nodosum/pyoderma gangrenosum/aphthous stomatitis<br>Anal fissure, fistula, or abscess<br>Other fistula<br>Fever over 37.8° C. during past week | x20 |
| Lomotil/Imodium/opiates for diarrhea | Yes = 1<br>No = 0 | x30 |
| Abdominal mass | None = 0<br>Questionable = 2<br>Definite = 5 | x10 |
| Hematocrit (%) | Males: subtract value from 47<br>Females: subtract value from 42 | x6 |
| Body Weight | $\dfrac{\text{(Standard weight (kg)} - \text{Actual bodyweight (kg))}}{\text{Standard bodyweight (kg)}}$ | |

3.5. Endoscopic Scores for Crohn's Disease

For the evaluation of disease severity the Crohn's Disease Index of Severity (CDEIS), and the Simple Endoscopic Score for Crohn's Disease (SES-CD) may be used. These are validated scores for the measurement of endoscopic findings. (Sipponen et al, 2010)

3.5.1. CDEIS

For the grading of endoscopic findings, the bowel is divided into five segments: the terminal ileum, the right, transverse, left colon, and rectum. The ileum is scored for the full examined extent. The right colonic segment included the cecum, the ileocecal valve, and the ascending colon to the hepatic flexure. The bowel segment between hepatic and splenic flexures was the transverse colon. The left colon included both the descending colon and the sigmoid. The rectum was the segment distal to the rectosigmoid junction. For the CDEIS, as originally defined, presence of mucosal superficial ulcers, presence of deep ulcers, the extent of surface involved by disease, the extent of ulcerated surface, and the presence of ulcerated or nonulcerated stenosis are recorded in each segment.$_7$ The CDEIS score can range from 0-44, with a higher score indicating more severe disease. A CDEIS below 3 is classified as inactive, 3-9 is mildly active, 9-12 is moderately active, and >12 is severely active disease.

3.5.2. SES-CD

For the SES-CD, four endoscopic variables in the five segments are scored from 0-3: Variable "presence and size of ulcers" is scored 0 when no ulcers are present, small ulcers (diameter 0.1-0.5 cm) are scored 1, medium-sized ulcers (diameter 0.5-2 cm) 2, and large ulcers (>2 cm) 3. Variable "extent of ulcerated surface" is scored 0 when no ulcers were present, 1 when extent was <10%, 2 when extent is 10%-30%, and 3 when it is >30%. The variable extent of affected surface is scored 0 if none, 1 when <50%, 2 when 50%-75%, and 3 when >75%. The presence and type of narrowings is scored 0 when no narrowings are present, a single passable narrowing is scored 1, multiple passable narrowings are scored 2, and a nonpassable narrowing is scored 3. SES-CD between 0 and 2 suggested inactive disease, 3-6 is mildly active disease, 7-15 is moderately active disease, and >16 is severely active disease.

TABLE XVII

Study 5-10 weeks SES-CD scores (LOCF)

|  | Placebo (N = 44) | 200 mg (N = 128) | p-values |
|---|---|---|---|
| SES-CD mean, baseline | 15.9 | 14.2 | — |
| SES-CD mean, W 10 | 13.2 | 11.6 | — |
| SES-CD mean CFB, W 10 | −2.8 | −2.6 | 0.8725 |

TABLE XVIII

Study 5-10 weeks SES-CD derived responses (LOCF)

|  | Placebo (N = 44) | 200 mg (N = 128) | p-values |
|---|---|---|---|
| Endoscopic response (SES-CD % improvement ≥ 50) | 18% | 25% | 0.4056 |
| Endoscopic remission (SES-CD % improvement ≤ 4, ulcerated subscore ≤ 1 in all 5 segments) | 8% | 14% | 0.3721 |
| Mucosal healing (SES-CD % = 0) | 2% | 2% | 0.9685 |
| Deep remission (CDAI score < 150 points, SES-CD score ≤ 4, ulcerated subscore ≤ 1 in all 5 segments) | 5% | 8% | 0.6003 |

TABLE XIX

Study 5-10 weeks SES-CD derived responses (LOCF) by prior TNF therapy

|  | Anti-TNF Naïve | | Anti-TNF experienced non-responders | |
|---|---|---|---|---|
|  | Placebo (N = 16) | 200 mg (N = 57) | Placebo (N = 28) | 200 mg (N = 71) |
| Endoscopic response (SES-CD % improvement ≥ 50) | 25% | 28% | 14% | 23% |
| Endoscopic remission (SES-CD % improvement ≤ 4, ulcerated subscore ≤ 1 in all 5 segments) | 8% | 16% | 8% | 12% |
| Mucosal healing (SES-CD % = 0) | 0% | 0% | 4% | 1% |
| Deep remission (CDAI score < 150 points, SES-CD score ≤ 4, ulcerated subscore ≤ 1 in all 5 segments) | 0% | 0% | 8% | 6% |

TABLE XX

Study 5-10 weeks SES-CD derived responses (LOCF) by screening CRP Level

|  | CRP ≤ 10 ml/L | | CRP ≥ 10 mg/L | |
| --- | --- | --- | --- | --- |
|  | Placebo (N = 25) | 200 mg (N = 74) | Placebo (N = 19) | 200 mg (N = 54) |
| Endoscopic response (SES-CD % improvement ≥ 50) | 20% | 23% | 16% | 28% |
| Endoscopic remission (SES-CD % improvement ≤ 4, ulcerated subscore ≤ 1 in all 5 segments) | 14% | 16% | 0% | 0% |
| Mucosal healing (SES-CD % = 0) | 4% | 3% | 0% | 0% |
| Deep remission (CDAI score < 150 points, SES-CD score ≤ 4, ulcerated subscore ≤ 1 in all 5 segments) | 9% | 10% | 0% | 0% |

TABLE XXI

Study 5-10 weeks SES-CD derived responses (LOCF) by baseline corticosteroid use

|  | With steroids | | Without steroids | |
| --- | --- | --- | --- | --- |
|  | Placebo (N = 23) | 200 mg (N = 63) | Placebo (N = 21) | 200 mg (N = 65) |
| Endoscopic response (SES-CD % improvement ≥ 50) | 13% | 22% | 24% | 28% |
| Endoscopic remission (SES-CD % improvement ≤ 4, ulcerated subscore ≤ 1 in all 5 segments) | 5% | 12% | 11% | 15% |
| Mucosal healing (SES-CD % = 0) | 0% | 0% | 5% | 5% |
| Deep remission (CDAI score < 150 points, SES-CD score ≤ 4, ulcerated subscore ≤ 1 in all 5 segments) | 0% | 0% | 11% | 5% |

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Aletaha, D., Neogi, T., Silman, A. J., Funovits, J., Felson, D. T., Bingham, C. O., Birnbaum, N. S., Burmester, G. R., Bykerk, V. P., Cohen, M. D., Combe, B., Costenbader, K. H., Dougados, M., Emery, P., Ferraccioli, G., Hazes, J. M. W., Hobbs, K., Huizinga, T. W. J., Kavanaugh, A., Kay, J., Kvien, T. K., Laing, T., Mease, P., Ménard, H. A., Moreland, L. W., Naden, R. L., Pincus, T., Smolen, J. S., Stanislawska-Biernat, E., Symmons, D., Tak, P. P., Upchurch, K. S., Vencovský, J., Wolfe, F., Hawker, G., 2010. 2010 Rheumatoid arthritis classification criteria: An American College of Rheumatology/European League Against Rheumatism collaborative initiative. Arthritis Rheum. 62, 2569-2581. doi:10.1002/art.27584

Allain, C. C., Poon, L. S., Chan, C. S. G., Richmond, W., Fu, P. C., 1974. Enzymatic Determination of Total Serum Cholesterol. Clin. Chem. 20, 470-475.

Barter, P., 2011. HDL-C: Role as a risk modifier. Atheroscler. Suppl. 12, 267-270. doi:10.1016/S1567-5688(11)70885-6

Chait, A., Han, C. Y., Oram, J. F., Heinecke, J. W., 2005. Thematic review series: The Immune System and Atherogenesis. Lipoprotein-associated inflammatory proteins: markers or mediators of cardiovascular disease? J. Lipid Res. 46, 389-403. doi:10.1194/jlr.R400017-JLR200

Chapman, M. J., 2006. Therapeutic elevation of HDL-cholesterol to prevent atherosclerosis and coronary heart disease. Pharmacol. Ther. 111, 893-908. doi:10.1016/j.pharmthera.2006.02.003

Charles-Schoeman, C., Fleischmann, R., Davignon, J., Schwartz, H., Turner, S. M., Beysen, C., Milad, M., Hellerstein, M. K., Luo, Z., Kaplan, I. V., Riese, R., Zuckerman, A., McInnes, I. B., 2015. Potential Mechanisms Leading to the Abnormal Lipid Profile in Patients With Rheumatoid Arthritis Versus Healthy Volunteers and Reversal by Tofacitinib. Arthritis Rheumatol. 67, 616-625. doi:10.1002/art.38974

Eda, S., Kaufmann, J, Roos, W., Pohl, S., 1998. Development of a new microparticle-enhanced turbidimetric assay for C-reactive protein with superior features in analytical sensitivity and dynamic range. J. Clin. Lab. Anal. 12, 137-144. doi:10.1002/(SICI)1098-2825(1998)12:3<137::AID-JCLA2>3.0. CO; 2-6

Fransen, J., Stucki, G., van Riel, P. L. C. M., 2003. Rheumatoid arthritis measures: Disease Activity Score (DAS), Disease Activity Score-28 (DAS28), Rapid Assessment of Disease Activity in Rheumatology (RADAR), and Rheumatoid Arthritis Disease Activity Index (RADAI). Arthritis Care Res. 49, S214-S224. doi:10.1002/art.11407

Friedewald, W. T., Levy, R. I., Fredrickson, D. S., 1972. Estimation of the Concentration of Low-Density Lipoprotein Cholesterol in Plasma, Without Use of the Preparative Ultracentrifuge. Clin. Chem. 18, 499-502.

Kumar, N., Armstrong, D. J., 2008. Cardiovascular disease—the silent killer in rheumatoid arthritis. Clin. Med. 8, 384-387. doi:10.7861/clinmedicine.8-4-384

Mackness, B., Durrington, P., McElduff, P., Yarnell, J., Azam, N., Watt, M., Mackness, M., 2003. Low Paraoxonase Activity Predicts Coronary Events in the Caerphilly Prospective Study. Circulation 107, 2775-2779. doi: 10.1161/01.CIR.0000070954.00271.13

Menet, C. J. M., Smits, K. K., 2010. 5-Phenyl-[1,2,4]triazolo[1,5-A]pyridin-2-Y1 Carboxamides as Jak Inhibitors. WO2010149769 (A1).

Millán, J., Pintó, X., Muñoz, A., Zúñiga, M., Rubiés-Prat, J., Pallardo, L. F., Masana, L., Mangas, A., Hernández-Mijares, A., González-Santos, P., Ascaso, J. F., Pedro-Botet, J., 2009. Lipoprotein ratios: Physiological significance and clinical usefulness in cardiovascular prevention. Vasc. Health Risk Manag. 5, 757-765.

Nam, B.-H., Kannel, W. B., D'Agostino, R. B., 2006. Search for an Optimal Atherogenic Lipid Risk Profile: From the Framingham Study. Am. J. Cardiol. 97, 372-375. doi: 10.1016/j.amjcard.2005.08.055

Navarro-Millán, I., Charles-Schoeman, C., Yang, S., Bathon, J. M., Bridges, S. L., Chen, L., Cofield, S. S., Dell'Italia, L. J., Moreland, L. W., O'Dell, J. R., Paulus, H. E., Curtis, J. R., 2013. Changes in Lipoproteins Associated With Methotrexate Therapy or Combination Therapy in Early Rheumatoid Arthritis: Results From the Treatment of Early Rheumatoid Arthritis Trial. Arthritis Rheum. 65, 1430-1438. doi:10.1002/art.37916

Nilsson, J., 2005. CRP—Marker or Maker of Cardiovascular Disease? Arterioscler. Thromb. Vasc. Biol. 25, 1527-1528. doi:10.1161/01.ATV.0000174796.81443.3f O'Shea, J. J., Laurence, A., McInnes, I. B., 2013. Back to the Future: Oral targeted therapy for RA and other autoimmune diseases. Nat. Rev. Rheumatol. 9, 173-182. doi: 10.1038/nrrheum.2013.7

O'Shea, J. J., Plenge, R., 2012. JAK and STAT Signaling Molecules in Immunoregulation and Immune-Mediated Disease. Immunity 36, 542-550. doi:10.1016/j.immuni.2012.03.014

Price, C. P., Trull, A. K., Berry, D., Gorman, E. G., 1987. Development and validation of a particle-enhanced turbidimetric immunoassay for C-reactive protein. J. Immunol Methods 99, 205-211. doi:10.1016/0022-1759(87)90129-3

Ridker, P. M., Rifai, N., Rose, L., Buring, J. E., Cook, N. R., 2002. Comparison of C-Reactive Protein and Low-Density Lipoprotein Cholesterol Levels in the Prediction of First Cardiovascular Events. N. Engl. J. Med. 347, 1557-1565. doi:10.1056/NEJMoa021993

Rifai, N., Warnick, G. R., McNamara, J. R., Belcher, J. D., Grinstead, G. F., Frantz, I. D., 1992. Measurement of low-density-lipoprotein cholesterol in serum: a status report. Clin. Chem. 38, 150-160.

Robertson, J., Peters, M. J., McInnes, I. B., Sattar, N., 2013. Changes in lipid levels with inflammation and therapy in RA: a maturing paradigm. Nat. Rev. Rheumatol. 9, 513-523. doi:10.1038/nrrheum.2013.91

Song, T.-J., Cho, H.-J., Chang, Y., Youn, M., Shin, M.-J., Jo, I., Heo, J. H., Kim, Y.-J., 2015. Low-Density-Lipoprotein Particle Size Predicts a Poor Outcome in Patients with Atherothrombotic Stroke. J. Clin. Neurol. Seoul Korea 11, 80-86. doi:10.3988/jcn.2015.11.1.80

The Merck Manual of Diagnosis and Therapy, 19th ed, 2011. MERCK SHARP & DOHME CORP., A SUBSIDIARY OF MERCK & CO., INC., Whitehouse Station, N.J., USA.

Van't Klooster, G., Brys, R. C. X., Van, R., Namour, F. S., 2013 Aminotriazolopyridine for Use in the Treatment of Inflammation, and Pharmaceutical Compositions Thereof WO2013189771 (A1).

Wells, G., Becker, J.-C., Teng, J., Dougados, M., Schiff, M., Smolen, J., Aletaha, D., van Riel, P. L. C. M., 2008. Validation of the 28-joint Disease Activity Score (DAS28) and European League Against Rheumatism response criteria based on C-reactive protein against disease progression in patients with rheumatoid arthritis, and comparison with the DAS28 based on erythrocyte sedimentation rate. Ann. Rheum. Dis. 68, 954-960. doi:10.1136/ard.2007.084459

Wuts, P. G. M., Greene, T. W., 2012. Greene's Protective Groups in Organic Synthesis, 4 edition. ed. Wiley-Interscience.

Sipponen, T., Nuutinen, H., Turunen, U., Färkkilä, M., 2010. Endoscopic evaluation of Crohn's disease activity: comparison of the CDEIS and the SES-CD. Inflamm Bowel Dis. 16, 2131-2136. doi:10.1002/ibd.21300

The invention claimed is:

1. A method for the prophylaxis and/or treatment of cardiovascular disorders and/or dyslipidemia, comprising:
    administering to a patient in need thereof an effective amount of a compound according to Formula I:

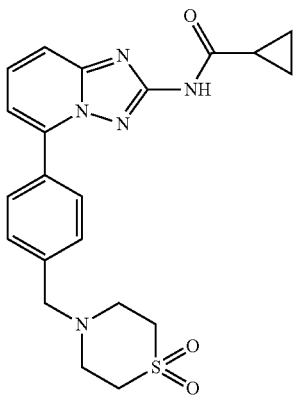

or a pharmaceutically acceptable salt thereof, or a solvate or the salt of a solvate thereof, or an active metabolite thereof.

2. The method of claim 1, wherein the salt of a solvate is a [Compound according to Formula I:HCl:3H₂O] adduct.

3. The method of claim 1, wherein the cardiovascular disorder is atherosclerosis.

4. The method of claim 1, wherein the compound or the pharmaceutically acceptable salt thereof is administered in combination with a further therapeutic agent.

5. A method for the prophylaxis and/or treatment of cardiovascular disorders and/or dyslipidemia, comprising:
administering to a patient in need thereof a pharmaceutical composition comprising at least one pharmaceutically acceptable carrier, excipient, or diluent and an effective amount of a compound according to Formula I:

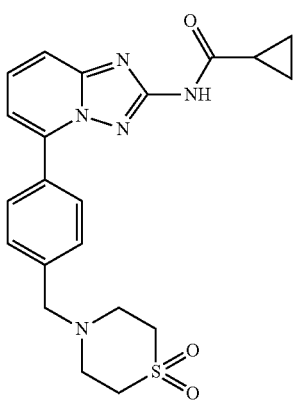

or a pharmaceutically acceptable salt thereof, and a pharmaceutically acceptable carrier, excipient, or diluent.

6. The method of claim 5, wherein the pharmaceutical composition comprises comprising a further therapeutic agent.

7. The method of claim 1, wherein the compound or the pharmaceutically acceptable salt thereof is administered to the patient, and wherein the patient is an individual presenting an abnormal lipid profile.

8. The method of claim 7, wherein the abnormal lipid profile is characterized by [LDL] below 50 mg/dL (or below 1.3 mmol/L) and [HDL] below 40 mg/dL (or below 1.04 mmol/L).

9. The method of claim 1, wherein the compound or the pharmaceutically acceptable salt thereof is administered to the patient, and wherein the patient is a clinical non RA-afflicted patient.

10. The method of claim 9, wherein the patient's condition is measured by a DAS28(CRP) score.

11. The method of claim 10, wherein the DAS28(CRP) score is less than 2.6.

12. The method of claim 10, wherein the patient has a CRP level greater than 3 mg/L.

13. The method of claim 1, wherein the patient is a clinical RA-afflicted patient and administration occurs at least once a week over a period of greater than 4 weeks.

14. The method of claim 1, wherein the patient is a clinical RA-afflicted patient and the patient's condition is measured by a DAS28(CRP) score.

15. The method of claim 14, wherein the DAS28(CRP) score is greater than 3.2.

16. The method of claim 1, wherein the compound or the pharmaceutically acceptable salt thereof is administered at a dose of 100 mg twice a day.

17. The method of claim 1, wherein the compound or the pharmaceutically acceptable salt thereof is administered at a dose of 200 mg once a day.

18. The method of claim 1, wherein the compound or the pharmaceutically acceptable salt thereof is administered at a dose from 25 mg to 400 mg.

19. The method of claim 4, wherein the further therapeutic agent is an agent for the prophylaxis and/or treatment of cardiovascular disease.

20. The method of claim 4, wherein the further therapeutic agent is an agent for the prophylaxis and/or treatment of atherosclerosis.

21. The method of claim 5, wherein the patient is an individual presenting an abnormal lipid profile.

22. The method of claim 21, wherein the abnormal lipid profile is characterized by [LDL] below 50 mg/dL (or below 1.3 mmol/L) and [HDL] below 40 mg/dL (or below 1.04 mmol/L).

23. The method of claim 5, wherein the patient is a clinical non RA-afflicted patient.

24. The method of claim 23, wherein the patient's condition is measured by a DAS28(CRP) score.

25. The method of claim 24, wherein the DAS28(CRP) score is less than 2.6.

26. The method of claim 24, wherein the patient has a CRP level greater than 3 mg/L.

27. The method of claim 5, wherein the patient is a clinical RA-afflicted patient, and wherein the pharmaceutical composition is administered at least once a week over a period of greater than 4 weeks.

28. The method of claim 5, wherein the patient is a clinical RA-afflicted patient, and the patient's condition is measured by a DAS28(CRP) score.

29. The method of claim 28, wherein the DAS28(CRP) score is greater than 3.2.

30. The method of claim 5, wherein the compound or the pharmaceutically acceptable salt thereof is administered at a dose of 100 mg twice a day.

31. The method of claim 5, wherein the compound or the pharmaceutically acceptable salt thereof is administered at a dose of 200 mg once a day.

32. The method of claim 6, wherein the further therapeutic agent is an agent for the prophylaxis and/or treatment of cardiovascular disease.

33. The method of claim 6, wherein the further therapeutic agent is an agent for the prophylaxis and/or treatment of atherosclerosis.

\* \* \* \* \*